(12) United States Patent
Vehring et al.

(10) Patent No.: US 9,415,009 B2
(45) Date of Patent: Aug. 16, 2016

(54) COMPOSITIONS, METHODS AND SYSTEMS FOR RESPIRATORY DELIVERY OF TWO OR MORE ACTIVE AGENTS

(71) Applicant: Pearl Therapeutics, Inc., Redwood City, CA (US)

(72) Inventors: Reinhard Vehring, Edmonton (CA); Michael Steven Hartman, Millbrae, CA (US); David Lechuga-Ballesteros, San Jose, CA (US); Adrian Edward Smith, Emerald Hills, CA (US); Vidya B. Joshi, Redwood City, CA (US); Sarvajna Kumar Dwivedi, Redwood City, CA (US)

(73) Assignee: Pearl Therapeutics, Inc., Redwood City, CA (US)

( * ) Notice: Subject to any disclaimer, the term of this patent is extended or adjusted under 35 U.S.C. 154(b) by 0 days.

(21) Appl. No.: 14/334,503

(22) Filed: Jul. 17, 2014

(65) Prior Publication Data
US 2015/0017104 A1    Jan. 15, 2015

Related U.S. Application Data

(63) Continuation of application No. 13/109,884, filed on May 17, 2011, now Pat. No. 8,815,258, which is a continuation-in-part of application No. 12/790,710, filed on May 28, 2010.

(60) Provisional application No. 61/182,565, filed on May 29, 2009, provisional application No. 61/258,172, filed on Nov. 4, 2009, provisional application No. 61/309,365, filed on Mar. 1, 2010, provisional application No. 61/345,536, filed on May 17, 2010.

(51) Int. Cl.
| | |
|---|---|
| *A61K 9/12* | (2006.01) |
| *A61K 9/00* | (2006.01) |
| *A61K 31/167* | (2006.01) |
| *A61K 45/06* | (2006.01) |
| *A61M 15/00* | (2006.01) |
| *A61K 31/40* | (2006.01) |
| *A61K 31/138* | (2006.01) |
| *A61K 31/46* | (2006.01) |
| *A61K 31/56* | (2006.01) |
| *A61K 31/58* | (2006.01) |

(52) U.S. Cl.
CPC ............ *A61K 9/008* (2013.01); *A61K 9/124* (2013.01); *A61K 31/138* (2013.01); *A61K 31/167* (2013.01); *A61K 31/40* (2013.01); *A61K 31/46* (2013.01); *A61K 31/56* (2013.01); *A61K 31/58* (2013.01); *A61K 45/06* (2013.01); *A61M 15/0065* (2013.01)

(58) Field of Classification Search
CPC ..... A61K 9/008; A61K 31/167; A61K 45/06; A61K 31/56; A61K 31/58; A61K 31/40; A61K 9/124; A61K 31/138; A61K 31/46; A61K 2300/00; A61M 15/0065
See application file for complete search history.

(56) References Cited

U.S. PATENT DOCUMENTS

| | | |
|---|---|---|
| 2,956,062 A | 10/1960 | Lunsford |
| 3,929,768 A | 12/1975 | Brattsand et al. |
| 3,994,974 A | 11/1976 | Murakami et al. |
| 4,187,301 A | 2/1980 | Edwards |
| 4,335,121 A | 6/1982 | Phillipps et al. |
| 4,472,393 A | 9/1984 | Shapiro |
| 4,992,474 A | 2/1991 | Skidmore et al. |
| 5,126,375 A | 6/1992 | Skidmore et al. |
| 5,225,445 A | 7/1993 | Skidmore et al. |
| 5,610,163 A | 3/1997 | Banholzer et al. |
| 5,612,053 A | 3/1997 | Baichwal et al. |
| 5,654,314 A | 8/1997 | Banholzer et al. |
| 5,684,199 A | 11/1997 | Francotte |
| 5,707,634 A | 1/1998 | Schmitt |
| 5,709,884 A | 1/1998 | Trofast et al. |
| 5,727,333 A | 3/1998 | Folan |
| 5,833,891 A | 11/1998 | Subramaniam et al. |
| 5,851,453 A | 12/1998 | Hanna et al. |
| 5,858,410 A | 1/1999 | Muller et al. |
| 5,886,200 A | 3/1999 | Kwok et al. |
| 5,889,015 A | 3/1999 | Sequeira et al. |
| 5,928,469 A | 7/1999 | Franks et al. |
| 6,030,604 A | 2/2000 | Trofast |
| 6,040,344 A | 3/2000 | Gao et al. |
| 6,054,488 A | 4/2000 | Oliver et al. |

(Continued)

FOREIGN PATENT DOCUMENTS

| | | |
|---|---|---|
| AU | 642913 B2 | 4/1991 |
| AU | 775588 B2 | 12/2000 |

(Continued)

OTHER PUBLICATIONS

Vippagunta et al. "Crystalline Solids," Advanced Drug Delivery Reviews, 2001,48, 3-26.*

(Continued)

*Primary Examiner* — Suzanne Ziska
(74) *Attorney, Agent, or Firm* — Seed IP Law Group PLLC

(57) ABSTRACT

Compositions, methods and systems are provided for pulmonary or nasal delivery of two or more active agents via a metered dose inhaler. In one embodiment, the compositions include a suspension medium, active agent particles, and suspending particles, in which the active agent particles and suspending particles form a co-suspension within the suspension medium.

49 Claims, 32 Drawing Sheets

(56) References Cited

U.S. PATENT DOCUMENTS

| | | | |
|---|---|---|---|
| 6,057,307 A | 5/2000 | Sequeira et al. |
| 6,057,581 A | 5/2000 | Doan |
| 6,063,138 A | 5/2000 | Hanna et al. |
| 6,068,832 A | 5/2000 | Berry et al. |
| 6,129,905 A | 10/2000 | Cutie |
| 6,177,560 B1 | 1/2001 | Heggie et al. |
| 6,258,341 B1 | 7/2001 | Foster et al. |
| 6,260,549 B1 | 7/2001 | Sosiak |
| 6,309,623 B1 | 10/2001 | Weers et al. |
| 6,309,671 B1 | 10/2001 | Foster et al. |
| 6,358,530 B1 | 3/2002 | Eljamal et al. |
| 6,365,581 B1 | 4/2002 | Sequeira et al. |
| 6,372,258 B1 | 4/2002 | Platz et al. |
| 6,433,027 B1 | 8/2002 | Bozung et al. |
| 6,433,040 B1 | 8/2002 | Dellamary et al. |
| 6,451,285 B2 | 9/2002 | Blondino et al. |
| 6,455,524 B1 | 9/2002 | Bozung et al. |
| RE37,872 E | 10/2002 | Franks et al. |
| 6,475,467 B1 | 11/2002 | Keller et al. |
| 6,518,239 B1 | 2/2003 | Kuo et al. |
| 6,537,524 B1 | 3/2003 | Hassan et al. |
| 6,565,885 B1 | 5/2003 | Tarara et al. |
| 6,630,466 B2 | 10/2003 | Bozung et al. |
| 6,638,495 B2 | 10/2003 | Weers et al. |
| 6,667,344 B2 | 12/2003 | Banerjee et al. |
| 6,677,322 B2 | 1/2004 | Sequeira et al. |
| 6,677,323 B2 | 1/2004 | Sequeira et al. |
| 6,719,994 B2 | 4/2004 | Meoli et al. |
| 6,777,423 B2 | 8/2004 | Banholzer et al. |
| 6,814,953 B2 | 11/2004 | Banerjee et al. |
| 6,908,928 B2 | 6/2005 | Banholzer et al. |
| 6,942,821 B2 | 9/2005 | Dayrit et al. |
| 6,946,117 B1 | 9/2005 | Schutt et al. |
| 6,964,759 B2 | 11/2005 | Lewis et al. |
| 7,067,502 B2 | 6/2006 | Hassan et al. |
| 7,186,401 B2 | 3/2007 | Keller et al. |
| 7,205,343 B2 | 4/2007 | Dellamary et al. |
| 7,229,607 B2 | 6/2007 | Bannister et al. |
| 7,244,742 B2 | 7/2007 | Pieper et al. |
| RE39,820 E | 9/2007 | Banholzer et al. |
| 7,273,604 B2 | 9/2007 | Hills et al. |
| 7,306,787 B2 | 12/2007 | Tarara et al. |
| 7,393,544 B2 | 7/2008 | Dellamary et al. |
| 7,442,388 B2 | 10/2008 | Weers et al. |
| 7,566,705 B2 | 7/2009 | Hassan et al. |
| 7,628,978 B2 | 12/2009 | Weers et al. |
| 7,736,670 B2 | 6/2010 | Staniforth et al. |
| 7,790,145 B2 | 9/2010 | Weers et al. |
| 7,915,303 B2 | 3/2011 | Baxter |
| 7,985,766 B2 | 7/2011 | Goede et al. |
| 8,048,451 B2 | 11/2011 | Staniforth et al. |
| 8,048,910 B2 | 11/2011 | Maus et al. |
| 8,080,263 B2 | 12/2011 | Dellamary et al. |
| 8,168,223 B1 | 5/2012 | Tarara et al. |
| 8,246,934 B2 | 8/2012 | Weers et al. |
| 8,252,268 B2 | 8/2012 | Slowey et al. |
| 8,303,991 B2 | 11/2012 | Staniforth et al. |
| 8,324,266 B2 | 12/2012 | Vehring et al. |
| 8,435,567 B2 | 5/2013 | Staniforth et al. |
| 8,703,806 B2 | 4/2014 | Vehring et al. |
| 2002/0188281 A1 | 12/2002 | Dellamary et al. |
| 2003/0018019 A1 | 1/2003 | Meade et al. |
| 2003/0068280 A1 | 4/2003 | Bannister et al. |
| 2003/0114428 A1 | 6/2003 | Sequeira et al. |
| 2004/0081584 A1 | 4/2004 | Doyrit et al. |
| 2004/0081627 A1 | 4/2004 | Jinks et al. |
| 2004/0101483 A1 | 5/2004 | Muller-Walz et al. |
| 2004/0170568 A1 | 9/2004 | Weers et al. |
| 2005/0042174 A1 | 2/2005 | Nilsson et al. |
| 2005/0080052 A1 | 4/2005 | Hills et al. |
| 2005/0121026 A1 | 6/2005 | Nilsson et al. |
| 2005/0175548 A1 | 8/2005 | Goede et al. |
| 2005/0175549 A1 | 8/2005 | Goede et al. |
| 2005/0207986 A1 | 9/2005 | Schutt et al. |
| 2005/0255049 A1 | 11/2005 | Slowey et al. |
| 2005/0287077 A1 | 12/2005 | Creazzo et al. |
| 2006/0148693 A1 | 7/2006 | Wollin |
| 2006/0159629 A1* | 7/2006 | Tarara et al. ............... 424/46 |
| 2006/0165606 A1 | 7/2006 | Tarara et al. |
| 2006/0252815 A1 | 11/2006 | Goede et al. |
| 2006/0257324 A1 | 11/2006 | Lewis et al. |
| 2006/0269484 A1 | 11/2006 | Knopeck et al. |
| 2007/0104658 A1 | 5/2007 | Batycky et al. |
| 2007/0122351 A1 | 5/2007 | Kunka et al. |
| 2007/0193577 A1 | 8/2007 | Keller |
| 2007/0196285 A1 | 8/2007 | Maus et al. |
| 2007/0212405 A1 | 9/2007 | Dellamary et al. |
| 2007/0270481 A1 | 11/2007 | Goede et al. |
| 2008/0125407 A1 | 5/2008 | Chu et al. |
| 2008/0220073 A1 | 9/2008 | Bannister et al. |
| 2008/0226564 A1 | 9/2008 | Weers et al. |
| 2008/0227690 A1 | 9/2008 | Schmitke et al. |
| 2008/0233194 A1 | 9/2008 | Dellamary et al. |
| 2008/0267886 A1* | 10/2008 | Collingwood ............... 424/43 |
| 2008/0274189 A1 | 11/2008 | Collingwood et al. |
| 2008/0279948 A1 | 11/2008 | Collingwood et al. |
| 2008/0286363 A1 | 11/2008 | Collingwood et al. |
| 2008/0300226 A1 | 12/2008 | Goede et al. |
| 2008/0317862 A1 | 12/2008 | Collingwood et al. |
| 2009/0088408 A1 | 4/2009 | Meade et al. |
| 2009/0130026 A1 | 5/2009 | Lewis et al. |
| 2009/0298802 A1 | 12/2009 | Sequeira et al. |
| 2010/0034890 A1 | 2/2010 | Clarke et al. |
| 2010/0197719 A1 | 8/2010 | Bozung et al. |
| 2010/0329984 A1 | 12/2010 | Weers et al. |
| 2011/0023876 A1 | 2/2011 | Vehring et al. |
| 2011/0132356 A1 | 6/2011 | Vehring et al. |
| 2011/0132357 A1 | 6/2011 | Vehring et al. |
| 2011/0135737 A1 | 6/2011 | Vehring et al. |
| 2012/0024554 A1 | 2/2012 | Boehm et al. |
| 2012/0039817 A1 | 2/2012 | Vehring et al. |
| 2012/0039952 A1 | 2/2012 | Vehring et al. |
| 2013/0092160 A1 | 4/2013 | Vehring et al. |

FOREIGN PATENT DOCUMENTS

| | | |
|---|---|---|
| CA | 2 442 415 A1 | 10/2002 |
| CA | 2 479 638 A1 | 10/2003 |
| CA | 2 495 454 A1 | 3/2004 |
| CA | 2 527 178 A1 | 12/2004 |
| CA | 2 607 391 A1 | 11/2006 |
| CN | 1170356 A | 1/1998 |
| DE | 10214264 A1 | 10/2003 |
| EP | 0 416 950 A1 | 3/1991 |
| EP | 0 416 951 A1 | 3/1991 |
| EP | 0 418 716 A1 | 3/1991 |
| EP | 1 621 197 A2 | 4/2003 |
| EP | 1 408 967 B1 | 4/2004 |
| EP | 1 530 471 B1 | 5/2005 |
| EP | 1 570 861 A2 | 9/2005 |
| EP | 1 651 270 B1 | 3/2007 |
| EP | 1 894 568 A1 | 3/2008 |
| EP | 1 718 336 B1 | 6/2008 |
| EP | 1 651 221 B1 | 1/2009 |
| EP | 2 036 572 A1 | 3/2009 |
| EP | 1 971 369 B1 | 8/2009 |
| EP | 2 098 248 A1 | 9/2009 |
| EP | 1 755 590 B1 | 8/2011 |
| EP | 1 651 224 B1 | 10/2011 |
| EP | 1 019 021 B2 | 12/2012 |
| EP | 2 037 879 B1 | 5/2013 |
| JP | 2000-513340 A | 10/2000 |
| JP | 2003-525842 A | 9/2003 |
| JP | 2007-520506 A | 7/2007 |
| JP | 2007-520508 A | 7/2007 |
| JP | 2008-503500 A | 2/2008 |
| JP | 2008-521788 A | 6/2008 |
| JP | 2008-534611 A | 8/2008 |
| JP | 2012-513311 A | 6/2012 |
| RU | 2 319 512 C2 | 3/2008 |
| WO | 86/03750 A1 | 7/1986 |
| WO | 91/14468 A1 | 10/1991 |
| WO | 92/04365 A1 | 3/1992 |
| WO | 92/16528 A1 | 10/1992 |

(56) References Cited

FOREIGN PATENT DOCUMENTS

| | | | |
|---|---|---|---|
| WO | 93/11773 A1 | 6/1993 |
| WO | 95/05805 A1 | 3/1995 |
| WO | 95/15151 A1 | 6/1995 |
| WO | 96/19198 A1 | 6/1996 |
| WO | 96/32149 A1 | 10/1996 |
| WO | 96/32344 A1 | 10/1996 |
| WO | 97/38741 A1 | 10/1997 |
| WO | 97/39758 A1 | 10/1997 |
| WO | 97/44080 A1 | 11/1997 |
| WO | 98/41193 A1 | 9/1998 |
| WO | 99/15182 A1 | 4/1999 |
| WO | 99/16422 A1 | 4/1999 |
| WO | 00/32165 A1 | 6/2000 |
| WO | 00/36915 A1 | 6/2000 |
| WO | 00/53157 A1 | 9/2000 |
| WO | 00/53187 | * | 9/2000 |
| WO | 00/53187 A1 | 9/2000 |
| WO | 00/61108 A1 | 10/2000 |
| WO | 00/69468 A1 | 11/2000 |
| WO | 01/00312 A1 | 1/2001 |
| WO | 01/04118 A2 | 1/2001 |
| WO | 01/54664 A1 | 8/2001 |
| WO | 01/76575 A2 | 10/2001 |
| WO | 02/14293 A1 | 2/2002 |
| WO | 02/078671 A1 | 10/2002 |
| WO | 02/085326 A2 | 10/2002 |
| WO | 2004/014293 A2 | 2/2004 |
| WO | 2004/105759 A2 | 12/2004 |
| WO | 2005/000267 A2 | 1/2005 |
| WO | 2005/013994 A1 | 2/2005 |
| WO | 2005/014005 A1 | 2/2005 |
| WO | 2005/074900 A1 | 8/2005 |
| WO | 2005/110402 A1 | 11/2005 |
| WO | 2006/114379 A1 | 11/2006 |
| WO | 2006/128847 A2 | 12/2006 |
| WO | 2007/009164 A1 | 1/2007 |
| WO | 2007/057219 A1 | 5/2007 |
| WO | 2007/057221 A1 | 5/2007 |
| WO | 2007/057222 A1 | 5/2007 |
| WO | 2007/057223 A1 | 5/2007 |
| WO | 2007/095041 A1 | 8/2007 |
| WO | 2007/134964 A1 | 11/2007 |
| WO | 2008/000482 A1 | 1/2008 |
| WO | 2008/014161 A2 | 1/2008 |
| WO | 2008/025787 A2 | 3/2008 |
| WO | 2008/102128 A2 | 8/2008 |
| WO | 2009/095681 A2 | 8/2009 |
| WO | 2010/097188 A1 | 9/2010 |
| WO | 2010/138862 A2 | 12/2010 |
| WO | 2010/138868 A2 | 12/2010 |
| WO | 2010/138884 A2 | 12/2010 |
| WO | 2012/051426 A2 | 4/2012 |
| WO | 2012/110770 A2 | 8/2012 |
| WO | 2012/120284 A1 | 9/2012 |
| WO | 2012/158166 A1 | 11/2012 |

OTHER PUBLICATIONS

Braga et al. (Chem. Commun., "Making Crystals from Crystals: a green route to crystal engineering and polymorphism," 2005, pp. 3635-3645.*

Seddon, K.R., "Pseudopolymorph: a polemic," Crystal Growth & Design, 2004, 4(6), pp. 1087, web release date Oct. 19, 2004.*

Symbicort® product sheet http://www.drugs.com/newdrugs/astrazene-s-symbicort-budesonide-formoterol-asthma-approved-fda-1297; retrieved Oct. 28, 2013 in related U.S. Appl. No. 13/109,884.*

Capraz et al ("The Effect of Inhaled Budesonide and Formoterol on Bronchial Remodeling and HRCT Features in Young Asthmatics," Lung (2007) 185:89-960) [Capraz].*

"Guidance for Industry: Nasal Spray and Inhalation Solution, Suspension, and Spray Drug Products—Chemistry, Manufacturing, and Controls Documentation," retrieved on Feb. 19, 2014 from http://www.fda.gov/downloads/drugs/guidanceComplianceRegulatoryInformation/Guidance/ucm070575.pdf, U.S. Department of Health and Human Services, Food and Drug Administration, Center for Drug Evaluation and Research, pp. 13-14, Jul. 2002, 49 pages.

"Remington: The Science and Practice of Pharmacy," Table 16-1, $21^{st}$ Edition, *Williams & Wilkins*, p. 212, 2006, 3 pages.

Applicant Initiated Interview Summary, issued Apr. 9, 2014, for U.S. Appl. No. 12/790,605, 2 pages.

Applicant Initiated Interview Summary, issued Aug. 2, 2012, for U.S. Appl. No. 13/281,726, 6 pages.

Applicant Initiated Interview Summary, issued Dec. 12, 2012, for U.S. Appl. No. 12/790,448, 3 pages.

Applicant Initiated Interview Summary, issued Dec. 20, 2012, for U.S. Appl. No. 12/790,605, 3 pages.

Applicant Initiated Interview Summary, issued Feb. 22, 2013, for co-pending U.S. Appl. No. 12/790,448, 3 pages.

Applicant Initiated Interview Summary, issued Jan. 30, 2012, for corresponding U.S. Appl. No. 12/790,671, 3 pages.

Applicant Initiated Interview Summary, issued May 22, 2012, for corresponding U.S. Appl. No. 12/790,671, 3 pages.

Applicant Initiated Interview Summary, issued Oct. 28, 2013, for U.S. Appl. No. 13/692,904, 3 pages.

Applicant Initiated Interview Summary, issued Sep. 27, 2012, for U.S. Appl. No. 13/281,726, 3 pages.

Applicant Initiated Interview Summary, mailed May 23, 2012, for corresponding U.S. Appl. No. 12/790,605, 3 pages.

Baculard, "Place du Bronchodual® dans le traitement de fond de l'asthme de l'enfant," *Arch Péditar 2*(Suppl 2):149s-153s, 1995.

Barnes, "Chronic obstructive pulmonary disease: new opportunities for drug development," *Trends in Pharmacological Sciences* 19:415-423, 1998.

Barnes, "Efficacy of Inhaled Corticosteroids in Asthma," *Allergy Clin Immunol 102*:531-538 1998.

Beck, "Utilisation du bromure d'ipratropium par voie inhalée pour de traitement de l'asthme aigu chez l'enfant Expérience Clinique," *Arch Pédiatar 2*(Suppl 2):145s-148s, 1995.

Braga et al., "Making crystals from crystals: a green route to crystal engineering and polymorphism," *Chem Comm*, pp. 3635-3645, 2005.

Brambilla et al., "Modulation of aerosol clouds produced by pressurised inhalation aerosols," *International Journal of Pharmaceutics 186*:53-61, 1999.

Capraz et al., "The Effect of Inhaled Budesonide and Formoterol on Bronchial Remodeling and HRCT Features in Young Asthmatics," *Lung 185*:89-96, 2007.

Cazzola et al., "Incremental Benefit of Adding Oxitropium Bromide to Formoterol in Patients with Stable COPD," *Pulmonary Pharmacology & Therapeutics 12*:267-271, 1999.

Cydulka et al., "Effects of Combined Treatment with Glycopyrrolate and Albuterol in Acute Exacerbation of Chronic Obstructive Pulmonary Disease," *Annals of Emergency Medicine 25*:470-473, 1995.

da Rocha et al., "Science and Technology of Pressurized Metered-Dose Inhalers," *Controlled Pulmonary Drug Delivery*, Chapter 8, pp. 165-201, 2011.

Dellamary et al., "Hollow Porous Particles in Metered Dose Inhalers," *Pharmaceutical Research 17*(2):168-174, 2000.

Drugs Information Online, "FDA Approves Symbicort: Astrazeneca's Symbicort (budesonide/formoterol) Treatment for Asthma Approved by the FDA," retrieved on Oct. 28, 2013, from www.Drugs.com, Jul. 22, 2006, 2 pages Duddu et al., "Improved Lung Delivery from a Passive Dry Powder Inhaler Using an Engineered PulmoSphere Powder," *Pharmaceutical Research 19*(5):689-695 2002.

Hansel et al., "Glycopyrrolate Causes Prolonged Bronchoprotection and Bronchodilatation in Patients with Asthma," *Chest 128*:1974-1979, 2005.

Hartman et al., "The Efficiency and Stability of a Novel Lipid-based Budesonide Metered Dose Inhaler Formulation Utilizing HFA," AAPS Annual Meeting and Exposition, Salt Lake City, UT, Oct. 26-30, 2003, 1 page.

Hirst et al., "In Vivo Lung Deposition of Hollow Porous Particles from a Pressurized Metered Dose Inhaler," *Pharmaceutical Research 19*(3):258-264, 2002.

(56) References Cited

OTHER PUBLICATIONS

Hoye et al., "Measurement and Correlation of Solute Solubility in HFA-134a/Ethanol Systems," *International Journal of Pharmaceutics 362*:184-188, 2008.
International Preliminary Report on Patentability, issued Nov. 29, 2011, for International Application No. PCT/US2010/036650, 10 pages.
International Preliminary Report on Patentability, issued Nov. 29, 2011, for International Application No. PCT/US2010/036676, 9 pages.
International Preliminary Report on Patentability, issued Nov. 19, 2013, for International Application No. PCT/US2011/036868, 8 pages.
International Preliminary Report on Patentability, mailed Dec. 8, 2011, for International Application No. PCT/US2010/036659, 11 pages.
International Search Report, dated Aug. 12, 2011, for International Application No. PCT/US2011/036868, 8 pages.
International Search Report, mailed Feb. 25, 2011, for International Application No. PCT/US2010/036650, 5 pages.
International Search Report, mailed Feb. 25, 2011, for International Application No. PCT/US2010/036659, 5 pages.
International Search Report, mailed Feb. 25, 2011, for International Application No. PCT/US2010/036676, 5 pages.
International Search Report, mailed May 20, 2014, for corresponding International Application No. PCT/US2014/029489, 9 pages.
James et al., "The surface characterisation and comparison of two potential sub-micron, sugar bulking excipients for use in low-dose, suspension formulations in metered dose inhalers," *International Journal of Pharmaceutics 361*(1-2):209-221, 2008.
Johnson et al., "Effect of Inhaled glycopyrrolate and atropine in asthma. Precipitated by exercise and cold air inhalation," *Chest 85*(3):325-328, 1984.
Kazmi et al., "Methods and Systems for Conditioning of Particulate Crystalline Materials," U.S. Appl. No. 14/213,834, filed Mar. 14, 2014, 89 pages.
Lechuga-Ballessteros et al., "Residual Water in Amorphous Solids, Measurement and Effects on Stability," In Progress in Amorphous Food and Pharmaceutical Systems, Levine, H., Ed. The Royal Society of Chemistry; London, pp. 275-316, 2002.
Lechuga-Ballesteros et al., "Compositions, Methods and Systems for Respiratory Delivery of Three or More Active Agents," U.S. Appl. No. 14/285,435, filed May 22, 2014, 92 pages.
Leckie et al., "Novel Therapy for COPD," *Exp. Opin. Invest. Drugs 9*(1):3-23, 2000.
Mahler et al., "Effectiveness of Fluticasone Propionate and Salmeterol Combination Delivered via the Diskus Device in the Treatment of Chronic Obstructive Pulmonary Disease," *Am J Respir Crit Care Med 166*:1084-1091, 2002.
Miller, "Qualitative Effects of Water on Suspension Aerosol Formulations," *Respiratory Drug Delivery*, CRC Press, p. 250, 1990, 3 pages.
Newhouse et al., "Inhalation of a Dry Powder Tobramycin PulmoSphere Formulation in Healthy Volunteers," *Chest 124*:360-366, 2003.
Office Action, mailed Jun. 27, 2014, for corresponding Chinese Patent Application No. 201080033310.3, 17 pages. (with English Translation).
Ridder et al., "Surfactant solubility and aggregate orientation in hydrofluoroalkanes," *International Journal of Pharmaceutics 295*:57-65, 2005.
Rogueda, "Novel hydrofluoroalkane suspension formulations for respiratory drug delivery," *Expert Opin. Drug Deliv. 2*(4):625-638, 2005.
Schroeckenstein et al., "Twelve-hour bronchodilation in asthma with a single aerosol dose of the anticholinergic compound glycopyrrolate," *J Allergy Clin. Immunol. 82*(1):115-119, 1988.
Seddon, "Pseudopolymorph: a Polemic," *Crystal Growth & Design 4*(6):1087, 2004, 2 pages.
Singh et al., "NVA237, a once-daily inhaled antimuscarin moderate-to-severe COPD," presented at the American Thoracic Society International Conference, San Diego, California, May 19-24, 2006, poster, 2 pages.
Skorodin, "Pharmacotherapy for Asthma and Chronic Obstructive Pulmonary Disease," *Arch. Intern. Med. 153*:814-828, 1993.
Tarara et al., "Characterization of Suspension-Based Metered Dose Inhaler Formulations Composed of Spray-Dried Budesonide Microcrystals Dispersed in HFA-134a," *Pharmaceutical Research 21*(9):1607-1614, 2004.
Vehring et al., "Compositions for Pulimonary Delivery of Long-Acting Muscarinic Antagonists and Associated Methods and Systems," Advisory Action, issued Feb. 1, 2013, for co-pending U.S. Appl. No. 12/790,448, 2 pages.
Vehring et al., "Compositions for Pulimonary Delivery of Long-Acting Muscarinic Antagonists and Associated Methods and Systems," Office Action, issued May 7, 2012, for co-pending U.S. Appl. No. 12/790,448, 30 pages.
Vehring et al., "Compositions for Pulimonary Delivery of Long-Acting Muscarinic Antagonists and Associated Methods and Systems," Office Action, issued Oct. 16, 2012, for co-pending U.S. Appl. No. 12/790,448, 18 pages.
Vehring et al., "Compositions for Pulimonary Delivery of Long-Acting Muscarinic Antagonists and Associated Methods and Systems," Response to Office Action, dated May 7, 2012, filed Aug. 7, 2012, for co-pending U.S. Appl. No. 12/790,448, 19 pages.
Vehring et al., "Compositions for Pulimonary Delivery of Long-Acting Muscarinic Antagonists and Associated Methods and Systems," Response to Office Action, issued Oct. 16, 2012, filed Jan. 16, 2013, for co-pending U.S. Appl. No. 12/790,448, 17 pages.
Vehring et al., "Compositions for Pulimonary Delivery of Long-Acting Muscarinic Antagonists and Associated Methods and Systems," Response to Office Action, issued Oct. 16, 2012, filed Mar. 1, 2012, for co-pending U.S. Appl. No. 12/790,448, 20 pages.
Vehring et al., "Compositions for Pulimonary Delivery of Long-Acting Muscarinic Antagonists and Associated Methods and Systems," Preliminary Amendment, filed Apr. 24, 2012, for co-pending U.S. Appl. No. 12/790,448, 8 pages.
Vehring et al., "Compositions for Pulmonary Delivery of Long-Acting B2 Adrenergic Receptor Agonists and Associated Methods and Systems," Office Action, mailed Aug. 16, 2012, for corresponding U.S. Appl. No. 12/790,605, 14 pages.
Vehring et al., "Compositions for Pulmonary Delivery of Long-Acting B2 Adrenergic Receptor Agonists and Associated Methods and Systems," Office Action, mailed Mar. 1, 2012, for corresponding U.S. Appl. No. 12/790,605, 11 pages.
Vehring et al., "Compositions for Pulmonary Delivery of Long-Acting B2 Adrenergic Receptor Agonists and Associated Methods and Systems," Response to Office Action, mailed Aug. 16, 2012, filed Jan. 16, 2013, for corresponding U.S. Appl. No. 12/790,605, 26 pages.
Vehring et al., "Compositions for Pulmonary Delivery of Long-Acting B2 Adrenergic Receptor Agonists and Associated Methods and Systems," Response to Office Action, dated Mar. 1, 2012, filed Jun. 1, 2012, for corresponding U.S. Appl. No. 12/790,605, 23 pages.
Vehring et al., "Compositions for Pulmonary Delivery of Long-Acting B2 Adrenergic Receptor Agonists and Associated Methods and Systems," Response to Office Action, issued Sep. 6, 2013, filed Dec. 6, 2013, for corresponding U.S. Appl. No. 12/790,605, 24 pages.
Vehring et al., "Compositions for Pulmonary Delivery of Long-Acting B2 Adrenergic Receptor Agonists and Associated Methods and Systems," Office Action, issued Sep. 6, 2013, for corresponding U.S. Appl. No. 12/790,605, 18 pages.
Vehring et al., "Compositions for Pulmonary Delivery of Long-Acting B2 Adrenergic Receptor Agonists and Associated Methods and Systems," Notice of Allowance, mailed Apr. 9, 2014, U.S. Appl. No. 12/790,605, 11 pages.
Vehring et al., "Compositions for Respiratory Delivery of Active Agents and Associated Methods and Systems," Advisory Action, mailed Jun. 27, 2012, for U.S. Appl. No. 12/790,671, 3 pages.
Vehring et al., "Compositions for Respiratory Delivery of Active Agents and Associated Methods and Systems," Office Action, mailed Nov. 14, 2011, for corresponding U.S. Appl. No. 12/790,671, 15 pages.

(56) References Cited

OTHER PUBLICATIONS

Vehring et al., "Compositions for Respiratory Delivery of Active Agents and Associated Methods and Systems," Office Action, mailed Apr. 11, 2012, for U.S. Appl. No. 12/790,671, 18 pages.
Vehring et al., "Compositions for Respiratory Delivery of Active Agents and Associated Methods and Systems," Response to Office Action, mailed Apr. 11, 2012, filed Sep. 11, 2012, for U.S. Appl. No. 12/790,671, 29 pages.
Vehring et al., "Compositions for Respiratory Delivery of Active Agents and Associated Methods and Systems," Response to Office Action, dated February 19, 2014, filed Jul. 21, 2014, for corresponding U.S. Appl. No. 12/790,671, 33 pages.
Vehring et al., "Compositions, Methods and Systems for Respiratory Delivery of Two or More Active Agents," Response to Office Action, dated Feb. 17, 2012, filed May 16, 2012, for U.S. Appl. No. 13/281,726, 20 pages.
Vehring et al., "Compositions, Methods and Systems for Respiratory Delivery of Two or More Active Agents," Response to Office Action, issued Mar. 28, 2013, filed Sep. 27, 2013, for co-pending U.S. Appl. No. 13/692,904, 21 pages.
Vehring et al., "Compositions, Methods and Systems for Respiratory Delivery of Two or More Active Agents," Amendment, filed on Jan. 31, 2014, for U.S. Appl. No. 13/109,884, 22 pages.
Vehring et al., "Compositions, Methods and Systems for Respiratory Delivery of Two or More Active Agents," Preliminary Amendment, filed Oct. 14, 2011, for U.S. Appl. No. 13/109,884, 16 pages.
Vehring et al., "Compositions, Methods and Systems for Respiratory Delivery of Two or More Active Agents," Preliminary Amendment, filed Dec. 3, 2012, for U.S. Appl. No. 13/692,904, 13 pages.
Vehring et al., "Compositions, Methods and Systems for Respiratory Delivery of Glycopyrrolate and Two or More Active Agents," Notice of Allowance, mailed Oct. 28, 2013, for U.S. Appl. No. 13/692,904, 13 pages.
Vehring et al., "Compositions, Methods and Systems for Respiratory Delivery of Glycopyrrolate and Two or More Active Agents," Office Action, issued Mar. 28, 2013, for co-pending U.S. Appl. No. 13/692,904, 12 pages.
Vehring et al., "Compositions, Methods and Systems for Respiratory Delivery of Two or More Active Agents," U.S. Appl. No. 14/257,828, filed Apr. 21, 2014, 132 pages.
Vehring et al., "Compositions, Methods and Systems for Respiratory Delivery of Two or More Active Agents," Office Action, issued Nov. 20, 2013, for U.S. Appl. No. 12/790,710, 19 pages.
Vehring et al., "Compositions, Methods and Systems for Respiratory Delivery of Two or More Active Agents," Office Action, issued Oct. 31, 2013, for U.S. Appl. No. 13/109,884, 16 pages.
Vehring et al., "Compositions, Methods and Systems for Respiratory Delivery of Two or More Active Agents," Notice of Allowance, mailed Aug. 2, 2012, for U.S. Appl. No. 13/281,726, 5 pages.
Vehring et al., "Compositions, Methods and Systems for Respiratory Delivery of Two or More Active Agents," Amendment After Allowance, filed Sep. 21, 2012, for U.S. Appl. No. 13/281,726, 11 pages.
Vehring et al., "Compositions, Methods and Systems for Respiratory Delivery of Two or More Active Agents," Office Action, mailed Feb. 17, 2012, for U.S. Appl. No. 13/281,726, 27 pages.
Vehring et al., "Compositions, Methods and Systems for Respiratory Delivery of Two or More Active Agents," Supplemental Amendment, filed Oct. 3, 2013, for co-pending U.S. Appl. No. 13/692,904, 13 pages.
Vehring et al., "Compositions, Methods and Systems for Respiratory Delivery of Two or More Active Agents," Amendment After Allowance, filed Dec. 23, 2013, for co-pending U.S. Appl. No. 13/692,904, 18 pages.
Vehring et al., "Compositions, Methods and Systems for Respiratory Delivery of Two or More Active Agents," Preliminary Amendment, filed Dec. 3, 2013, for co-pending U.S. Appl. No. 13/692,904, 13 pages.
Vehring et al., "Compositions, Methods and Systems for Respiratory Delivery of Two or More Active Agents," Amendment After Allowance, dated Aug. 2, 2012, filed Sep. 21, 2012, for U.S. Appl. No. 13/281,726, 11 pages.
Vervaet et al., "Drug-surfactant-propellant interactions in HFA-formulations," *International Journal of Pharmaceutics* 186:13-30, 1999.
Vippagunta et al., "Crystalline solids," *Advanced Drug Delivery Reviews* 48:3-26, 2001.
Walker et al., "Prolonged effect of inhaled glycopyrrolate in asthma," *Chest* 91(1):49-51, 1987.
Wermuth (Ed.), "The Practice of Medicinal Chemistry: Chapter 37, Preparation of Water-Soluble Compounds Through Salt Formulation," Academic Press, Third Edition, p. 758, 2008, 6 pages.
Wesseling et al., "A Comparison of the Effects of Anticholinergic and $\beta_2$-Agonist and Combination Therapy on Respiratory Impedance in COPD," *Chest* 101(1):166-173, 1992.
Young et al., "The influence of micronized particulates on the aerosolization properties of pressurized metered dose inhalers," *Aerosol Science* 40:324-337, 2009.
International Search Report, mailed Sep. 2, 2014, for corresponding International Application No. PCT/US/2014039234, 12 pages.
Office Action, dated Jul. 1, 2014, for corresponding Japanese Patent Application No. 2012-513319, 8 pages. (with English Translation).
Office Action, dated Jul. 11, 2014, for corresponding Russian Application No. 2011152960, 8 pages.
Zheng (ed.), "Formulation and Analytical Development for Low-Dose Oral Drug Products," John Wiley & Sons, Inc., Hoboken, New Jersey, Table 4.1, p. 65, 2009, 3 pages.
Blondino et al., "Surfactant Dissolution and Water Solubilization in Chlorine-Free Liquified Gas Propellants," Drug Development and Industrial Pharmacy, pp. 935-945, 1998.
Chinese Office Action, dated Jan. 16, 2015, for corresponding Chinese Patent Application No. 201080033310.3, 9 pages. (with English Translation).
Encyclopedia of Medicaments, M., RLS, p. 952, article Formoterol, pp. 642-643. (without English Abstract).
Japanese Office Action, dated Apr. 28, 2015, for corresponding Japanese Application No. 2012-513314, 8 pages. (with English Translation).
Japanese Office Action, dated Dec. 16, 2014, for corresponding Japanese Patent Application No. 2012-513319, 4 pages. (English Translation Only).
Japanese Office Action, dated Jan. 27, 2015, for corresponding Japanese Patent Application No. YTM/PP15-0004, 5 pages. (with English Translation).
Japanese Office Action, dated Jul. 1, 2014, for corresponding Japanese Patent Application No. 2012-513319, 8 pages. (with English Translation).
Panettieri et al., "Comparison of the efficacy and safety of arformoterol 15 microg twice daily and arformoterol 30 microg once daily in CORD: a single-dose, multicenter, randomized, modified-blind, two crossover study," *Clin. Ther.* 31(8):1716-1723, Aug. 2009. (Abstract Only).
Russian Office Action, dated Feb. 26, 2014, for corresponding Russian Application No. 2011154083/15, 6 pages. (English Translation Only).
Russian Office Action, dated May 7, 2015, received May 13, 2015, for corresponding Russian Application No. 2013155903/15(087185), 12 pages. (with English Translation).
Vehring et al., "Compositions for Pulmonary Delivery of Long-Acting Muscarinic Antagonists and Associated Methods and Systems," Final Office Action, mailed Nov. 24, 2014, for U.S. Appl. No. 12/780,448, 21 pages.
Vehring et al., "Compositions for Pulmonary Delivery of Long-Acting B2 Adrenergic Receptor Agonists and Associated Methods and Systems," Office Action, mailed May 1, 2015, for U.S. Appl. No. 14/327,425, 15 pages.
Vehring et al., "Compositions for Respiratory Delivery of Active Agents and Associated Methods and Systems," Office Action, mailed Apr. 10, 2015, for U.S. Appl. No. 12/790,671, 16 pages.

(56) References Cited

OTHER PUBLICATIONS

Vehring et al., "Compositions, Methods & Systems for Respiratory Delivery of Two or More Active Agents," Office Action, issued Nov. 20, 2013, for U.S. Appl. No. 12/790,710, 19 pages.
Vehring et al., "Compositions, Methods & Systems for Respiratory Delivery of Two or More Active Agents," Final Office Action, mailed Mar. 13, 2015, for U.S. Appl. No. 12/790,710, 23 pages.
Communication under Rule 71(3) EPC, for Application No. 10 727 551.3-1453, dated Jul. 14, 2015, 7 pages.
Communication under Rule 71(3) EPC, for Application No. 10 721 258.1-1453, dated Jul. 17, 2015, 5 pages.
Communication under Rule 71(3) EPC, for Application No. 10 727 553.9-1453, dated Jul. 14, 2015, 5 pages.
Taiwanese Office Action, dated Jul. 17, 2015 for corresponding Taiwanese Patent Application No. 099117219, 20 pages.
Vehring et al., "Compositions for Respiratory Delivery of Active Agents and Associated Methods and Systems," Office Action, dated Aug. 6, 2015 for U.S. Appl. No. 12/790,448, 34 pages.
Chinese Office Action, mailed Jun. 30, 2015, for corresponding Chinese Patent Application No. 201080033311.8, 7 pages. (with English Translation).
Singapore Search Report, mailed Jul. 3, 2015 for corresponding Singapore Patent Application No. 2013083431, 10 pages.
Singapore Written Opinion, mailed Jul. 3, 2015 for corresponding Singapore Patent Application No. 2013083431, 12 pages.
Ukrainian Office Action, dated Jun. 11, 2015, for corresponding Ukrainian Application No. a 2013 13538, 9 pages. (with English Translation).
Australian Notification of Allowance dated Sep. 8, 2015 for corresponding Australian Patent Application No. 2010253950, 1 page.
Australian Examination Report dated Jun. 29, 2015 for corresponding Australian Patent Application No. 2011368334, 3 pages.
Canadian Office Action, mailed Aug. 12, 2015, for corresponding Canadian Patent Application No. 2,763,939, 3 pages.
Decision on Grant mailed Aug. 27, 2015 for corresponding Russian Patent Application No. 2011152960, 27 pages.
Japanese Notice of Allowance dated Sep. 2, 2015 for corresponding Japanese Patent Application No. 2012-513314, 4 pages. (with English Translation).
Australian Examination Report dated Dec. 17, 2015, for corresponding Australian Patent Application No. 2015201037, 4 pages.
Chinese Office Action dated Dec. 28, 2015, for corresponding Chinese Patent Application No. 201080033311.8, 5 pages. (with translation).
Ecuador Opposition filed by Asociacion De Laboratorios Farmaceuticos (ALAFAR) on May 21, 2015 against Ecuadorean Patent Application No. SP-2013-13082, 16 pages. (with translation).
Ecuador Opposition filed by Roddome Pharmaceutical S.A. on May 7, 2015 against Ecuadorean Patent Application No. SP-2013-13082, 18 pages. (with translation).
Eurasian Office Action dated Dec. 9, 2015, for corresponding Eurasian Patent Application No. 210490991, 4 pages. (with translation).
European Intention to Grant dated Dec. 11, 2015, for corresponding European Patent Application No. 10 727 551.3, 7 pages.
European Intention to Grant dated Dec. 11, 2015, for corresponding European Patent Application No. 10 721 258.1, 7 pages.
European Intention to Grant dated Dec. 11, 2015, for corresponding European Patent Application No. 10 727 553.9, 7 pages.
International Preliminary Report on Patentability dated Nov. 24, 2015, for corresponding Patent Application No. PCT/US2014/039234, 8 pages.
Israeli Notification of Defects dated Dec. 13, 2015, for corresponding Israeli Patent Application No. 216467, 2 pages. (translation).
Israeli Notification of Defects dated Dec. 16, 2015, for corresponding Israeli Patent Application No. 216466, 3 pages. (translation).
Israeli Notification of Defects dated Dec. 13, 2015, for corresponding Israeli Patent Application No. 216468, 3 pages. (translation).
Japanese Notice of Allowance dated Dec. 17, 2015, for corresponding Japanese Patent Application No. 2012-513311, 4 pages. (with translation).
Japanese Notice of Allowance dated Dec. 17, 2015, for corresponding Japanese Patent Application No. 2012-513319, 5 pages. (with translation).
New Zealand Examination Report dated Nov. 25, 2015, for corresponding New Zealand Patent Application No. 617714, 1 page.
Oxis Turbuhaler, *RLS Drug Directory Encyclopedia*, downloaded Nov. 9, 2015, 18 pages, http://www.rlsnet.ru/tn_index_id_12220.htm. (with translation).
Russian Decision on Grant dated Nov. 2, 2015, for corresponding Russian Patent Application No. 2011154083/15, 30 pages. (with translation).
Russian Decision on Grant dated Jan. 11, 2016, for corresponding Russian Patent Application No. 2011154148/15, 54 pages. (with translation).
Vehring et al., "Compositions for Pulmonary Delivery of Long-Acting B2 Adrenergic Receptor Agonists and Associated Methods and Systems," U.S. Appl. No. 14/327,425, mailed Jan. 27, 2016, 15 pages.
Israeli Notification of Defects dated Feb. 8, 2016, for corresponding Israeli Application No. 229260, 6 pages.
New Zealand Further Examination Report dated Mar. 3, 2016, for corresponding New Zealand Application No. 617714, 2 pages.
New Zealand First Examination Report dated Mar. 3, 2016, for corresponding New Zealand Application No. 716787, 2 pages.
Japanese Office Action dated Mar. 22, 2016, for corresponding Japanese Application No. 2015-084226, 7 pages (with translation).
Japanese Office Action dated Mar. 22, 2016, for corresponding Japanese Application No. 2015-084240, 6 pages (with translation).
Singapore Written Opinion dated Apr. 11, 2016, for corresponding Singapore Application No. 2013083431, 13 pages (translation only).
Cummings et al., "Performance Advantages of Co-Suspension Formulation Technology for Manufacturing of Metered Dose Inhalers" *RDD Europe 2011—Respiratory Drug Delivery vol. 2*, pp. 387-390, published by Virginia Commonwealth University 2011.
Lechuga-Ballesteros, et al., "Novel cosuspension metered-dose inhalers for the combination therapy of chronic obstructive pulmonary disease and asthma," *Future Med. Chem.* 3(13):1703-1718, 2011.
Lechuga-Ballesteros, et al., "Dose Proportionality in a Triple Therapy Cosuspension pMDI with Multiple Strengths of an Inhaled Corticosteroid" *RDD Europe 2013—Respiratory Drug Delivery vol. 2*, pp. 339-342, published by Virginia Commonwealth University 2013.
Lechuga-Ballesteros, et al. "A New Co-Suspension MDI Platform: Scientific Foundations of Mono, Dual and Triple Combination Products" *RDD Europe 2011—Respiratory Drug Delivery vol. 1*, pp. 101-112, published by Virginia Commonwealth University 2011.
Joshi et al., "Development of Mono, Dual, and Triple Combination pMDIs without Co-formulation Effect" *RDD Europe 2011—Respiratory Drug Delivery vol. 2*, pp. 383-386, published by Virginia Commonwealth University 2011.
Noga et al., "Product Performance, Stability and Dose Proportionality of Glycopyrrolate Metered Dose Inhaler with Sub-Microgram Doses Using Cosuspension Technology" *RDD 2012 Arizona—Respiratory Drug Delivery vol. 2*, pp. 645-648, published by Virginia Commonwealth University 2012.
Vehring et al., "Cosuspensions of Microcrystals and Engineered Microparticles for Uniform and Efficient Delivery of Respiratory Therapeutics from Pressurized Metered Dose Inhalers," *Langmuir* 28:15015-15023, 2012.

\* cited by examiner

COMPOSITIONS, METHODS AND SYSTEMS FOR RESPIRATORY DELIVERY OF TWO OR MORE ACTIVE AGENTS

RELATED APPLICATIONS

This application is a continuation-in-part of U.S. application Ser. No. 12/790,710, filed on May 28, 2010, which claims the benefit of U.S. Provisional Application No. 61/182,565, filed May 29, 2009; U.S. Provisional Application No. 61/258,172, filed Nov. 4, 2009; U.S. Provisional Application No. 61/309,365, filed Mar. 1, 2010; and U.S. Provisional Application No. 61/345,536 filed May 17, 2010. This application hereby incorporates by reference the U.S. priority applications enumerated herein.

TECHNICAL FIELD

The present disclosure relates generally to compositions, methods and systems for respiratory delivery of two or more active agents. In certain embodiments, the present disclosure relates to compositions, methods, and systems for respiratory delivery of two or more active agents, wherein at least one of the active agents is selected from long-acting muscarinic antagonist ("LAMA"), long-acting $\beta_2$ adrenergic agonist ("LABA"), and corticosteroid active agents.

BACKGROUND

Methods of targeted drug delivery that deliver an active agent at the site of action are often desirable. For example, targeted delivery of active agents can reduce undesirable side effects, lower dosing requirements and decrease therapeutic costs. In the context of respiratory delivery, inhalers are well known devices for administering an active agent to a subject's respiratory tract, and several different inhaler systems are currently commercially available. Three common inhaler systems include dry powder inhalers, nebulizers and metered dose inhalers (MDIs).

MDIs may be used to deliver medicaments in a solubilized form or as a suspension. Typically, MDIs use a relatively high vapor pressure propellant to expel aerosolized droplets containing an active agent into the respiratory tract when the MDI is activated. Dry powder inhalers generally rely on the patient's inspiratory efforts to introduce a medicament in a dry powder form to the respiratory tract. On the other hand, nebulizers form a medicament aerosol to be inhaled by imparting energy to a liquid solution or suspension.

MDIs are active delivery devices that utilize the pressure generated by a propellant. Conventionally, chlorofluorocarbons (CFCs) have been used as propellants in MDI systems because of their low toxicity, desirable vapor pressure and suitability for formulation of stable suspensions. However, traditional CFC propellants are understood to have a negative environmental impact, which has led to the development of alternative propellants that are believed to be more environmentally-friendly, such as perfluorinated compounds (PFCs) and hydrofluoroalkanes (HFAs).

The active agent to be delivered by a suspension MDI is typically provided as a fine particulate dispersed within a propellant or combination of two or more propellants (i.e., a propellant "system"). In order to form the fine particulates, the active agent is typically micronized. Fine particles of active agent suspended in a propellant or propellant system tend to aggregate or flocculate rapidly. This is particularly true of active agents present in micronized form. In turn, aggregation or flocculation of these fine particles may complicate the delivery of the active agent. For example, aggregation or flocculation can lead to mechanical failures, such as those that might be caused by obstruction of the valve orifice of the aerosol container. Unwanted aggregation or flocculation of drug particles may also lead to rapid sedimentation or creaming of drug particles, and such behavior may result in inconsistent dose delivery, which can be particularly troublesome with highly potent, low dose medicaments. Another problem associated with such suspension MDI formulations relates to crystal growth of the drug during storage, resulting in a decrease over time of aerosol properties and delivered dose uniformity of such MDIs. More recently, solution approaches, such as those disclosed in U.S. Pat. No. 6,964,759, have been proposed for MDI formulations containing anticholinergics.

One approach to improve aerosol performance in dry powder inhalers has been to incorporate fine particle carrier particles, such as lactose. Use of such fine excipients has not been investigated to any great extent for MDIs. A recent report by Young et al., "The influence of micronized particulates on the aerosolization properties of pressurized metered dose inhalers"; Aerosol Science 40, pgs. 324-337 (2009), suggests that the use of such fine particle carriers in MDIs actually result in a decrease in aerosol performance.

In traditional CFC systems, when the active agent present in an MDI formulation is suspended in the propellant or propellant system, surfactants are often used to coat the surfaces of the active agent in order to minimize or prevent the problem of aggregation and maintain a substantially uniform dispersion. The use of surfactants in this manner is sometimes referred to as "stabilizing" the suspension. However, many surfactants that are soluble and thus effective in CFC systems are not effective in HFA and PFC propellant systems because such surfactants exhibit different solubility characteristics in non-CFC propellants.

BRIEF DESCRIPTION OF THE DRAWINGS

FIG. 11 is a graph that depicts the glycopyrrolate particle size distribution achieved by a dual co-suspension prepared according to the present description, which included microcrystalline glycopyrrolate active agent particles and microcrystalline formoterol fumarate active agent particles with two different particle size distributions (denoted "fine" and "coarse") or spray dried formoterol fumarate.

Figure 17:
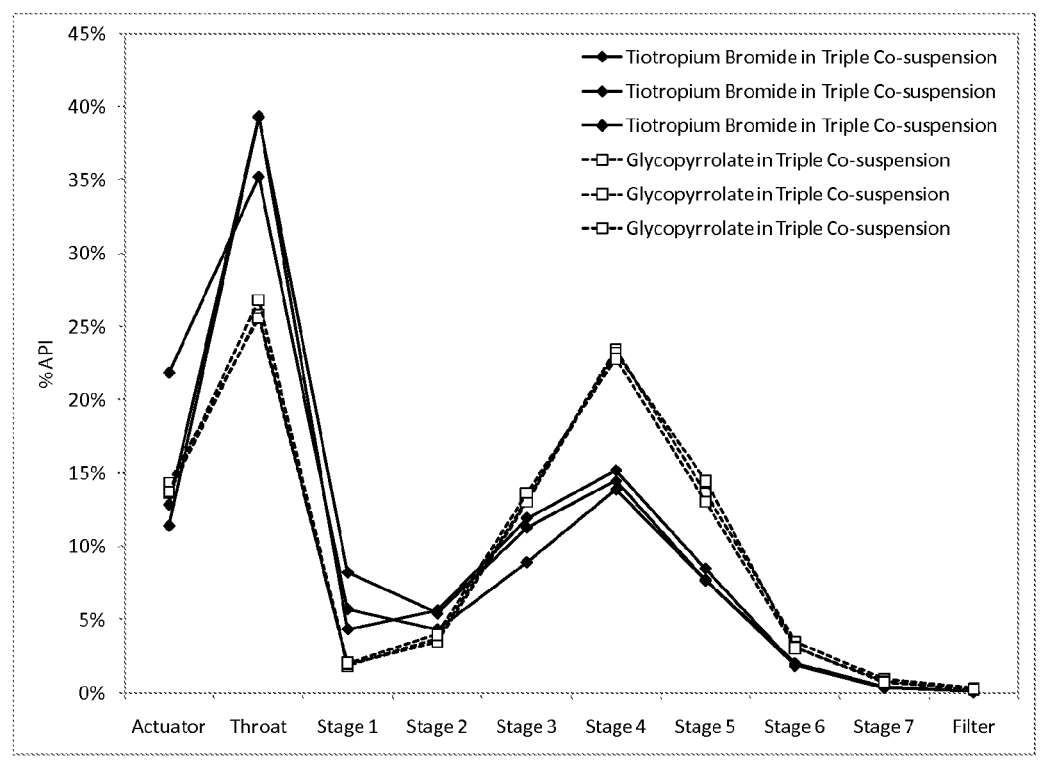

FIG. 17 is a graph depicting the glycopyrrolate and tiotropium bromide aerodynamic particle size distributions achieved by a triple co-suspension prepared according to the present description, which, in addition to either glycopyrrolate or tiotropium bromide active agent particles, included formoterol fumarate and mometasone furoate microcrystalline active agent particles.

DETAILED DESCRIPTION

Figure 1:
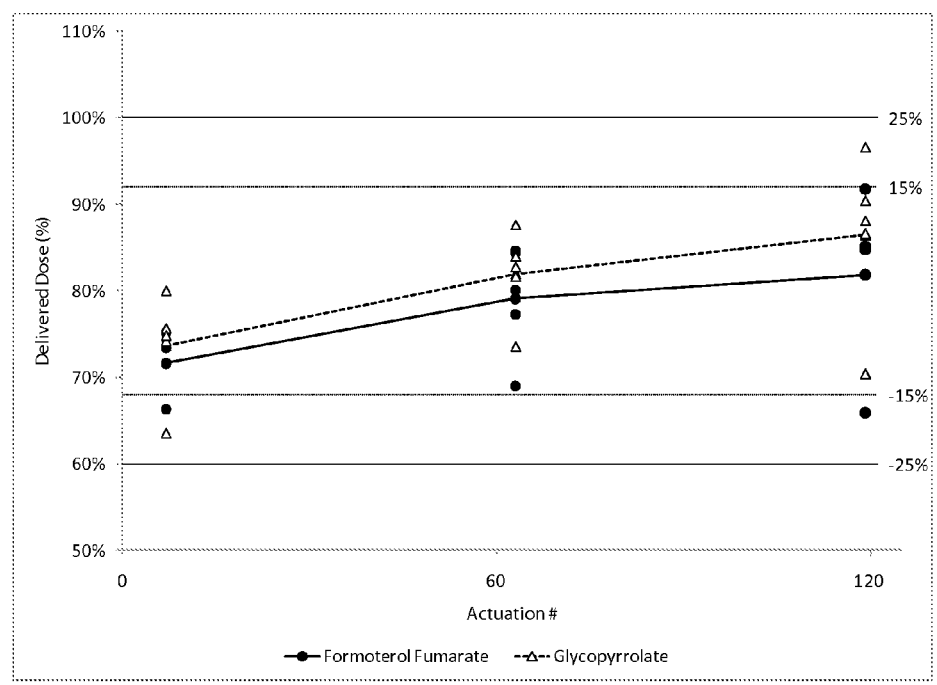
FIG. 1 is a graph, which depicts the delivered dose uniformity of a co-suspension formulation containing glycopyrrolate and formoterol fumarate prepared according to the present description.

The present disclosure provides compositions, methods, and systems for respiratory delivery of two or more active agents. Specifically, in certain embodiments, the present disclosure includes pharmaceutical compositions, systems and methods for respiratory delivery of two or more active agents via an MDI, and in particular embodiments at least one of the active agents is selected from long-acting muscarinic antagonist ("LAMA"), long-acting $\beta_2$ adrenergic agonist ("LABA"), and corticosteroid active agents. The compositions described herein may be formulated for pulmonary or nasal delivery via an MDI. The methods described herein include methods of stabilizing formulations including two or more active agents for respiratory delivery, as well as methods for pulmonary delivery of two or more active agents for treating a pulmonary disease or disorder via an MDI. Also described herein are MDI systems for delivery of two or more active agents, as well as methods for preparing such systems.

Formulating pharmaceutical compositions incorporating two or more active agents is often challenging due to unpredictable or unexpected interactions between the active agents or changes to the formulations resulting from the incorporation of multiple active agents. Such interactions are generally known as a "combination effect," and in the context of suspension formulations delivered from an MDI, a combination effect may be manifest by, for example, a deviation from similarity between a formulation including a single active agent and a formulation including a combination of two or more active agents in one or more of the following areas: the aerosol and particle size distribution characteristics provided by the formulation; delivered dose uniformity for one or more of the active agents; deliverability or absorption of one or more of the active agents; or the dose proportionality observed for one or more of the active agents.

In specific embodiments, the co-suspension compositions described herein avoid combination effects associated with combination formulations. For purposes of the present description, a composition avoids combination affects where, for a selected active agent, the aerosol properties, particle size distribution characteristics, and delivered dose uniformity achieved by a combination formulation do not deviate from those achieved by a comparable formulation wherein the only active agent is the selected active agent. In some embodiments, the lack of a combination effect is evidenced for a selected active agent where the plasma concentration over time for a targeted dose of the selected active agent delivered from a combination formulation does not deviate from the plasma concentration over time achieved when the selected active agent is delivered at the same dose from a comparable formulation wherein the only active agent is the selected active agent.

As used herein, the phrases "do not deviate" or "does not deviate" signify that, for a given parameter, the performance achieved by a combination formulation is ±20% of that achieved by a comparable formulation including only one of the active agents included in the combination formulation. In certain embodiments, the performance achieved by a combination formulation does not vary from that achieved by a comparable formulation including only one of the active agents included in the combination. For example, a co-suspension as described herein, including two or more active agents, is considered to exhibit no combination effect when, with respect to each such active agent at a given dose, one or more of the aerosol properties, the particle size distribution characteristics, the delivered dose uniformity, and the plasma concentration over time achieved by the combination co-suspension are within ±20% of those achieved by a comparable formulation including only a single active agent. In some embodiments, for each active agent at a give dose, one or more of the aerosol properties, the particle size distribution characteristics, the delivered dose uniformity, and the plasma concentration over time achieved by the combination co-suspension compositions described herein are within ±15% of those achieved by a comparable formulation including only a single active agent. In yet other embodiments, for each active agent at a give dose, one or more of the aerosol properties, the particle size distribution characteristics, the delivered dose uniformity, and the plasma concentration over time achieved by the combination co-suspension compositions described herein are within ±10% of those achieved by a comparable formulation including only a single active agent. In certain embodiments, with respect to each active agent at a given dose, the combination co-suspension compositions as described herein exhibit no difference to comparable formulations including only one of the active agents included in the combination in one or more of the following areas: aerosol properties for the formulation; the particle size distribution characteristics; delivered dose uniformity for; and the plasma concentration over time.

The combination of two or more active agents included in the compositions provided herein may, in some embodiments, provide advantages over pharmaceutical formulations including only a single active agent. For instance, when a combination of two or more active agents is delivered simultaneously, the therapeutically effective dose of both active agents may be relatively less than when any of the combined active agents is delivered alone, thereby avoiding or reducing possible side effects. Moreover, combinations of two or more active agents may achieve a more rapid onset or longer duration of therapeutic benefit than can be achieved by delivering one of the combined active agents alone.

In specific embodiments, the methods described herein include methods for treating a pulmonary disease or disorder amenable to treatment by respiratory delivery of a co-suspension composition as described herein. For example, the compositions, methods and systems described herein can be used to treat inflammatory or obstructive pulmonary diseases or conditions. In certain embodiments, the compositions, methods and systems described herein can be used to treat patients suffering from a disease or disorder selected from asthma, chronic obstructive pulmonary disease (COPD), exacerbation of airways hyper reactivity consequent to other drug therapy, allergic rhinitis, sinusitis, pulmonary vasoconstriction, inflammation, allergies, impeded respiration, respiratory distress syndrome, pulmonary hypertension, pulmonary vasoconstriction, and any other respiratory disease, condition, trait, genotype or phenotype that can respond to the administration of, for example, a LAMA, LABA, corticosteroid, or other active agent as described herein, whether alone or in combination with other therapies. In certain embodiments, the compositions, systems and methods described herein can be used to treat pulmonary inflammation and obstruction associated with cystic fibrosis. As used herein, the terms "COPD" and "chronic obstructive pulmonary disease" encompass chronic obstructive lung disease (COLD), chronic obstructive airway disease (COAD), chronic airflow limitation (CAL) and chronic obstructive respiratory disease (CORD) and include chronic bronchitis, bronchiectasis, and emphysema. As used herein, the term "asthma" refers to asthma of whatever type or genesis, including intrinsic (non-allergic) asthma and extrinsic (allergic) asthma, mild asthma, moderate asthma, severe asthma, bronchitic asthma, exercise-induced asthma, occupational asthma and asthma induced following bacterial infection. Asthma is also to be understood as embracing wheezy-infant syndrome.

When administered to patients suffering from pulmonary disease, embodiments of the co-suspension compositions described herein provide a significant increase in one or more measures of lung function or capacity when compared to compositions delivering only a single active agent. In certain such embodiments, the delivery of a co-suspension composition as described herein including two or more active agents results in a significant increase in one or both of $FEV_1$ and inspiratory capacity (IC) relative to composition containing only a single active agent.

It will be readily understood that the embodiments, as generally described herein, are exemplary. The following more detailed description of various embodiments is not intended to limit the scope of the present disclosure, but is merely representative of various embodiments. As such, the specifics recited herein may include independently patentable subject matter. Moreover, the order of the steps or actions of the methods described in connection with the embodiments disclosed herein may be changed by those skilled in the art without departing from the scope of the present disclosure. In other words, unless a specific order of steps or actions is required for proper operation of the embodiment, the order or use of specific steps or actions may be modified.

I. Definitions

Unless specifically defined otherwise, the technical terms, as used herein, have their normal meaning as understood in the art. The following terms are specifically defined for the sake of clarity.

The term "active agent" is used herein to include any agent, drug, compound, composition or other substance that may be used on, or administered to a human or animal for any purpose, including therapeutic, pharmaceutical, pharmacological, diagnostic, cosmetic and prophylactic agents and immunomodulators. The term "active agent" may be used interchangeably with the terms, "drug," "pharmaceutical," "medicament," "drug substance," or "therapeutic." As used herein the "active agent" may also encompass natural or homeopathic products that are not generally considered therapeutic.

The terms "associate," "associate with" or "association" refers to an interaction or relationship between a chemical entity, composition, or structure in a condition of proximity to a surface, such as the surface of another chemical entity, composition, or structure. The association includes, for example, adsorption, adhesion, covalent bonding, hydrogen bonding, ionic bonding and electrostatic attraction, Lifshitz-van der Waals interactions and polar interactions. The term "adhere" or "adhesion" is a form of association and is used as a generic term for all forces tending to cause a particle or mass to be attracted to a surface. "Adhere" also refers to bringing and keeping particles in contact with each other, such that there is substantially no visible separation between particles due to their different buoyancies in a propellant under normal conditions. In one embodiment, a particle that attaches to or binds to a surface is encompassed by the term "adhere." Normal conditions may include storage at room temperature or under an accelerative force due to gravity. As described herein, active agent particles may associate with suspending particles to form a co-suspension, where there is substantially no visible separation between the suspending particles and the active agent particles or flocculates thereof due to differences in buoyancy within a propellant.

"Suspending particles" refer to a material or combination of materials that is acceptable for respiratory delivery, and acts as a vehicle for active agent particles. Suspending particles interact with the active agent particles to facilitate repeatable dosing, delivery or transport of active agent to the target site of delivery, i.e., the respiratory tract. The suspending particles described herein are dispersed within a suspension medium including a propellant or propellant system, and can be configured according to any shape, size or surface characteristic suited to achieving a desired suspension stability or active agent delivery performance. Exemplary suspending particles include particles that exhibit a particle size that facilitates respiratory delivery of active agent and have physical configurations suited to formulation and delivery of the stabilized suspensions as described herein.

The term "co-suspension" refers to a suspension of two or more types of particles having different compositions within a suspension medium, wherein one type of particle associates at least partially with one or more of the other particle types. The association leads to an observable change in one or more characteristics of at least one of the individual particle types suspended in the suspension medium. Characteristics modified by the association may include, for example, one or more of the rate of aggregation or flocculation, the rate and nature of separation, i.e. sedimentation or creaming, density of a cream or sediment layer, adhesion to container walls, adhesion to valve components, and rate and the level of dispersion upon agitation.

Exemplary methods for assessing whether a co-suspension is present can include the following: If one particle type has a pycnometric density greater than the propellant and another particle type has a pycnometric density lower than the propellant, a visual observation of the creaming or sedimentation behavior can be employed to determine the presence of a co-suspension. The term "pycnometric density" refers to the density of a material that makes up a particle, excluding voids within the particle. In one embodiment, the materials can be formulated or transferred into a transparent vial, typically a glass vial, for visual observation. After initial agitation the vial is left undisturbed for a sufficient time for formation of a sediment or cream layer, typically 24 hours. If the sediment or cream layer is observed to be completely or mostly a uniform single layer, a co-suspension is present. The term "co-suspension" includes partial co-suspensions, where a majority of the at least two particle types associate with each other, however, some separation (i.e., less than a majority) of the at least two particle types may be observed.

The exemplary co-suspension test may be performed at different propellant temperatures to accentuate the sedimentation or creaming behavior of particle types with a density close to the propellant density at room temperature. If the different particle types have the same nature of separation, i.e. all sediment or all cream, the presence of a co-suspension can be determined by measuring other characteristics of the suspension, such as rate of aggregation or flocculation, rate of separation, density of cream or sediment layer, adhesion to container walls, adhesion to valve components, and rate and level of dispersion upon agitation, and comparing them to the respective characteristics of the similarly suspended individual particle types. Various analytical methods generally known to those skilled in the art can be employed to measure these characteristics.

In the context of a composition containing or providing respirable aggregates, particles, drops, etc., such as compositions described herein, the term "fine particle dose" or "FPD" refers to the dose, either in total mass or fraction of the nominal dose or metered dose, that is within a respirable range. The dose that is within the respirable range is measured in vitro to be the dose that deposits beyond the throat stage of a cascade impactor, i.e., the sum of dose delivered at stages 3 through filter in a Next Generation Impactor operated at a flow rate of 30 l/min.

In the context of a composition containing or providing respirable aggregates, particles, drops, etc., such as compositions described herein, the term "fine particle fraction" or "FPF" refers to the proportion of the delivered material relative to the delivered dose (i.e., the amount that exits the actuator of a delivery device, such as an MDI) that is within a respirable range. The amount of delivered material within the respirable range is measured in vitro as the amount of material that deposits beyond the throat stage of a cascade impactor, e.g., the sum of the material delivered at stages 3 through filter in a Next Generation Impactor operated at a flow rate of 30 l/min.

As used herein, the term "inhibit" refers to a measurable lessening of the tendency of a phenomenon, symptom or condition to occur or the degree to which that phenomenon, symptom or condition occurs. The term "inhibit" or any form thereof, is used in its broadest sense and includes minimize, prevent, reduce, repress, suppress, curb, constrain, restrict, slow progress of and the like.

"Mass median aerodynamic diameter" or "MMAD" as used herein refers to the aerodynamic diameter of an aerosol below which 50% of the mass of the aerosol consists of particles with an aerodynamic diameter smaller than the MMAD, with the MMAD being calculated according to monograph 601 of the United States Pharmacopeia ("USP").

When referred to herein, the term "optical diameter" indicates the size of a particle as measured by the Fraunhofer diffraction mode using a laser diffraction particle size analyzer equipped with a dry powder dispenser (e.g., Sympatec GmbH, Clausthal-Zellerfeld, Germany).

The term solution mediated transformation refers to the phenomenon in which a more soluble form of a solid material (i.e. particles with small radius of curvature (a driving force for Ostwald ripening), or amorphous material) dissolves and recrystallizes into the more stable crystal form that can coexist in equilibrium with its saturated propellant solution.

A "patient" refers to an animal in which a combination of active agents as described herein will have a therapeutic effect. In one embodiment, the patient is a human being.

"Perforated microstructures" refer to suspending particles that include a structural matrix that exhibits, defines or comprises voids, pores, defects, hollows, spaces, interstitial spaces, apertures, perforations or holes that allow the surrounding suspension medium to permeate, fill or pervade the microstructure, such as those materials and preparations described in U.S. Pat. No. 6,309,623 to Weers, et al. The primary form of the perforated microstructure is, generally, not essential, and any overall configuration that provides the desired formulation characteristics is contemplated herein. Accordingly, in one embodiment, the perforated microstructures may comprise approximately spherical shapes, such as hollow, suspending, spray-dried microspheres. However, collapsed, corrugated, deformed or fractured particulates of any primary form or aspect ratio may also be compatible.

As is true of suspending particles described herein, perforated microstructures may be formed of any biocompatible material that does not substantially degrade or dissolve in the selected suspension medium. While a wide variety of materials may be used to form the particles, in some embodiments, the structural matrix is associated with, or includes, a surfactant such as, a phospholipid or fluorinated surfactant. Although not required, the incorporation of a compatible surfactant in the perforated microstructure or, more generally, the suspending particles, can improve the stability of the respiratory dispersions, increase pulmonary deposition and facilitate the preparation of the suspension.

The term "suspension medium" as used herein refers to a substance providing a continuous phase within which active agent particles and suspending particles can be dispersed to provide a co-suspension formulation. The suspension medium used in co-suspension formulations described herein includes propellant. As used herein, the term "propellant" refers to one or more pharmacologically inert substances which exert a sufficiently high vapor pressure at normal room temperature to propel a medicament from the canister of an MDI to a patient on actuation of the MDI's metering valve. Therefore, the term "propellant" refers to both a single propellant and to a combination of two or more different propellants forming a "propellant system."

The term "respirable" generally refers to particles, aggregates, drops, etc. sized such that they can be inhaled and reach the airways of the lung.

When used to refer to co-suspension compositions described herein, the terms "physical stability" and "physically stable" refer to a composition that is resistant to one or more of aggregation, flocculation, and particle size changes due to solution mediated transformations and is capable of substantially maintaining the MMAD of suspending particles and the fine particle dose. In one embodiment, physical stability may be evaluated through subjecting compositions to accelerated degradation conditions, such as by temperature cycling as described herein.

When referring to active agents, the term "potent" indicates active agents that are therapeutically effective at or below doses ranging from about 0.01 mg/kg to about 1 mg/kg.

Typical doses of potent active agents generally range from about 100 μg to about 100 mg.

When referring to active agents, the term "highly potent" indicates active agents that are therapeutically effective at or below doses of about 10 μg/kg. Typical doses of highly potent active agents generally range up to about 100 μg.

The terms "suspension stability" and "stable suspension" refer to suspension formulations capable of maintaining the properties of a co-suspension of active agent particles and suspending particles over a period of time. In one embodiment, suspension stability may be measured through delivered dose uniformity achieved by co-suspension compositions described herein.

The term "substantially insoluble" means that a composition is either totally insoluble in a particular solvent or it is poorly soluble in that particular solvent. The term "substantially insoluble" means that a particular solute has a solubility of less than one part per 100 parts solvent. The term "substantially insoluble" includes the definitions of "slightly soluble" (from 100 to 1000 parts solvent per 1 part solute), "very slightly soluble" (from 1000 to 10,000 parts solvent per 1 part solute) and "practically insoluble" (more than 10,000 parts solvent per 1 part solute) as given in Table 16-1 of Remington: The Science and Practice of Pharmacy, 21st ed. Lippincott, Williams & Wilkins, 2006, p. 212.

The term "surfactant," as used herein, refers to any agent which preferentially adsorbs to an interface between two immiscible phases, such as the interface between water and an organic polymer solution, a water/air interface or organic solvent/air interface. Surfactants generally possess a hydrophilic moiety and a lipophilic moiety, such that, upon adsorbing to microparticles, they tend to present moieties to the continuous phase that do not attract similarly-coated particles, thus reducing particle agglomeration. In some embodiments, surfactants may also promote adsorption of a drug and increase bioavailability of the drug.

A "therapeutically effective amount" is the amount of compound which achieves a therapeutic effect by inhibiting a disease or disorder in a patient or by prophylactically inhibiting or preventing the onset of a disease or disorder. A therapeutically effective amount may be an amount which relieves to some extent one or more symptoms of a disease or disorder in a patient; returns to normal either partially or completely one or more physiological or biochemical parameters associated with or causative of the disease or disorder; and/or reduces the likelihood of the onset of the disease of disorder.

The terms "chemically stable" and "chemical stability" refer to co-suspension formulations wherein the individual degradation products of active agent remain below the limits specified by regulatory requirements during the shelf life of the product for human use (e.g., 1% of total chromatographic peak area per ICH guidance Q3B(R2)) and there is acceptable mass balance (e.g., as defined in ICH guidance Q1E) between active agent assay and total degradation products.

II. Compositions

The compositions described herein are co-suspensions that include two or more active agents and include a suspension medium, one or more species of active agent particles, and one or more species of suspending particles. Of course, if desired, the compositions described herein may include one or more additional constituents. Moreover, variations and combinations of components of the compositions described herein may be used.

The co-suspension compositions according to the present description can be embodied by various different formulations. In certain embodiments, the compositions described herein include a first active agent provided in active agent particles that are co-suspended with at least one species of suspending particles that incorporate a second active agent. In other embodiments, the compositions described herein include two or more active agents provided in two or more different species of active agent particles co-suspended with at least one species of suspending particles that incorporate an active agent different from that contained in any of the active agent particles. In yet further embodiments, the compositions described herein include two or more active agents provided in two or more different species of active agent particles co-suspended with at least one species of suspending particles that incorporate an active agent that may be the same as or different from that contained in any of the active agent particles. In still further embodiments, the compositions described herein include two or more active agents provided in two or more different species of active agent particles co-suspended with one or more species of suspending particles that are free of active agent. Where the compositions described herein include two or more species of active agent particles, such compositions may be referred to as "multi" co-suspensions. For example, a composition including two species of active agent particles co-suspended with one or more species of suspending particles may be referred to as a dual co-suspension, a composition including three species of active agent particles co-suspended with one or more species of suspending particles may be referred to as a triple co-suspension, etc.

In compositions according to the present description, even when multiple different species of active agent particles are present in the composition, the active agent particles exhibit an association with the suspending particles such that the active agent particles and suspending particles co-locate within the suspension medium. Generally, due to density differences between distinct species of particles and the medium within which they are suspended (e.g., a propellant or propellant system), buoyancy forces cause creaming of particles with lower density than the propellant and sedimentation of particles with higher density than the propellant. Therefore, in suspensions that consist of a mixture of different types of particles with different density or different tendencies to flocculate, sedimentation or creaming behavior is expected to be specific to each of the different particle types and expected to lead to separation of the different particle types within the suspension medium.

However, the combinations of propellant, active agent particles, and suspending particles described herein provide co-suspensions including combinations of two or more active agents wherein the active agent particles and suspending particles co-locate within the propellant (i.e., the active agent particles associate with the suspending particles such that suspending particles and active agent particles do not exhibit substantial separation relative to each other, such as by differential sedimentation or creaming, even after a time sufficient for the formation of a cream or sediment layer). In particular embodiments, for example, the compositions described herein form co-suspensions wherein the suspending particles remain associated with active agent particles when subjected to buoyancy forces amplified by temperature fluctuations and/or centrifugation at accelerations up to and over, for example, 1 g, 10 g, 35 g, 50 g, and 100 g. However, the co-suspensions described herein need not be defined by a specific threshold force of association. For example, a co-suspension as contemplated herein may be successfully achieved where the active agent particles associate with the suspending particles such that there is no substantial separation of active agent particles and suspending particles within the continuous phase formed by the suspension medium under typical patient use conditions.

Co-suspensions of active agent particles and suspending particles according to the present description provide desirable chemical stability, suspension stability and active agent delivery characteristics. For example, in certain embodiments, when present within an MDI canister, co-suspensions as described herein can inhibit one or more of the following: flocculation of active agent material; differential sedimentation or creaming of active agent particles and suspending particles; solution mediated transformation of active agent material; chemical degradation of a component of the formulation, including of active agent material or a surfactant; and loss of active agent to the surfaces of the container closure system, in particular the metering valve components. Such qualities work to achieve and preserve aerosol performance as the co-suspension formulation is delivered from an MDI such that desirable fine particle fraction, fine particle dose and delivered dose uniformity characteristics are achieved and substantially maintained throughout emptying of an MDI canister within which the co-suspension formulation is contained. Additionally, co-suspensions according to the present description can provide a physically and chemically stable formulation that provides consistent dosing characteristics for two or more active agents, even where such active agents are delivered at significantly different doses, while utilizing a relatively simple HFA suspension medium that does not require modification by the addition of, for example, cosolvents, antisolvents, solubilizing agents or adjuvants. Even further, compositions prepared as described herein, when delivered from an MDI, eliminate or substantially avoid the pharmaceutical effects often experienced with formulations including multiple active agents. For example, as exemplified by specific embodiments detailed herein, the combination formulations described herein provide delivery characteristics for each of the active agents contained therein comparable to delivery characteristics of the same active agents when formulated and delivered separately.

Providing a co-suspension according to the present description may also simplify formulation, delivery and dosing of the desired active agents. Without being bound by a particular theory, it is thought that by achieving a co-suspension of active agent particles and suspending particles, the delivery, physical stability, and dosing of an active agent contained within such a dispersion may be substantially controlled through control of the size, composition, morphology and relative amount of the suspending particles, and is less dependent upon the size and morphology of the particles of active agent. Moreover, in specific embodiments, the pharmaceutical compositions described herein can be formulated with a non-CFC propellant or propellant system substantially free of antisolvents, solubilizing agents, cosolvents, or adjuvants.

Co-suspension compositions formulated according to the present teachings can inhibit physical and chemical degradation of the active agents included therein. For example, in specific embodiments, the compositions described herein may inhibit one or more of chemical degradation, flocculation, aggregation and solution mediated transformation of the active agents included in the compositions. The chemical and suspension stability provided by the co-suspension compositions described herein allows the compositions to be dispensed in a manner that achieves desirable delivered dose uniformity throughout emptying of an MDI canister ("DDU") for multiple active agents, even where at least one of the active agents to be delivered may be highly potent and the delivered doses of each of the active agents vary considerably.

Co-suspension compositions as described herein, which include two or more active agents, can achieve a DDU of ±30%, or better for each of the active agents included therein. In one such embodiment, compositions described herein achieve a DDU of ±25%, or better, for each of the active agents included therein. In another such embodiment, compositions described herein achieve a DDU of ±20%, or better, for each of the active agents included therein. Moreover, co-suspension compositions according to the present description serve to substantially preserve FPF and FPD performance throughout emptying of an MDI canister, even after being subjected to accelerated degradation conditions. For instance, compositions according to the present description maintain as much as 80%, 90%, 95%, or more, of the original FPF or FPD performance, even after being subjected to accelerated degradation conditions.

Co-suspension compositions described herein provide the added benefit of achieving such performance while being formulated using non-CFC propellants. In specific embodiments, the compositions described herein achieve one or more of a targeted DDU, FPF or FPD, while being formulated with suspension medium including only one or more non-CFC propellants and without the need to modify the characteristics of the non-CFC propellant, such as by the addition of, for example, one or more cosolvent, antisolvent, solubilizing agent, adjuvant or other propellant modifying material.

(i) Suspension Medium

The suspension medium included in a composition described herein includes one or more propellants. In general, suitable propellants for use as suspension mediums are those propellant gases that can be liquefied under pressure at room temperature, and upon inhalation or topical use, are safe and toxicologically innocuous. Additionally, it is desirable that the selected propellant be relatively non-reactive with the suspending particles and active agent particles. Exemplary compatible propellants include hydrofluoroalkanes (HFAs), perfluorinated compounds (PFCs), and chlorofluorocarbons (CFCs).

Specific examples of propellants that may be used to form the suspension medium of the co-suspensions disclosed herein include 1,1,1,2-tetrafluoroethane ($CF_3CH_2F$) (HFA-134a), 1,1,1,2,3,3,3-heptafluoro-n-propane ($CF_3CHFCF_3$) (HFA-227), perfluoroethane, monochloro-fluoromethane, 1,1 difluoroethane, and combinations thereof. Even further, suitable propellants include, for example: short chain hydrocarbons; $C_{1-4}$ hydrogen-containing chlorofluorocarbons such as $CH_2ClF$, $CCl_2FCHClF$, $CF_3CHClF$, $CHF_2CClF_2$, $CHClFCHF_2$, $CF_3CH_2Cl$, and $CClF_2CH_3$; $C_{1-4}$ hydrogen-containing fluorocarbons (e.g., HFAs) such as $CHF_2CHF_2$, $CF_3CH_2F$, $CHF_2CH_3$, and $CF_3CHFCF_3$; and perfluorocarbons such as $CF_3CF_3$ and $CF_3CF_2CF_3$.

Specific fluorocarbons, or classes of fluorinated compounds, that may be used as suspension media include, but are not limited to, fluoroheptane, fluorocycloheptane, fluoromethylcycloheptane, fluorohexane, fluorocyclohexane, fluoropentane, fluorocyclopentane, fluoromethylcyclopentane, fluorodimethyl-cyclopentanes, fluoromethylcyclobutane, fluorodimethylcyclobutane, fluorotrimethyl-cyclobutane, fluorobutane, fluorocyclobutane, fluoropropane, fluoroethers, fluoropolyethers and fluorotriethylamines. These compounds may be used alone or in combination with more volatile propellants.

In addition to the aforementioned fluorocarbons and hydrofluoroalkanes, various exemplary chlorofluorocarbons and substituted fluorinated compounds may also be used as suspension media. In this respect, FC-11 ($CCl_3F$), FC-11B1 ($CBrCl_2F$), FC-11B2 ($CBr_2ClF$), FC12B2 ($CF_2Br_2$), FC21

(CHCl$_2$F), FC21B1 (CHBrClF), FC-21B2 (CHBr$_2$F), FC-31B1 (CH$_2$BrF), FC113A (CCl$_3$CF$_3$), FC-122 (CClF$_2$CHCl$_2$), FC-123 (CF$_3$CHCl$_2$), FC-132 (CHClFCH-ClF), FC-133 (CHClFCHF$_2$), FC-141 (CH$_2$ClCHClF), FC-141B (CCl$_2$FCH$_3$), FC-142 (CHF$_2$CH$_2$Cl), FC-151 (CH$_2$FCH$_2$Cl), FC-152 (CH$_2$FCH$_2$F), FC-1112 (CClF=CClF), FC-1121 (CHCl=CFCl) and FC-1131 (CHCl=CHF) may also be used, while recognizing the possible attendant environmental concerns. As such, each of these compounds may be used, alone or in combination with other compounds (i.e., less volatile fluorocarbons) to form the stabilized suspensions disclosed herein.

In some embodiments, the suspension medium may be formed of a single propellant. In other embodiments, a combination of propellants may be used to form the suspension medium. In some embodiments, relatively volatile compounds may be mixed with lower vapor pressure components to provide suspension media having specified physical characteristics selected to improve stability or enhance the bioavailability of the dispersed active agents. In some embodiments, the lower vapor pressure compounds will comprise fluorinated compounds (e.g. fluorocarbons) having a boiling point greater than about 25° C. In some embodiments, lower vapor pressure fluorinated compounds for use in the suspension medium may include perfluorooctylbromide C$_8$F$_{17}$Br (PFOB or perflubron), dichlorofluorooctane C$_8$F$_{16}$Cl$_2$, perfluorooctylethane C$_8$F$_{17}$C$_2$H$_5$ (PFOE), perfluorodecylbromide C$_{10}$F$_{21}$Br (PFDB) or perfluorobutylethane C$_4$F$_9$C$_2$H$_5$. In certain embodiments, these lower vapor pressure compounds are present in a relatively low level. Such compounds may be added directly to the suspension medium or may be associated with the suspending particles.

The suspension medium included in compositions as described herein may be formed of a propellant or propellant system that is substantially free of additional materials, including, for example, antisolvents, solubilizing agents, cosolvents or adjuvants. For example, in some embodiments, the suspension medium may be formed of a non-CFC propellant or propellant system, such as an HFA propellant or propellant system, that is substantially free of additional materials. Such embodiments simplify the formulation and manufacture of pharmaceutical compositions suited for respiratory delivery of the active agents included in the co-suspension compositions.

However, in other embodiments, depending on the selection of propellant, the properties of the suspending particles, or the nature of the active agents to be delivered, the suspension medium utilized may include materials in addition to the propellant or propellant system. Such additional materials may include, for example, one or more of an appropriate antisolvent, solubilizing agent, cosolvent or adjuvant to adjust, for example, the vapor pressure of the formulation or the stability, or solubility of suspended particles. For example, propane, ethanol, isopropyl alcohol, butane, isobutane, pentane, isopentane or a dialkyl ether, such as dimethyl ether, may be incorporated with the propellant in the suspension medium. Similarly, the suspension medium may contain a volatile fluorocarbon. In other embodiments, one or both of polyvinylpyrrolidone ("PVP") or polyethylene glycol ("PEG") may be added to the suspension medium. Adding PVP or PEG to the suspension medium may achieve one or more desired functional characteristics, and in one example, PVP or PEG may be added to the suspension medium as a crystal growth inhibitor. In general, where a volatile cosolvent or adjuvant is used, such an adjuvant or cosolvent may be selected from known hydrocarbon or fluorocarbon materials and may account for up to about 1% w/w of the suspension medium. For example, where a cosolvent or adjuvant is incorporated in the suspension medium, the cosolvent or adjuvant may comprise less than about 0.01%, 0.1%, or 0.5% w/w of the suspension medium. Where PVP or PEG are included in the suspension medium, such constituents may be included at up to about 1% w/w, or they may comprise less than about 0.01%, 0.1%, or 0.5% w/w of the suspension medium.

(ii) Active Agent Particles

The active agent particles included in the co-suspensions described herein are formed of a material capable of being dispersed and suspended within the suspension medium and are sized to facilitate delivery of respirable particles from the co-suspension. In one embodiment, therefore, the active agent particles are provided as a micronized material wherein at least 90% of the active agent particles by volume exhibit an optical diameter of about 7 μm or less. In other embodiments, the active agent particles are provided as a micronized material wherein at least 90% of the active agent particles by volume exhibit an optical diameter selected from a range of about 7 μm to about 1 μm, about 5 μm to about 2 μm, and about 3 μm to about 2 μm. In other embodiments, the active agent particles are provided as a micronized material wherein at least 90% of the active agent particles by volume exhibit an optical diameter selected from 6 μm or less, 5 μm or less, 4 μm or less, or 3 μm or less. In another embodiment, the active agent particles are provided as a micronized material wherein at least 50% of the active agent particle material by volume exhibits an optical diameter of about 4 μm or less. In further embodiments, the active agent particles are provided as a micronized material wherein at least 50% of the active agent particle material by volume exhibits an optical diameter selected from about 3 μm or less, about 2 μm or less, about 1.5 μm or less, and about 1 μm or less. In still further embodiments, the active agent particles are provided as a micronized material wherein at least 50% of the active agent particles by volume exhibit an optical diameter selected from a range of about 4 μm to about 1 μm, about 3 μm to about 1 μm, about 2 μm to about 1 μm, about 1.3 μm, and about 1.9 μm.

The active agent particles may be formed entirely of active agent or they may be formulated to include one or more active agents in combination with one or more excipients or adjuvants. In specific embodiments, an active agent present in the active agent particles may be entirely or substantially crystalline, i.e., a majority of the active agent molecules are arranged in a regularly repeating pattern, over a long range of external face planes. In another embodiment, the active agent particles may include an active agent present in both crystal and amorphous states. In yet another embodiment, the active agent particles may include an active agent present in substantially an amorphous state, i.e., the active agent molecules are overall noncrystalline in nature and do not have a regularly repeating arrangement maintained over a long range. In yet a further embodiment, where two or more active agents are present as active agent particles, all such active agents may be present in crystalline or substantially crystalline form. In alternative embodiments with two or more active agents present, at least one such active agent may be present in crystalline or substantially crystalline form and at least another active agent may be present in an amorphous state.

Where the active agent particles described herein include two or more active agents in combination with one or more excipients or adjuvants, the excipients and adjuvants can be selected based on the chemical and physical properties of the active agents used. Moreover, suitable excipients for the formulation of active agent particles include those described herein in association with the suspending particles. In specific embodiments, for example, active agent particles may be formulated with one or more of the lipid, phospholipid, carbohydrate, amino acid, organic salt, peptide, protein, alditols, synthetic or natural polymer, or surfactant materials as described, for example, in association with the suspending particles.

In other embodiments, for example, an active agent may be added to a solution of one or more of the lipid, phospholipid, carbohydrate, amino acid, metal salt, organic salt, peptide, protein, alditols, synthetic or natural polymer, or surfactant materials and spray-dried into a suspending particle that contains the active agent within the material forming the suspending particle.

Any suitable process may be employed to achieve micronized active agent material for use as or inclusion in active agent particles or suspending particles as described herein. Such processes include, but are not limited to, micronization by milling or grinding processes, crystallization or recrystallization processes, and processes using precipitation from supercritical or near-supercritical solvents, spray drying, spray freeze-drying, or lyophilization. Patent references teaching suitable methods for obtaining micronized active agent particles are described, for example, in U.S. Pat. No. 6,063,138, U.S. Pat. No. 5,858,410, U.S. Pat. No. 5,851,453, U.S. Pat. No. 5,833,891, U.S. Pat. No. 5,707,634, and International Patent Publication No. WO 2007/009164. Where the active agent particles include active agent material formulated with one or more excipient or adjuvant, micronized active agent particles can be formed using one or more of the preceding processes and such processes can be utilized to achieve active agent particles having a desired size distribution and particle configuration.

The active agent particles may be provided in any suitable concentration within the suspension medium. For example, in some embodiments, the active agent particles may be present in concentrations between about 0.01 mg/ml and about 20 mg/ml. In certain such embodiments, the active agent particles may be present in a concentration selected from about 0.05 mg/ml to about 20 mg/ml, about 0.05 mg/ml to about 10 mg/ml, and from about 0.05 mg/ml to about 5 mg/ml.

A variety of therapeutic or prophylactic agents can be utilized as active in the co-suspension compositions disclosed herein. Exemplary active agents include those that may be administered in the form of aerosolized medicaments, and active agents suitable for use in the compositions described herein include those that may be presented in a form or formulated in a manner which is dispersible within the selected suspension medium (e.g., is substantially insoluble or exhibits a solubility in the suspension medium that substantially maintains a co-suspension formulation), is capable of forming a co-suspension with the suspending particles, and is subject to respirable uptake in physiologically effective amounts. The active agents that may be utilized in forming the active agent particles described herein can have a variety of biological activities.

Examples of specific active agents that may be included in a composition according to the present description may for example, short-acting beta agonists, e.g., bitolterol, carbuterol, fenoterol, hexoprenaline, isoprenaline (isoproterenol), levosalbutamol, orciprenaline (metaproterenol), pirbuterol, procaterol, rimiterol, salbutamol (albuterol), terbutaline, tulobuterol, reproterol, ipratropium and epinephrine; long-acting $\beta_2$ adrenergic receptor agonist ("LABA"), e.g., bambuterol, clenbuterol, formoterol, A salmeterol; ultra long-acting $\beta_2$ adrenergic receptor agonists, e.g., carmoterol, milveterol, indacaterol, and saligenin- or indole-containing and adamantyl-derived $\beta_2$ agonists; corticosteroids, e.g., beclomethasone, budesonide, ciclesonide, flunisolide, fluticasone, methyl-prednisolone, mometasone, prednisone and trimacinolone; anti-inflammatories, e.g. fluticasone propionate, beclomethasone dipropionate, flunisolide, budesonide, tripedane, cortisone, prednisone, prednisilone, dexamethasone, betamethasone, or triamcinolone acetonide; antitussives, e.g., noscapine; bronchodilators, e.g., ephedrine, adrenaline, fenoterol, formoterol, isoprenaline, metaproterenol, salbutamol, albuterol, salmeterol, terbutaline; and muscarinic antagonists, including long-acting muscarinic antagonists ("LAMA"), e.g., glycopyrrolate, dexipirronium, scopolamine, tropicamide, pirenzepine, dimenhydrinate, tiotropium, darotropium, aclidinium, trospium, ipratropium, atropine, benzatropin, or oxitropium.

Where appropriate, the active agents provided in the composition, including but not limited to those specifically described herein, may be used in the form of salts (e.g., alkali metal or amine salts or as acid addition salts) or as esters, solvates (hydrates), derivatives, or a free base. Additionally, the active agents may be in any crystalline form or isomeric form or mixture of isomeric forms, for example, as pure enantiomers, a mixture of enantiomers, as racemates or as mixtures thereof. In this regard, the form of the active agents may be selected to optimize the activity and/or stability of the active agent and/or to minimize the solubility of the active agent in the suspension medium.

Because the compositions disclosed provide reproducible delivery of very low doses of active agents, in certain embodiments, the active agents included in the compositions described herein may be selected from one or more potent or highly potent active agents. For example, in certain embodiments, the compositions described herein may include one or more potent active agents that are to be delivered at a dose selected from between about 100 µg and about 100 mg per dose, about 100 µg and about 10 mg per dose, and about 100 µg and 1 mg per dose. In other embodiments, the compositions described herein may include a combination of two or more potent or highly potent active agents that are to be delivered at a dose selected from up to about 80 µg per dose, up to about 40 µg per dose, up to about 20 µg per dose, up to about 10 µg per dose or between about 10 µg and about 100 µg per dose. Additionally, in certain embodiments, the compositions described herein may include a combination of two or more highly potent active agents that are to be delivered at a dose selected from between about 0.1 and about 2 µg per dose, about 0.1 and about 1 µg per dose, and about 0.1 and about 0.5 µg per dose.

In certain embodiments, the compositions described herein include a LABA active agent. In one such embodiment, the composition includes a LABA active agent in combination with a LAMA active agent or a corticosteroid active agent. In another such embodiment, the composition includes a LAMA active agent in combination with a LABA active agent and a corticosteroid. In such embodiments, a LABA active agent can be selected from, for example, bambuterol, clenbuterol, formoterol, salmeterol, carmoterol, milveterol, indacaterol, and saligenin- or indole-containing and adamantyl-derived $\beta_2$ agonists, and any pharmaceutically acceptable salts, esters, isomers or solvates thereof. In certain such embodiments, the active agent is selected from formoterol and its pharmaceutically acceptable salts, esters, isomers or solvates thereof.

Formoterol can be used to treat inflammatory or obstructive pulmonary diseases and disorders such as, for example, those described herein. Formoterol has the chemical name (±)-2-hydroxy-5-[(1RS)-1-hydroxy-2-[[(1RS)-2-(4-methoxyphenyl)-1-methylethyl]-amino]ethyl]formanilide, and is commonly used in pharmaceutical compositions as the racemic fumarate dihydrate salt. Where appropriate, formoterol may be used in the form of salts (e.g. alkali metal or amine salts or as acid addition salts) or as esters or as solvates (hydrates). Additionally, the formoterol may be in any crystalline form or isomeric form or mixture of isomeric forms, for example a pure enantiomer, a mixture of enantiomers, a racemate or a mixture thereof. In this regard, the form of formoterol may be selected to optimize the activity and/or stability of formoterol and/or to minimize the solubility of formoterol in the suspension medium. Pharmaceutically acceptable salts of formoterol include, for example, salts of inorganic acids such as hydrochloric, hydrobromic, sulfuric and phosphoric acids, and organic acids such as fumaric, maleic, acetic, lactic, citric, tartaric, ascorbic, succinic, glutaric, gluconic, tricarballylic, oleic, benzoic, p-methoxybenzoic, salicylic, o- and p-hydroxybenzoic, p-chlorobenzoic, methanesulfonic, p-toluenesulfonic and 3-hydroxy-2-naphthalene carboxylic acids. Hydrates of formoterol are described, for example, in U.S. Pat. No. 3,994,974 and U.S. Pat. No. 5,684,199. Specific crystalline forms are described, for example, in WO95/05805, and specific isomers of formoterol are described in U.S. Pat. No. 6,040,344.

In specific embodiments, the formoterol material utilized to form the formoterol particles is formoterol fumarate, and in one such embodiment, the formoterol fumarate is present in the dihydrate form. Where the compositions described herein include formoterol, in certain embodiments, the compositions described herein may include formoterol at a concentration that achieves a delivered dose selected from between about 0.5 µg and about 30 µg, 0.5 µg and about 1 µg, about 1 µg and about 10 µg, about 2 µg and 5 µg, about 2 µg and about 10 µg, about 5 µg and about 10 µg, and 3 µg and about 30 µg per actuation of an MDI. In other embodiments, the compositions described herein may include formoterol in an amount sufficient to provide a delivered dose selected from up to about 30 µg, up to about 10 µg, up to about 5 µg, up to about 2.5 µg, up to about 2 µg, or up to about 1.5 µg per actuation of an MDI. In order to achieve delivered doses as described herein, where compositions described herein include formoterol as the active agent, in specific embodiments, the amount of formoterol included in the compositions may be selected from, for example, between about 0.01 mg/ml and about 1 mg/ml, between about 0.01 mg/ml and about 0.5 mg/ml, and between about 0.03 mg/ml and about 0.4 mg/ml.

Where the pharmaceutical co-suspension compositions described herein include a LABA active agent, in certain embodiments, the active agent is selected from salmeterol, including any pharmaceutically acceptable salts, esters, isomers or solvates thereof. Salmeterol can be used to treat inflammatory or obstructive pulmonary diseases and disorders such as, for example, those described herein. Again, where salmerterol is included as the LABA active agent, in some such embodiments, the compositions may also include a LAMA or corticosteroid active agent. In other such embodiments, the compositions include salmeterol in combination with a LAMA active agent and a corticosteroid. Salmeterol, pharmaceutically acceptable salts of salmeterol, and methods for producing the same are described, for example, in U.S. Pat. No. 4,992,474, U.S. Pat. No. 5,126,375, and U.S. Pat. No. 5,225,445.

Where salmeterol is included as a LABA active agent, in certain embodiments, the compositions described herein may include salmeterol at a concentration that achieves a delivered dose selected from between about 2 µg and about 120 µg, about 4 µg and about 40 µg, about 8 µg and 20 µg, about 8 µg and about 40 µg, about 20 µg and about 40 µg, and about 12 µg and about 120 µg per actuation of an MDI. In other embodiments, the compositions described herein may include salmeterol in an amount sufficient to provide a delivered dose selected from up to about 120 µg, up to about 40 µg, up to about 20 µg, up to about 10 µg, up to about 8 µg, or up to about 6 µg per actuation of an MDI. In order to achieve targeted delivered doses as described herein, where compositions described herein include salmeterol as the active agent, in specific embodiments, the amount of salmeterol included in the compositions may be selected from, for example, between about 0.04 mg/ml and about 4 mg/ml, between about 0.04 mg/ml and about 2.0 mg/ml, and between about 0.12 mg/ml and about 0.8 mg/ml. For example, the compositions described herein may include sufficient salmeterol to provide a target delivered dose selected from between about 4 µg and about 120 µg, about 20 µg and about 100 µg, and between about 40 µg and about 120 µg per actuation of an MDI. In still other embodiments, the compositions described herein may include sufficient salmeterol to provide a targeted delivered dose selected from up to about 100 µg, up to about 40 µg, or up to about 15 µg per actuation of an MDI.

In certain embodiments, the compositions described herein include a long-acting muscarinic antagonist (LAMA) active agent. Examples of LAMA active agents that may be used in the compositions described herein include, glycopyrrolate, dexipirronium, tiotropium, trospium, aclidinium and darotropium, including any pharmaceutically acceptable salts, esters, isomers or solvates thereof. In some embodiments, the compositions described herein include a LAMA active agent in combination with a LABA active agent or a corticosteroid. In other such embodiments, the compositions described herein include a LAMA active agent in combination with both LABA and corticosteroid active agents. Where the compositions include a LAMA active agent, in particular embodiments, glycopyrrolate, including any pharmaceutically acceptable salts, esters, isomers or solvates thereof, may be selected.

Glycopyrrolate can be used to treat inflammatory or obstructive pulmonary diseases and disorders such as, for example, those described herein. As an anticholinergic, glycopyrrolate provides an antisecretory effect, which is a benefit for use in the therapy of pulmonary diseases and disorders characterized by increased mucus secretions. Glycopyrrolate is a quaternary ammonium salt. Where appropriate, glycopyrrolate may be used in the form of salts (e.g. alkali metal or amine salts, or as acid addition salts), esters, solvates (hydrates), or selected isomers. Additionally, the glycopyrrolate may be in any crystalline form or isomeric form or mixture of isomeric forms, for example a pure enantiomer, a mixture of enantiomers, a racemate or a mixture thereof. In this regard, the form of glycopyrrolate may be selected to optimize the activity and/or stability of glycopyrrolate and/or to minimize the solubility of glycopyrrolate in the suspension medium. Suitable counter ions are pharmaceutically acceptable counter ions including, for example, fluoride, chloride, bromide, iodide, nitrate, sulfate, phosphate, formate, acetate, trifluoroacetate, propionate, butyrate, lactate, citrate, tartrate, malate, maleate, succinate, benzoate, p-chlorobenzoate, diphenyl-acetate or triphenylacetate, o-hydroxybenzoate, p-hydroxybenzoate, 1-hydroxynaphthalene-2-carboxylate, 3-hydroxynaphthalene-2-carboxylate, methanesulfonate and benzenesulfonate. In particular embodiments of the compositions described herein, the bromide salt of glycopyrrolate, namely 3-[(cyclopentyl-hydroxyphenylacetyl)oxy]-1,1-dimethylpyrrolidinium bromide, is used and can be prepared according to the procedures set out in U.S. Pat. No. 2,956,062.

Where the compositions described herein include glycopyrrolate, in certain embodiments, the compositions may include sufficient glycopyrrolate to provide a delivered dose selected from between about 10 µg and about 100 µg, about 15 µg and about 100 µg, about 15 µg and about 80 µg, and about 10 µg and about 80 µg per actuation of an MDI. In other such embodiments, the formulations include sufficient glycopyrrolate to provide a delivered dose selected from up to about 100 µg, up to about 80 µg, up to about 40 µg, up to about 20 µg, or up to about 10 µg per actuation of an MDI. In yet further embodiments, the formulations include sufficient glycopyrrolate to provide a delivered dose selected from about 9 µg, 18 µg, 36 µg and 72 µg per actuation of the MDI. In order to achieve delivered doses as described herein, where compositions described herein include glycopyrrolate as the active agent, in specific embodiments, the amount of glycopyrrolate included in the compositions may be selected from, for example, between about 0.04 mg/ml and about 2.25 mg/ml.

In other embodiments, tiotropium, including any pharmaceutically acceptable salts, esters, isomers or solvates thereof, may be selected as a LAMA active agent for inclusion in a composition as described herein. Tiotropium is a known, long-acting anticholinergic drug suitable for use in treating diseases or disorders associated with pulmonary inflammation or obstruction, such as those described herein. Tiotropium, including crystal and pharmaceutically acceptable salt forms of tiotropium, is described, for example, in U.S. Pat. No. 5,610,163, U.S. Pat. No. RE39820, U.S. Pat. No. 6,777,423, and U.S. Pat. No. 6,908,928. Where the compositions described herein include tiotropium, in certain embodiments, the compositions may include sufficient tiotropium to provide a delivered dose selected from between about 2.5 µg and about 25 µg, about 4 µg and about 25 µg, about 2.5 µg and about 20 µg, and about 10 µg and about 20 µg per actuation of an MDI. In other such embodiments, the formulations include sufficient tiotropium to provide a delivered dose selected from up to about 25 µg, up to about 20 µg, up to about 10 µg, up to about 5 µg, or up to about 2.5 µg per actuation of an MDI. In yet further embodiments, the formulations include sufficient tiotropium to provide a delivered dose selected from about 3 µg, 6 µg, 9 µg, and 18 µg per actuation of the MDI. In order to achieve delivered doses as described herein, where compositions described herein include tiotropium as the active agent, in specific embodiments, the amount of tiotropium included in the compositions may be selected from, for example, between about 0.01 mg/ml and about 0.5 mg/ml.

In still other embodiments, the compositions described herein include a corticosteroid. Such active agents may be selected from, for example, beclomethasone, budesonide, ciclesonide, flunisolide, fluticasone, methyl-prednisolone, mometasone, prednisone and trimacinolone, including any pharmaceutically acceptable salts, esters, isomers or solvates thereof. In some embodiments, such compositions include a corticosteroid active agent in combination with a LAMA or LABA active agent. In other such embodiments, the compositions include a corticosteroid active agent in combination with a LAMA and a LABA active agent. Where the compositions include a corticosteroid active agent, in particular embodiments, mometasone may be selected Mometasone, pharmaceutically acceptable salts of mometasone, such as mometasone furoate, and preparation of such materials are known, and described, for example, in U.S. Pat. No. 4,472,393, U.S. Pat. No. 5,886,200, and U.S. Pat. No. 6,177,560. Mometasone is suitable for use in treating diseases or disorders associated with pulmonary inflammation or obstruction, such as those described herein (see, e.g., U.S. Pat. No. 5,889,015, U.S. Pat. No. 6,057,307, U.S. Pat. No. 6,057,581, U.S. Pat. No. 6,677,322, U.S. Pat. No. 6,677,323 and U.S. Pat. No. 6,365,581).

Where the compositions described herein include mometasone, in particular embodiments, the compositions include mometasone, including any pharmaceutically acceptable salts, esters, isomers or solvates thereof, in an amount sufficient to provide a target delivered dose selected from between about 20 µg and about 400 µg, about 20 µg and about 200 µg, about 50 µg and about 200 µg, about 100 µg and about 200 µg, about 20 µg and about 100 µg, and about 50 µg and about 100 µg, per actuation of an MDI. In still other embodiments, the compositions described herein may include mometasone, including any pharmaceutically acceptable salts, esters, isomers or solvates thereof, in an amount sufficient to provide a targeted delivered dose selected from up to about 400 µg, up to about 200 µg, or up to about 100 µg per actuation of an MDI.

In other embodiments, the compositions described herein include a corticosteroid selected from fluticasone and budesonide. Both fluticasone and budesonide are suitable for use in treatment of conditions associated with pulmonary inflammation or obstruction, such as those described herein. Fluticasone, pharmaceutically acceptable salts of fluticasone, such as fluticasone propionate, and preparation of such materials are known, and described, for example, in U.S. Pat. No. 4,335,121, U.S. Pat. No. 4,187,301, and U.S. Pat. Pub. No. US2008125407. Budesonide is also well known and described, for example, in U.S. Pat. No. 3,929,768. In certain embodiments, compositions described herein may include fluticasone, including any pharmaceutically acceptable salts, esters, isomers or solvates thereof, in an amount sufficient to provide a target delivered dose selected from between about 20 µg and about 200 µg, about 50 µg and about 175 µg, and between about 80 µg and about 160 µg per actuation of an MDI. In other embodiments, the compositions described herein may include fluticasone, including any pharmaceutically acceptable salts, esters, isomers or solvates thereof, in an amount sufficient to provide a targeted delivered dose selected from up to about 175 µg, up to about 160 µg, up to about 100 µg, or up to about 80 µg per actuation of an MDI. In particular embodiments, compositions described herein may include budesonide, including any pharmaceutically acceptable salts, esters, isomers or solvates thereof, in an amount sufficient to provide target delivered dose selected from between about 30 µg and about 240 µg, about 30 µg and about 120 µg, and between about 30 µg and about 50 µg per actuation of an MDI. In still other embodiments, the compositions described herein may include budesonide, including any pharmaceutically acceptable salts, esters, isomers or solvates thereof, in an amount sufficient to provide a targeted delivered dose selected from up to about 240 µg, up to about 120 µg, or up to about 50 µg per actuation of an MDI.

In each embodiment, a composition as described herein includes two or more active agents. In some embodiments, the compositions include a combination of two or more species of active agent particles which may be co-suspended with a single species of suspending particles. Alternatively, a composition may include two or more species of active agent particles co-suspended with two or more different species of suspending particles. As yet another alternative, compositions as described herein may include a single species of active agent particles suspended with a single species of suspending particles, wherein the single species of active agent particles incorporates one or more active agents and the single species of suspending particles incorporates one or more active agents. Even further, a composition as described herein may include two or more active agents combined within a single species of active agent particle. For example, where the active agent particles are formulated using one or more excipients or adjuvants in addition to the active agent material, such active agent particles may include individual particles that include two or more different active agents.

(iii) Suspending Particles

The suspending particles included in the co-suspension compositions described herein work to facilitate stabilization and delivery of the active agent included in the compositions. Though various forms of suspending particles may be used, the suspending particles are typically formed from pharmacologically inert material that is acceptable for inhalation and is substantially insoluble in the propellant selected. Generally, the majority of suspending particles are sized within a respirable range. In particular embodiments, therefore, the MMAD of the suspending particles will not exceed about 10 µm but is not lower than about 500 nm. In an alternative embodiment, the MMAD of the suspending particles is between about 5 µm and about 750 nm. In yet another embodiment, the MMAD of the suspending particles is between about 1 µm and about 3 µm. When used in an embodiment for nasal delivery from an MDI, the MMAD of the suspending particles is between 10 µm and 50 µm.

In order to achieve respirable suspending particles within the MMAD ranges described, the suspending particles will typically exhibit a volume median optical diameter between about 0.2 µm and about 50 µm. In one embodiment, the suspending particles exhibit a volume median optical diameter that does not exceed about 25 µm. In another embodiment, the suspending particles exhibit a volume median optical diameter selected from between about 0.5 µm and about 15 µm, between about 1.5 µm and about 10 µm, and between about 2 µm and about 5 µm.

The concentration of suspending particles included in a composition according to the present description can be adjusted, depending on, for example, the amount of active agent particles and suspension medium used. In one embodiment, the suspending particles are included in the suspension medium at a concentration selected from about 1 mg/ml to about 15 mg/ml, about 3 mg/ml to about 10 mg/ml, 5 mg/ml to about 8 mg/ml, and about 6 mg/ml. In another embodiment, the suspending particles are included in the suspension medium at a concentration of up to about 30 mg/ml. In yet another embodiment, the suspending particles are included in the suspension medium at a concentration of up to about 25 mg/ml.

The relative amount of suspending particles to active agent particles is selected to achieve a co-suspension as contemplated herein. A co-suspension composition may be achieved where the amount of suspending particles, as measured by mass, exceeds that of the active agent particles. For example, in specific embodiments, the ratio of the total mass of the suspending particles to the total mass of active agent particles may be between about 3:1 and about 15:1, or alternatively from about 2:1 and 8:1. Alternatively, the ratio of the total mass of the suspending particles to the total mass of active agent particles may be above about 1, such as up to about 1.5, up to about 5, up to about 10, up to about 15, up to about 17, up to about 20, up to about 30, up to about 40, up to about 50, up to about 60, up to about 75, up to about 100, up to about 150, and up to about 200, depending on the nature of the suspending particles and active agent particles used. In further embodiments, the ratio of the total mass of the suspending particles to the total mass of the active agent particles may be selected from between about 10 and about 200, between about 60 and about 200, between about 15 and about 60, between about 15 and about 170, between about 15 and about 60, about 16, about 60, and about 170.

In other embodiments, the amount of suspending particles, as measured by mass, is less than that of the active agent particles. For example, in particular embodiments, the mass of the suspending particles may be as low as 20% of the total mass of the active agent particles. However, in some embodiments, the total mass of the suspending particles may also approximate or equal the total mass of the active agent particles.

Suspending particles suitable for use in the compositions described herein may be formed of one or more pharmaceutically acceptable materials or excipients that are suitable for inhaled delivery and do not substantially degrade or dissolve in the suspension medium. In one embodiment, perforated microstructures, as defined herein, may be used as the suspending particles. Exemplary excipients that may be used in the formulation of suspending particles described herein include but are not limited to (a) carbohydrates, e.g., monosaccharides such as fructose, galactose, glucose, D-mannose, sorbose, and the like; disaccharides, such as sucrose, lactose, trehalose, cellobiose, and the like; cyclodextrins, such as 2-hydroxypropyl-β-cyclodextrin; and polysaccharides, such as raffinose, maltodextrins, dextrans, starches, chitin, chitosan, inulin, and the like; (b) amino acids, such as alanine, glycine, arginine, aspartic acid, glutamic acid, cysteine, lysine, leucine, isoleucine, valine, and the like; (c) metal and organic salts prepared from organic acids and bases, such as sodium citrate, sodium ascorbate, magnesium gluconate, sodium gluconate, tromethamin hydrochloride, and the like; (d) peptides and proteins such as aspartame, trileucine, human serum albumin, collagen, gelatin, and the like; (e) alditols, such as mannitol, xylitol, and the like; (f) synthetic or natural polymers or combinations thereof, such as polylactides, polylactide-glycolides, cyclodextrins, polyacrylates, methylcellulose, carboxymethylcellulose, polyvinyl alcohols, polyanhydrides, polylactams, polyvinyl pyrrolidones, hyaluronic acid, polyethylene glycols; and (g) surfactants including fluorinated and nonfluorinated compounds such as saturated and unsaturated lipids, nonionic detergents, nonionic block copolymers, ionic surfactants and combinations thereof. In particular embodiments, suspending particles may include a calcium salt, such as calcium chloride, as described, for example, in U.S. Pat. No. 7,442,388.

Additionally, phospholipids from both natural and synthetic sources may be used in preparing suspending particles suitable for use in the compositions described herein. In particular embodiments, the phospholipid chosen will have a gel to liquid crystal phase transition of greater than about 40° C. Exemplary phospholipids are relatively long chain (i.e., $C_{16}$-$C_{22}$) saturated lipids and may comprise saturated phospholipids, such as saturated phosphatidylcholines having acyl chain lengths of 16 C or 18 C (palmitoyl and stearoyl). Exemplary phospholipids include phosphoglycerides such as dipalmitoylphosphatidylcholine, disteroylphosphatidylcholine, diarachidoylphosphatidylcholine, dibehenoylphosphatidylcholine, diphosphatidyl glycerol, short-chain phosphatidylcholines, long-chain saturated phosphatidylethanolamines, long-chain saturated phosphatidylserines, long-chain saturated phosphatidylglycerols, and long-chain saturated phosphatidylinositols. Additional excipients are disclosed in International Patent Publication No. WO 96/32149 and U.S. Pat. Nos. 6,358,530, 6,372,258 and 6,518,239.

In particular embodiments, the suspending particles may be formed using one or more lipids, phospholipids or saccharides, as described herein. In some embodiments, suspending particles include one or more surfactants. The use of suspending particles formed of or incorporating one or more surfactants may promote absorption of the selected active agent, thereby increasing bioavailability. The suspending particles described herein, such as, for example, suspending particles formed using one or more lipids, can be formed to exhibit a desired surface rugosity (roughness), which can further reduce inter-particle interactions and improve aerosolization by reducing the surface area available for particle-particle interaction. In further embodiments, if suitable, a lipid that is naturally occurring in the lung could be used in forming the suspending particles, as such suspending particles that have the potential to reduce opsonization (and thereby reducing phagocytosis by alveolar macrophages), thus providing a longer-lived controlled release particle in the lung.

In another aspect, the suspending particles utilized in the compositions described herein may be selected to increase storage stability of the selected active agent, similar to that disclosed in International Patent Publication No WO 2005/000267. For example, in one embodiment, the suspending particles my include pharmaceutically acceptable glass stabilization excipients having a Tg of at least 55° C., at least 75° C., or at least 100° C. Glass formers suitable for use in compositions described herein include, but are not limited to, one or more of trileucine, sodium citrate, sodium phosphate, ascorbic acid, inulin, cyclodextrin, polyvinyl pyrrolidone, mannitol, sucrose, trehalose, lactose, and, proline. Examples of additional glass-forming excipients are disclosed in U.S. Pat. Nos. RE 37,872, 5,928,469, 6,258,341, and 6,309,671.

The suspending particles may be designed, sized and shaped as desired to provide desirable stability and active agent delivery characteristics. In one exemplary embodiment, the suspending particles comprise perforated microstructures as described herein. Where perforated microstructures are used as suspending particles in the compositions described herein, they may be formed using one or more excipients as described herein. For example, in particular embodiments, perforated microstructures may include at least one of the following: lipids, phospholipids, nonionic detergents, nonionic block copolymers, ionic surfactants, biocompatible fluorinated surfactants and combinations thereof, particularly those approved for pulmonary use. Specific surfactants that may be used in the preparation of perforated microstructures include poloxamer 188, poloxamer 407 and poloxamer 338. Other specific surfactants include oleic acid or its alkali salts. In one embodiment, the perforated microstructures include greater than about 10% w/w surfactant.

In some embodiments, suspending particles may be prepared by forming an oil-in-water emulsion, using a fluorocarbon oil (e.g., perfluorooctyl bromide, perfluorodecalin) which may be emulsified using a surfactant such as a long chain saturated phospholipid. The resulting perfluorocarbon in water emulsion may be then processed using a high pressure homogenizer to reduce the oil droplet size. The perfluorocarbon emulsion may be fed into a spray dryer, optionally with an active agent solution, if it is desirable to include active agent within the matrix of the perforated microstructures. As is well known, spray drying is a one-step process that converts a liquid feed to a dried particulate form. Spray drying has been used to provide powdered pharmaceutical material for various administrative routes, including inhalation. Operating conditions of the spray dryer (such as inlet and outlet temperature, feed rate, atomization pressure, flow rate of the drying air and nozzle configuration) can be adjusted to produce the desired particle size producing a yield of the resulting dry microstructures. Such methods of producing exemplary perforated microstructures are disclosed in U.S. Pat. No. 6,309,623 to Weers et al.

Perforated microstructures as described herein may also be formed through lyophilization and subsequent milling or micronization. Lyophilization is a freeze-drying process in which water is sublimed from the composition after it is frozen. This process allows drying without elevated temperatures. In yet further embodiments, the suspending particles may be produced using a spray freeze drying process, such as is disclosed in U.S. Pat. No. 5,727,333.

Furthermore, suspending particles as described herein may include bulking agents, such as polymeric particles. Polymeric polymers may be formed from biocompatible and/or biodegradable polymers, copolymers or blends. In one embodiment, polymers capable of forming aerodynamically light particles may be used, such as functionalized polyester graft copolymers and biodegradable polyanhydrides. For example, bulk eroding polymers based on polyesters including poly(hydroxy acids) can be used. Polyglycolic acid (PGA), polyactic acid (PLA) or copolymers thereof may be used to form suspending particles. The polyester may include a charged or functionalizable group, such as an amino acid. For example, suspending particles may be formed of poly(D, L-lactic acid) and/or poly(D,L-lactic-co-glycolic acid) (PLGA), which incorporate a surfactant such as DPPC.

Other potential polymer candidates for use in suspending particles may include polyamides, polycarbonates, polyalkylenes such as polyethylene, polypropylene, poly(ethylene glycol), poly(ethylene oxide), poly(ethylene terephthalate), poly vinyl compounds such as polyvinyl alcohols, polyvinyl ethers, and polyvinyl esters, polymers of acrylic and methacrylic acids, celluloses and other polysaccharides, and peptides or proteins, or copolymers or blends thereof. Polymers may be selected with or modified to have the appropriate stability and degradation rates in vivo for different controlled drug delivery applications.

The compositions described herein may include two or more species of suspending particles. Even further, compositions according to the present description can include suspending particles that include one or more active agents incorporated into the suspending particles. Where active agent is incorporated into suspending particles, the suspending particles will be of a respirable size and can be formulated and produced using, for example, the methods and materials described herein.

Compositions formulated according to the present teachings can inhibit degradation of active agent included therein. For example, in specific embodiments, the compositions described herein inhibit one or more of flocculation, aggregation and the solution mediated transformation of active agent material included in the compositions. The pharmaceutical compositions described herein are suited for respiratory delivery via and MDI in a manner that achieves desirable delivered dose uniformity ("DDU") of each active agent included in a combination of two or more active agents, even with combinations including potent and highly potent actives. As is illustrated in detail in the Examples included herein, even when delivering very low doses of two or more active agents, compositions described herein can achieve a DDU of ±30%, or better, for each active agent throughout emptying of an MDI canister. In one such embodiment, compositions described herein achieve a DDU of ±25%, or better, for each active agent throughout emptying of an MDI canister. In yet another such embodiment, compositions described herein achieve a DDU for the active agent of ±20%, or better, for each active agent throughout emptying of an MDI canister.

Pharmaceutical compositions described herein also serve to substantially preserve FPF and FPD performance throughout emptying of an MDI canister, even after being subjected to accelerated degradation conditions. For instance, compositions according to the present description maintain as much as 80%, 90%, 95%, or more, of the original FPF and FPD performance throughout emptying of an MDI canister, even after being subjected to accelerated degradation conditions. Compositions described herein provide the added benefit of achieving such performance while being formulated using non-CFC propellants and eliminating or substantially avoiding pharmaceutical effects often experienced with compositions incorporating multiple active agents. In specific embodiments, the compositions described herein achieve desired one or all of a targeted DDU, FPF and FPD performance while being formulated with suspension medium including only one or more non-CFC propellants and without the need to modify the characteristics of the non-CFC propellant, such as by the addition of, for example, one or more cosolvent, antisolvent, solubilizing agent, adjuvant or other propellant modifying material.

In one embodiment, a co-suspension composition deliverable from a metered dose inhaler according to the present description includes the following: a suspension medium comprising a pharmaceutically acceptable HFA propellant; a first species of active agent particles comprising glycopyrrolate, including any pharmaceutically acceptable salts, esters, isomers or solvates thereof, suspended in the suspension medium at a concentration sufficient to provide a delivered dose of glycopyrrolate of between about 15 µg and about 80 µg per actuation of the metered dose inhaler; a second species of active agent particles comprising formoterol, including any pharmaceutically acceptable salts, esters, isomers or solvates thereof, suspended in the suspension medium at a concentration sufficient to provide a delivered dose of formoterol of between about 2 µg and about 10 µg per actuation of the metered dose inhaler; and a plurality of respirable suspending particles comprising perforated microstructures exhibiting a volume median optical diameter of between about 1.5 µm and about 10 µm, wherein the first and second species of active agent particles associate with the plurality of suspending particles to form a co-suspension. In one such embodiment, the ratio of the total mass of the suspending particles to the total mass of the first and second species of active agent particles is selected from between about 3:1 and about 15:1 and between about 2:1 and 8:1.

In another embodiment, a co-suspension composition deliverable from a metered dose inhaler according to the present description includes the following: a suspension medium comprising a pharmaceutically acceptable HFA propellant; a first species of active agent particles comprising tiotropium, including any pharmaceutically acceptable salts, esters, isomers or solvates thereof, suspended in the suspension medium at a concentration sufficient to provide a delivered dose of tiotropium of between about 5 µg and about 20 µg per actuation of the metered dose inhaler; a second species of active agent particles comprising formoterol, including any pharmaceutically acceptable salts, esters, isomers or solvates thereof, suspended in the suspension medium at a concentration sufficient to provide a delivered dose of formoterol of between about 2 µg and about 10 µg per actuation of the metered dose inhaler; and a plurality of respirable suspending particles comprising perforated microstructures exhibiting a volume median optical diameter of between about 1.5 µm and about 10 µm, wherein the first and second species of active agent particles associate with the plurality of suspending particles to form a co-suspension. In one such embodiment, the ratio of the total mass of the suspending particles to the total mass of the first and second species of active agent particles is selected from between about 3:1 and about 15:1 and between about 2:1 and 8:1.

In another embodiment, a co-suspension composition deliverable from a metered dose inhaler according to the present description includes the following: a suspension medium comprising a pharmaceutically acceptable HFA propellant; a plurality of active agent particles comprising glycopyrrolate, including any pharmaceutically acceptable salts, esters, isomers or solvates thereof, suspended in the suspension medium at a concentration sufficient to provide a delivered dose of glycopyrrolate of between about 15 µg and about 80 µg per actuation of the metered dose inhaler; and a plurality of respirable suspending particles comprising formoterol, including any pharmaceutically acceptable salts, esters, isomers or solvates thereof, wherein the plurality of suspending particles exhibit a volume median optical diameter of between about 1.5 µm and about 10 µm, are included in the suspension medium at a concentration sufficient to provide a delivered dose of formoterol of between about 2 µg and about 10 µg per actuation of the metered dose inhaler, and associate with the plurality of active agent particles to form a co-suspension. In one such embodiment, the ratio of the total mass of the suspending particles to the total mass of the first and second species of active agent particles is selected from between about 3:1 and about 15:1 and between about 2:1 and 8:1.

In another embodiment, a co-suspension composition deliverable from a metered dose inhaler according to the present description includes the following: a suspension medium comprising a pharmaceutically acceptable HFA propellant; a plurality of active agent particles comprising tiotropium, including any pharmaceutically acceptable salts, esters, isomers or solvates thereof, suspended in the suspension medium at a concentration sufficient to provide a delivered dose of tiotropium of between about 5 µg and about 20 µg per actuation of the metered dose inhaler; and a plurality of respirable suspending particles comprising formoterol, including any pharmaceutically acceptable salts, esters, isomers or solvates thereof, wherein the plurality of suspending particles exhibit a volume median optical diameter of between about 1.5 µm and about 10 µm, are included in the suspension medium at a concentration sufficient to provide a delivered dose of formoterol of between about 2 µg and about 10 µg per actuation of the metered dose inhaler, and associate with the plurality of active agent particles to form a co-suspension. In one such embodiment, the ratio of the total mass of the suspending particles to the total mass of the first and second species of active agent particles is selected from between about 3:1 and about 15:1 and between about 2:1 and 8:1.

In another embodiment, a co-suspension composition deliverable from a metered dose inhaler according to the present description includes the following: a suspension medium comprising a pharmaceutically acceptable HFA propellant; a first species of active agent particles comprising glycopyrrolate, including any pharmaceutically acceptable salts, esters, isomers or solvates thereof, suspended in the suspension medium at a concentration sufficient to provide a delivered dose of glycopyrrolate of between about 15 µg and about 80 µg per actuation of the metered dose inhaler; a second species of active agent particles comprising formoterol, including any pharmaceutically acceptable salts, isomers or solvates thereof, suspended in the suspension medium at a concentration sufficient to provide a delivered dose of formoterol of between about 2 µg and about 10 µg per actuation of the metered dose inhaler; a third species of active agent particles comprising a corticosteroid selected from beclomethasone, budesonide, ciclesonide, flunisolide, fluticasone, methyl-prednisolone, mometasone, prednisone and trimacinolone, including any pharmaceutically acceptable salts, esters, isomers or solvates thereof; and a plurality of respirable suspending particles comprising perforated microstructures exhibiting a volume median optical diameter of between about 1.5 µm and about 10 µm, wherein the first, second and third species of active agent particles associate with the plurality of suspending particles to form a co-suspension. In one such embodiment, at least 90% of the first, second, and third species of active agent particles by volume exhibit an optical diameter of less than 7 µm, and the ratio of the total mass of the suspending particles to the total mass of the first, second, and third species of active agent particles is selected from between about 3:1 and about 15:1 and between about 2:1 and 8:1.

In another embodiment, a co-suspension composition deliverable from a metered dose inhaler according to the present description includes the following: a suspension medium comprising a pharmaceutically acceptable HFA propellant; a first species of active agent particles comprising glycopyrrolate, including any pharmaceutically acceptable salts, esters, isomers or solvates thereof, suspended in the suspension medium at a concentration sufficient to provide a delivered dose of glycopyrrolate of between about 15 µg and about 80 µg per actuation of the metered dose inhaler; a second species of active agent particles comprising formoterol, including any pharmaceutically acceptable salts, esters, isomers or solvates thereof, suspended in the suspension medium at a concentration sufficient to provide a delivered dose of formoterol of between about 2 µg and about 10 µg per actuation of the metered dose inhaler; a third species of active agent particles comprising budesonide, including any pharmaceutically acceptable salts, esters, isomers or solvates thereof, suspended in the suspension medium at a concentration sufficient to provide a delivered dose of budesonide of between about 30 µg and about 50 µg per actuation of the metered dose inhaler; and a plurality of respirable suspending particles comprising perforated microstructures exhibiting a volume median optical diameter of between about 1.5 µm and about 10 µm, wherein the first, second and third species of active agent particles associate with the plurality of suspending particles to form a co-suspension. In one such embodiment, at least 90% of the first, second, and third species of active agent particles by volume exhibit an optical diameter of less than 7 µm, and the ratio of the total mass of the suspending particles to the total mass of the first, second, and third species of active agent particles is selected from between about 3:1 and about 15:1 and between about 2:1 and 8:1.

In another embodiment, a co-suspension composition deliverable from a metered dose inhaler according to the present description includes the following: a suspension medium comprising a pharmaceutically acceptable HFA propellant; a first species of active agent particles comprising tiotropium, including any pharmaceutically acceptable salts, esters, isomers or solvates thereof, suspended in the suspension medium at a concentration sufficient to provide a delivered dose of tiotropium of between about 5 µg and about 20 µg per actuation of the metered dose inhaler; a second species of active agent particles comprising formoterol, including any pharmaceutically acceptable salts, esters, isomers or solvates thereof, suspended in the suspension medium at a concentration sufficient to provide a delivered dose of formoterol of between about 2 µg and about 10 µg per actuation of the metered dose inhaler; a third species of active agent particles comprising budesonide, including any pharmaceutically acceptable salts, esters, isomers or solvates thereof suspended in the suspension medium at a concentration sufficient to provide a delivered dose of budesonide of between about 30 µg and about 50 µg per actuation of the metered dose inhaler; and a plurality of respirable suspending particles comprising perforated microstructures exhibiting a volume median optical diameter of between about 1.5 µm and about 10 µm, wherein the first, second and third species of active agent particles associate with the plurality of suspending particles to form a co-suspension. In one such embodiment, at least 90% of the first, second, and third species of active agent particles by volume exhibit an optical diameter of less than 7 µm, and the ratio of the total mass of the suspending particles to the total mass of the first, second, and third species of active agent particles is selected from between about 3:1 and about 15:1 and between about 2:1 and 8:1.

In another embodiment, a co-suspension composition deliverable from a metered dose inhaler according to the present description includes the following: a suspension medium comprising a pharmaceutically acceptable HFA propellant; a first species of active agent particles comprising glycopyrrolate, including any pharmaceutically acceptable salts, esters, isomers or solvates thereof, suspended in the suspension medium at a concentration sufficient to provide a delivered dose of glycopyrrolate of between about 15 µg and about 80 µg per actuation of the metered dose inhaler; a second species of active agent particles comprising formoterol, including any pharmaceutically acceptable salts, esters, isomers or solvates thereof, suspended in the suspension medium at a concentration sufficient to provide a delivered dose of formoterol of between about 2 µg and about 10 µg per actuation of the metered dose inhaler; a third species of active agent particles comprising mometasone, including any pharmaceutically acceptable salts, esters, isomers or solvates thereof, suspended in the suspension medium at a concentration sufficient to provide a delivered dose of mometasone of between about 20 µg and about 100 µg per actuation of the metered dose inhaler; and a plurality of respirable suspending particles comprising perforated microstructures exhibiting a volume median optical diameter of between about 1.5 µm and about 10 µm, wherein the first, second and third species of active agent particles associate with the plurality of suspending particles to form a co-suspension. In one such embodiment, at least 90% of the first, second, and third species of active agent particles by volume exhibit an optical diameter of less 7 µm, and the ratio of the total mass of the suspending particles to the total mass of the first, second, and third species of active agent particles is selected from between about 3:1 and about 15:1 and between about 2:1 and 8:1.

In another embodiment, a co-suspension composition deliverable from a metered dose inhaler according to the present description includes the following: a suspension medium comprising a pharmaceutically acceptable HFA propellant; a first species of active agent particles comprising tiotropium, including any pharmaceutically acceptable salts, esters, isomers or solvates thereof, suspended in the suspension medium at a concentration sufficient to provide a delivered dose of tiotropium of between about 5 µg and about 20 µg per actuation of the metered dose inhaler; a second species of active agent particles comprising formoterol, including any pharmaceutically acceptable salts, esters, isomers or solvates thereof, suspended in the suspension medium at a concentration sufficient to provide a delivered dose of formoterol of between about 2 µg and about 10 µg per actuation of the metered dose inhaler; a third species of active agent particles comprising mometasone, including any pharmaceutically acceptable salts, esters, isomers or solvates thereof suspended in the suspension medium at a concentration sufficient to provide a delivered dose of mometasone of between about 20 μg and about 100 μg per actuation of the metered dose inhaler; and a plurality of respirable suspending particles comprising perforated microstructures exhibiting a volume median optical diameter of between about 1.5 μm and about 10 μm, wherein the first, second and third species of active agent particles associate with the plurality of suspending particles to form a co-suspension. In one such embodiment, at least 90% of the first, second, and third species of agent particles by volume exhibit an optical diameter of less than 7 μm, and the ratio of the total mass of the suspending particles to the total mass of the first, second, and third species of active agent particles is selected from between about 3:1 and about 15:1 and between about 2:1 and 8:1.

In another embodiment, a co-suspension composition deliverable from a metered dose inhaler according to the present description includes the following: a suspension medium comprising a pharmaceutically acceptable HFA propellant; a first species of active agent particles comprising glycopyrrolate, including any pharmaceutically acceptable salts, esters, isomers or solvates thereof, suspended in the suspension medium at a concentration sufficient to provide a delivered dose of glycopyrrolate of between about 15 μg and about 80 μg per actuation of the metered dose inhaler; a second species of active agent particles comprising formoterol, including any pharmaceutically acceptable salts, esters, isomers or solvates thereof, suspended in the suspension medium at a concentration sufficient to provide a delivered dose of formoterol of between about 2 μg and about 10 μg per actuation of the metered dose inhaler; and a plurality of respirable suspending particles comprising perforated microstructures incorporating a corticosteroid selected from beclomethasone, budesonide, ciclesonide, flunisolide, fluticasone, methyl-prednisolone, mometasone, prednisone and trimacinolone, including any pharmaceutically acceptable salts, esters, isomers or solvates thereof, wherein the suspending particles exhibit a volume median optical diameter of between about 1.5 μm and about 10 μm and associate with the first and second species of active agent particles to form a co-suspension. In one such embodiment, at least 90% of the first and second species of active agent particles by volume exhibit an optical diameter of less than 7 μm, and the ratio of the total mass of the suspending particles to the total mass of the first and second species of active agent particles is selected from between about 3:1 and about 15:1 and between about 2:1 and 8:1.

In another embodiment, a co-suspension composition deliverable from a metered dose inhaler according to the present description includes the following: a suspension medium comprising a pharmaceutically acceptable HFA propellant; a first species of active agent particles comprising glycopyrrolate, including any pharmaceutically acceptable salts, esters, isomers or solvates thereof, suspended in the suspension medium at a concentration sufficient to provide a delivered dose of glycopyrrolate of between about 15 μg and about 80 μg per actuation of the metered dose inhaler; a second species of active agent particles comprising formoterol, including any pharmaceutically acceptable salts, esters, isomers or solvates thereof, suspended in the suspension medium at a concentration sufficient to provide a delivered dose of formoterol of between about 2 μg and about 10 μg per actuation of the metered dose inhaler; and a plurality of respirable suspending particles comprising perforated microstructures incorporating budesonide, including any pharmaceutically acceptable salts, esters, isomers or solvates thereof, wherein the suspending particles include sufficient budesonide to provide a delivered dose of budesonide of between about 30 μg and about 50 μg per actuation of the metered dose inhaler, exhibit a volume median optical diameter of between about 1.5 μm and about 10 μm, and associate with the first and second species of active agent particles to form a co-suspension. In one such embodiment, at least 90% of the first and second species of active agent particles by volume exhibit an optical diameter of less than 7 μm, and the ratio of the total mass of the suspending particles to the total mass of the first and second species of active agent particles is selected from between about 3:1 and about 15:1 and between about 2:1 and 8:1.

In another embodiment, a co-suspension composition deliverable from a metered dose inhaler according to the present description includes the following: a suspension medium comprising a pharmaceutically acceptable HFA propellant; a first species of active agent particles comprising glycopyrrolate, including any pharmaceutically acceptable salts, esters, isomers or solvates thereof, suspended in the suspension medium at a concentration sufficient to provide a delivered dose of glycopyrrolate of between about 15 μg and about 80 μg per actuation of the metered dose inhaler; a second species of active agent particles comprising formoterol, including any pharmaceutically acceptable salts, esters, isomers or solvates thereof suspended in the suspension medium at a concentration sufficient to provide a delivered dose of formoterol of between about 2 μg and about 10 μg per actuation of the metered dose inhaler; and a plurality of respirable suspending particles comprising perforated microstructures incorporating mometasone, including any pharmaceutically acceptable salts, esters, isomers or solvates thereof, wherein the suspending particles include sufficient mometasone to provide a delivered dose of mometasone of between about 20 μg and about 100 μg per actuation of the metered dose inhaler, exhibit a volume median optical diameter of between about 1.5 μm and about 10 μm, and associate with the first and second species of active agent particles to form a co-suspension. In one such embodiment, at least 90% of the first and second species of active agent particles by volume exhibit an optical diameter of less than 7 μm, and the ratio of the total mass of the suspending particles to the total mass of the first and second species of active agent particles is selected from between about 3:1 and about 15:1 and between about 2:1 and 8:1.

In another embodiment, a co-suspension composition deliverable from a metered dose inhaler according to the present description includes the following: a suspension medium comprising a pharmaceutically acceptable HFA propellant; a first species of active agent particles comprising tiotropium, including any pharmaceutically acceptable salts, esters, isomers or solvates thereof, suspended in the suspension medium at a concentration sufficient to provide a delivered dose of tiotropium of between about 5 μg and about 20 μg per actuation of the metered dose inhaler; a second species of active agent particles comprising formoterol, including any pharmaceutically acceptable salts, esters, isomers or solvates thereof, suspended in the suspension medium at a concentration sufficient to provide a delivered dose of formoterol of between about 2 μg and about 10 μg per actuation of the metered dose inhaler; and a plurality of respirable suspending particles comprising perforated microstructures incorporating a corticosteroid selected from beclomethasone, budesonide, ciclesonide, flunisolide, fluticasone, methyl-prednisolone, mometasone, prednisone and trimacinolone, including any pharmaceutically acceptable salts, esters, isomers or solvates thereof, wherein the suspending particles exhibit a volume median optical diameter of between about 1.5 μm and about 10 μm and associate with the first and second species of active agent particles to form a co-suspension. In one such embodiment, at least 90% of the first and second species of active agent particles by volume exhibit an optical diameter of less than 7 μm, and the ratio of the total mass of the suspending particles to the total mass of the first and second species of active agent particles is selected from between about 3:1 and about 15:1 and between about 2:1 and 8:1.

In another embodiment, a co-suspension composition deliverable from a metered dose inhaler according to the present description includes the following: a suspension medium comprising a pharmaceutically acceptable HFA propellant; a first species of active agent particles comprising tiotropium, including any pharmaceutically acceptable salts, esters, isomers or solvates thereof, suspended in the suspension medium at a concentration sufficient to provide a delivered dose of tiotropium of between about 5 μg and about 20 μg per actuation of the metered dose inhaler; a second species of active agent particles comprising formoterol, including any pharmaceutically acceptable salts, esters, isomers or solvates thereof, suspended in the suspension medium at a concentration sufficient to provide a delivered dose of formoterol of between about 2 μg and about 10 μg per actuation of the metered dose inhaler; and a plurality of respirable suspending particles comprising perforated microstructures incorporating budesonide, including any pharmaceutically acceptable salts, esters, isomers or solvates thereof, wherein the suspending particles include sufficient budesonide to provide a delivered dose of budesonide of between about 30 μg and about 50 μg per actuation of the metered dose inhaler, exhibit a volume median optical diameter of between about 1.5 μm and about 10 μm, and associate with the first and second species of active agent particles to form a co-suspension. In one such embodiment, at least 90% of the first and second species of active agent particles by volume exhibit an optical diameter of less than 7 μm, and the ratio of the total mass of the suspending particles to the total mass of the first and second species of active agent particles is selected from between about 3:1 and about 15:1 and between about 2:1 and 8:1.

In another embodiment, a co-suspension composition deliverable from a metered dose inhaler according to the present description includes the following: a suspension medium comprising a pharmaceutically acceptable HFA propellant; a first species of active agent particles comprising tiotropium, including any pharmaceutically acceptable salts, esters, isomers or solvates thereof, suspended in the suspension medium at a concentration sufficient to provide a delivered dose of tiotropium of between about 5 μg and about 20 μg per actuation of the metered dose inhaler; a second species of active agent particles comprising formoterol, including any pharmaceutically acceptable salts, esters, isomers or solvates thereof, suspended in the suspension medium at a concentration sufficient to provide a delivered dose of formoterol of between about 2 μg and about 10 μg per actuation of the metered dose inhaler; and a plurality of respirable suspending particles comprising perforated microstructures incorporating mometasone, including any pharmaceutically acceptable salts, esters, isomers or solvates thereof, wherein the suspending particles include sufficient mometasone to provide a delivered dose of mometasone of between about 20 μg and about 100 μg per actuation of the metered dose inhaler, exhibit a volume median optical diameter of between about 1.5 μm and about 10 μm, and associate with the first and second species of active agent particles to form a co-suspension. In one such embodiment, at least 90% of the first and second species of active agent particles by volume exhibit an optical diameter of less than 7 μm, and the ratio of the total mass of the suspending particles to the total mass of the first and second species of active agent particles is selected from between about 3:1 and about 15:1 and between about 2:1 and 8:1.

III. Metered Dose Inhaler Systems

As described in relation to the methods provided herein, the co-suspension compositions disclosed herein may be used in an MDI system. MDIs are configured to deliver a specific amount of a medicament in aerosol form. In one embodiment, an MDI system includes a pressurized, liquid phase formulation-filled canister disposed in an actuator formed with a mouthpiece. The MDI system may include the formulations described herein, which include a suspension medium, at least one species of active agent particles and at least one species of suspending particles. The canister used in the MDI may be of any suitable configuration, and in one exemplary embodiment, the canister may have a volume ranging from about 5 mL to about 25 mL, such as, for example a canister having a 19 mL volume. After shaking the device, the mouthpiece is inserted into a patient's mouth between the lips and teeth. The patient typically exhales deeply to empty the lungs and then takes a slow deep breath while actuating the cartridge.

Inside an exemplary cartridge is a metering valve including a metering chamber capable of holding a defined volume of the formulation (e.g., 63 μl or any other suitable volume available in commercially available metering valves), which is released into an expansion chamber at the distal end of the valve stem when actuated. The actuator retains the canister and may also include a port with an actuator nozzle for receiving the valve stem of the metering valve. When actuated, the specified volume of formulation travels to the expansion chamber, out the actuator nozzle and into a high-velocity spray that is drawn into the lungs of a patient.

IV. Methods

Methods of formulating a pharmaceutical composition for respiratory delivery of at least two active agents are provided herein. In one embodiment, the method involves the steps of providing a suspension medium, one or more species of active agent particles and one or more species of suspending particles, and combining such constituents to form a composition wherein the active agent particles associate with the suspending particles and co-locate with the suspending particles within the suspension medium such that a co-suspension as described herein is formed. In one such embodiment, the association of the active agent particles and the suspending particles is such that they do not separate due to their different buoyancies in a propellant. As will be appreciated, a method of formulating a pharmaceutical composition as described herein can include providing two or more species of active agent particles in combination with one or more species of suspending particles. In further embodiments, the method may include providing two or more species of suspending particles in combination with two or more species of active agent particles in a manner which results in a co-suspension. In still other embodiments, one or more species of active agent particles may be combined with one or more species of suspending particles, as described herein. In particular embodiments, the active agent material included in the active agent particles is selected from one or more of LABA, LAMA or corticosteroid active agents. In certain embodiments, the active agent particles consist essentially of active agent material, and are free of additional excipients, adjuvants, stabilizers, etc.

In specific embodiments of methods for providing a stabilized composition of a combination of two or more active agents, the present disclosure provides methods for inhibiting the solution mediated transformation of the active agents in a pharmaceutical composition for pulmonary delivery. In one embodiment, a suspension medium as described herein, such as a suspension medium formed by an HFA propellant, is obtained. Suspending particles are also obtained or prepared as described herein. Active agent particles are also obtained, and the suspension medium, suspending particles and active agent particles are combined to form a co-suspension wherein the active agent particles associate with suspending particles and co-locate with the suspending particles within the continuous phase formed by the suspension medium. When compared to active agent particles contained in the same suspension medium in the absence of suspending particles, co-suspensions according to the present description have been found to exhibit a higher tolerance to solution mediated phase transformation that leads to irreversible crystal aggregation, and thus may lead to improved stability and dosing uniformity.

In further embodiments, methods for forming stabilized compositions including two or more active agents for pulmonary delivery include preserving the FPF and/or FPD of the composition throughout emptying of an MDI canister. In specific embodiments of methods for preserving the FPF and/or FPD provided by a pharmaceutical composition for pulmonary delivery, a respirable co-suspension as described herein is provided which is capable of maintaining the FPD and/or the FPF to within ±20%, ±10%, or even ±5% the initial FPD and/or FPF, respectively, throughout emptying of an MDI canister. Such performance can be achieved where two or more active agents are incorporated into the co-suspension and even after the co-suspension is subjected to accelerated degradation conditions. In one embodiment, a suspension medium as described herein, such as a suspension medium formed by an HFA propellant, is obtained. Suspending particles are also obtained or prepared as described herein. Active agent particles are also obtained, and the suspension medium, suspending particles and active agent particles are combined to form a co-suspension wherein the active agent particles associate with suspending particles and co-locate with the suspending particles within the suspension medium. Even after exposure of such composition to one or more temperature cycling events, the co-suspension maintains an FPD or FPF within ±20%, ±10%, or even ±5% of the respective values measured prior to exposure of the composition to multiple temperature cycling events.

Methods for preparing an MDI for respiratory delivery of two or more active agents are disclosed. In certain embodiments, such a method may include loading a canister, as described herein, with active agent particles and suspending particles. An actuator valve can be attached to an end of the canister and the canister sealed. The actuator valve may be adapted for dispensing a metered amount of the active agents included in the co-suspension composition per actuation of the MDI. The canister can be charged with a pharmaceutically acceptable suspension medium, such as a propellant as described herein, whereupon the active agent particles and suspending particles yield a stable co-suspension in the suspension medium.

In methods involving respiratory delivery of two or more active agents using compositions described herein, the compositions may be delivered by an MDI. Therefore, in particular embodiments of such methods, an MDI loaded with a composition described herein is obtained, and two or more active agents are administered to a patient via respiratory delivery through actuation of the MDI. For example, in one embodiment involving pulmonary delivery of two or more active agents, after shaking the MDI device, the mouthpiece is inserted into a patient's mouth between the lips and teeth. The patient typically exhales deeply to empty the lungs and then takes a slow deep breath while actuating the cartridge of the MDI. When actuated, the specified volume of formulation travels to the expansion chamber, out the actuator nozzle and into a high-velocity spray that is drawn into the lungs of a patient. In one embodiment the dose of each active agent delivered throughout emptying of an MDI canister is not more than 30% greater than the mean delivered dose and is not less than 30% less than the mean delivered dose. Therefore, methods of achieving a desired DDU of two or more active agents delivered from an MDI are also provided. In such embodiments, the method may include achieving a DDU for each of the two or more active agents delivered from an MDI selected from, for example, a DDU of ±30%, or better, a DDU of ±25%, or better, and a DDU of ±20%, or better throughout emptying of the MDI canister from which the co-suspension composition is delivered.

Methods for treating patients suffering from an inflammatory or obstructive pulmonary disease or condition are provided herein. In specific embodiments, such methods include pulmonary delivery of a pharmaceutical composition described herein, and in certain such embodiments, pulmonary administration of the pharmaceutical composition is accomplished by delivering the composition using an MDI. The disease or condition to be treated can be selected from any inflammatory or obstructive pulmonary disease or condition that responds to the administration of, for example, the active agents described herein. In some embodiments, the combination of active agents includes at least one active agent selected from LAMA, LABA or corticosteroid active agents. In particular embodiments, the pharmaceutical compositions described herein may be used in treating a disease or disorder selected from asthma, COPD, exacerbation of airways hyper reactivity consequent to other drug therapy, allergic rhinitis, sinusitis, pulmonary vasoconstriction, inflammation, allergies, impeded respiration, respiratory distress syndrome, pulmonary hypertension, pulmonary vasoconstriction, emphysema, and any other respiratory disease, condition, trait, genotype or phenotype that can respond to the administration of combinations of active agents described herein. In certain embodiments, the pharmaceutical compositions described herein may be used in treating pulmonary inflammation and obstruction associated with cystic fibrosis.

Additionally, pharmaceutical compositions according to the present description delivered from an MDI provide desirable pharmacodynamic (PD) performance. In particular embodiments, pulmonary delivery of the pharmaceutical compositions described herein results in rapid, significant improvement in the lung capacity, which can be characterized by an improvement in the patient's forced expiratory volume in one second ($FEV_1$). For example, in particular embodiments, methods for achieving a clinically significant increase in $FEV_1$ are provided, wherein such methods include providing a co-suspension composition comprising two or more active agents, wherein at least one of those active agents is selected from a LABA, LAMA or corticosteroid active agents, as described herein, and administering such composition to a patient experiencing pulmonary inflammation or obstruction via an MDI. In one such embodiment, the active agents included in the composition include a combination selected from one of a combination of LABA and LAMA active agents, a combination of LABA and corticosteroid active agents, a combination of LAMA and corticosteroid active agents, and a combination of LABA, LAMA and corticosteroid active agents. For purposes of the present disclosure, a clinically significant increase in $FEV_1$ is any increase of 100 ml or greater, and in certain embodiments of the methods described herein, administration of compositions according to the present description to patient results in a clinically significant increase in $FEV_1$ within 1 hour or less. In other such embodiments, methods for administering a composition as described herein to a patient via an MDI result in a clinically significant increase in $FEV_1$ within 0.5 hours or less.

In further embodiments, methods are provided for achieving an increase in $FEV_1$ greater than 100 ml. For example, in certain embodiments, the methods described herein include methods for achieving an $FEV_1$ of 150 ml or greater within a period of time selected from 0.5 hours or less, 1 hour or less, and 1.5 hours or less. In other embodiments, the methods described herein include methods for achieving an $FEV_1$ of 200 ml or greater within a period of time selected from 0.5 hours or less, 1 hour or less, and 1.5 hours or less, and 2 hours or less. In yet other such embodiments, the methods described herein include methods for achieving an $FEV_1$ of 250 ml or greater within a period of time selected from 0.5 hours or less, 1 hour or less, and 1.5 hours or less, and 2 hours or less. In still other such embodiments, the methods described herein include methods for achieving an $FEV_1$ of 300 ml or greater within a period of time selected from 0.5 hours or less, 1 hour or less, and 1.5 hours or less, and 2 hours or less. In yet other such embodiments, the methods described herein include methods for achieving an $FEV_1$ of 350 ml or greater within a period of time selected from 0.5 hours or less, 1 hour or less, and 1.5 hours or less, and 2 hours or less. In certain such embodiments, the active agents included in the composition include a combination selected from one of a combination of LABA and LAMA active agents, a combination of LABA and corticosteroid active agents, a combination of LAMA and corticosteroid active agents, and a combination of LABA, LAMA and corticosteroid active agents, wherein the composition is delivered to the patient via an MDI.

In still further embodiments, methods for achieving and maintaining a clinically significant increase in $FEV_1$ are provided. In particular embodiments, upon administration of a single dose of a combination of active agents formulated in a composition as described herein to a patient via an MDI, a clinically significant increase in $FEV_1$ is achieved in a period of time selected from 0.5 hours or less, 1 hour or less, and 1.5 hours or less, and the clinically significant increase in $FEV_1$ is maintained for up 12 hours or more. In certain such embodiments, the increase in $FEV_1$ may be selected from an increase of 150 ml or greater, 200 ml or greater, 250 ml or greater, 300 ml or greater, and 350 ml or greater, and the increase in $FEV_1$ remains clinically significant for a time period selected from up to 4 hours, up to 6 hours, up to 8 hours, up to 10 hours, and up to 12 hours, or more. In certain such embodiments, the active agents included in the composition include a combination selected from one of a combination of LABA and LAMA active agents, a combination of LABA and corticosteroid active agents, a combination of LAMA and corticosteroid active agents, and a combination of LABA, LAMA and corticosteroid active agents, wherein the composition is delivered to the patient via an MDI.

Compositions, systems and methods described herein are not only suited to achieving desirable pharmacodynamic performance in short periods of time, but will achieve such results in a high percentage of patients. For example, methods are provided herein for achieving a 10% or greater increase in $FEV_1$ in 50% or more of patients experiencing pulmonary inflammation or obstruction. For example, in particular embodiments, methods for achieving a 10% or greater increase in $FEV_1$ in a patient include providing a co-suspension composition comprising a combination of active agents, wherein at least one active agent is selected from LABA, LAMA, and corticosteroid active agents as described herein, and administering such composition via an MDI to a patient experiencing pulmonary inflammation or obstruction. In certain such embodiments, administration of the composition results in 10% or greater increase in $FEV_1$ within a period of time selected from 0.5 hours or less, 1 hour or less, 1.5 hours or less, and 2 hours in 50% or more of patients. In other such embodiments, administration of the composition results in 10% or greater increase in $FEV_1$ within a period of time selected from 0.5 hours or less, 1 hour or less, 1.5 hours or less, and 2 or less hours in 60% or more of patients. In still other such embodiments, administration of the composition results in 10% or greater increase in $FEV_1$ within a period of time selected from 0.5 hours or less, 1 hour or less, 1.5 hours or less, and 2 hours or less in 70% or more of patients. In yet other such embodiments, administration of the composition results in 10% or greater increase in $FEV_1$ within a period of time selected from 0.5 hours or less, 1 hour or less, 1.5 hours or less, and 2 or less hours in 80% or more of patients. In certain such embodiments, the active agents included in the composition include a combination selected from one of a combination of LABA and LAMA active agents, a combination of LABA and corticosteroid active agents, a combination of LAMA and corticosteroid active agents, and a combination of LABA, LAMA and corticosteroid active agents, wherein the composition is delivered to the patient via an MDI.

In specific embodiments, the methods described herein facilitate treatment of patients experiencing pulmonary inflammation or obstruction, wherein such methods include providing a co-suspension composition comprising a combination of active agents as described herein and administering such composition to a patient experiencing pulmonary inflammation or obstruction via an MDI, and administration of the composition via an MDI results in patients experiencing either an increase from baseline in $FEV_1$ of at least 200 ml or a 12%, or greater, increase from baseline in $FEV_1$ coupled with total increase in $FEV_1$ of at least 150 ml. In certain such embodiments, administration of the composition results in either an increase from baseline in $FEV_1$ of at least 200 ml or a 12%, or greater, increase from baseline in $FEV_1$ coupled with total increase in $FEV_1$ of at least 150 ml within a period of time selected from 1 hour, or less, 1.5 hours or less, 2 hours, or less, and 2.5 hours, or less, in 50% or more of patients. In other such embodiments, administration of the composition results in an increase from baseline in $FEV_1$ of at least 200 ml or a 12%, or greater, increase from baseline in $FEV_1$ coupled with total increase in $FEV_1$ of at least 150 ml within a period of time selected from 1 hour, or less, 1.5 hours, or less, 2 hours, or less, and 2.5 hours, or less, in 60% or more of patients. In still other such embodiments, administration of the composition results in either an increase from baseline in $FEV_1$ of at least 200 ml or a 12%, or greater, increase from baseline in $FEV_1$ coupled with total increase in $FEV_1$ of at least 150 ml within a period of time selected from 1.5 hours, or less, 2 hours, or less, 2.5 hours, or less, and 3 hours, or less, in 70% or more of patients. In yet other such embodiments, administration of the composition results in either an increase from baseline in $FEV_1$ of at least 200 ml or a 12%, or greater, increase from baseline in $FEV_1$ coupled with total increase in $FEV_1$ of at least 150 ml within a period of time selected from 1.5 hours, or less, 2 hours, or less, 2.5 hours or less, and 3 hours, or less, in 80% or more of patients. In certain such embodiments, the active agents included in the composition include a combination selected from one of a combination of LABA and LAMA active agents, a combination of LABA and corticosteroid active agents, a combination of LAMA and corticosteroid active agents, and a combination of LABA, LAMA and corticosteroid active agents, wherein the composition is delivered to the patient via an MDI.

In some embodiments, the methods for achieving and maintaining a clinically significant increase in $FEV_1$ described herein result in an increase in $FEV_1$ that represents a significant improvement in $FEV_1$ relative to the improvement provided by compositions delivering only a single active agent. For purposes of comparing the $FEV_1$ performance of a composition described herein with one delivering only a single active agent, a significant improvement in $FEV_1$ is an improvement of 60 ml or greater. For example, in particular embodiments, methods for achieving a significant improvement in $FEV_1$ relative to the improvement provided by compositions delivering only a single active agent include providing a co-suspension composition as described herein comprising a combination of active agents, wherein at least one active agent is selected from LABA, LAMA, and corticosteroid active agents as described herein, and administering such composition via an MDI to a patient experiencing pulmonary inflammation or obstruction. In certain such embodiments, administration of the co-suspension composition results in an improvement in $FEV_1$ $AUC_{0-12}$ of at least 70 ml when compared to the $FEV_1$ $AUC_{0-12}$ achieved by a composition delivering a single active agent. In other such embodiments, administration of the co-suspension composition results in an improvement in $FEV_1$ $AUC_{0-12}$ of at least 80 ml when compared to the $FEV_1$ $AUC_{0-12}$ achieved by a composition delivering a single active agent. In still other embodiments, administration of the co-suspension composition results in an improvement in $FEV_1$ $AUC_{0-12}$ of at least 90 ml when compared to the $FEV_1$ $AUC_{0-12}$ achieved by a composition delivering a single active agent.

In other embodiments, methods for achieving a significant improvement in $FEV_1$ relative to the improvement provided by compositions delivering only a single active agent include providing a co-suspension composition as described herein comprising a combination of active agents, wherein at least one active agent is selected from LABA, LAMA, and corticosteroid active agents as described herein, administering such composition via an MDI to a patient experiencing pulmonary inflammation or obstruction, with such administration resulting in a significant improvement in the peak change in $FEV_1$ (Peak $FEV_1$) when compared to the Peak $FEV_1$ achieved by a composition delivering a single active agent. In certain such embodiments, administration of the co-suspension composition as described herein results in an improvement in Peak $FEV_1$ of at least 70 ml when compared to the Peak $FEV_1$ achieved by a composition delivering a single active agent. In other such embodiments, administration of the co-suspension composition as described herein results in an improvement in Peak $FEV_1$ of at least 80 ml when compared to the Peak $FEV_1$ achieved by a composition delivering a single active agent. In further such embodiments, administration of the co-suspension composition as described herein results in an improvement in Peak $FEV_1$ of at least 90 ml when compared to the Peak $FEV_1$ achieved by a composition delivering a single active agent.

Methods for providing a clinically significant increase in inspiratory capacity (IC) in patients suffering from pulmonary inflammation or obstruction are also provided. As used herein, IC is defined as the maximal volume of gas that can be taken into the lungs in a full inhalation following a normal expiration, and a clinically significant increase in IC is any increase of 70 ml or greater. For example, in particular embodiments, methods for improving IC as described herein include providing a co-suspension composition as described herein comprising a combination of active agents, wherein at least one active agent is selected from LABA, LAMA, and corticosteroid active agents as described herein, and administering such composition via an MDI to a patient experiencing pulmonary inflammation or obstruction, wherein administration of the composition results in an increase in IC of 70 ml or greater. In certain such embodiments, administration of the composition according to the present description results in an increase in IC of 100 ml or greater. In other such embodiments, administration of the composition according to the present description results in an increase in IC of 200 ml or greater. In still other such embodiments, administration of composition according to the present description results in an increase in IC of 300 ml or greater, and in still other embodiments, administration of composition according to the present description results in an increase in IC of 350 ml or greater. In specific such embodiments, the increase in IC is experienced rapidly. For example, in each of the methods described, a clinically significant increase in IC or an increase in IC selected from 100 ml or greater, 200 ml or greater, 300 ml or greater, or 350 ml or greater can be experienced in a patient within a time selected from 1 hour or less and 2 hours or less.

The methods for increasing IC described herein are not only useful for quickly achieving clinically significant increases in IC in a short period of time, but they are useful for maintaining a clinically significant increase in IC over time. For example, as is highlighted by the clinical results presented in Example 12, the clinically significant increases in IC provided by the methods described herein are experienced by patients quickly after administration, the increases in IC remain clinically significant for a period of up to 12 hours or more post-administration, and the increases in IC remain clinically significant even after chronic dosing (e.g., multiple consecutive dosing days).

Additionally, compositions according to the present description provide increases in IC that are significantly greater than increases in IC provided by compositions delivering only a single active agent. In embodiments of the methods described herein for increasing IC, administration of a co-suspension composition as described herein provides an increase in IC that is at least 70 ml greater than the increase in IC provided by a composition delivering only a single active agent. In one such embodiment, the increase in IC provided by administering a co-suspension composition described herein is at least 100 ml greater than the increase in IC provided by a composition delivering only a single active agent. In another such embodiment, the increase in IC provided by administering a co-suspension composition described herein is at least 125 ml greater than the increase in IC provided by a composition delivering only a single active agent In some embodiments, the methods described herein for achieving desired pharmacodynamic effects are characterized by delivery of relatively low amounts of active agents. In certain such embodiments, for example, the methods described herein for achieving clinically significant increases in $FEV_1$ include administering a co-suspension as described herein comprising a combination of glycopyrrolate and formoterol active agents, wherein the co-suspension is administered to a patient via a metered dose inhaler up to two times daily and with each administration a total delivered dose of glycopyrrolate of no more than 150 µg and a total delivered dose of formoterol of no more than 12 ug are administered to the patient. In other such embodiments, the methods described herein for achieving clinically significant increases in FEV$_1$ include administering a co-suspension as described herein comprising a combination of glycopyrrolate and formoterol active agents, wherein the co-suspension is administered to a patient via a metered dose inhaler up to two times daily and with each administration a total delivered dose of glycopyrrolate of no more than 100 μg and a total delivered dose of formoterol of no more than 12 ug are administered to the patient. In other such embodiments, the methods described herein for achieving clinically significant increases in FEV$_1$ include administering a co-suspension as described herein comprising a combination of glycopyrrolate and formoterol active agents, wherein the co-suspension is administered to a patient via a metered dose inhaler up to two times daily and with each administration a total delivered dose of glycopyrrolate of no more than 80 μg and a total delivered dose of formoterol of no more than 12 ug are administered to the patient. In still other embodiments, the methods described herein for achieving clinically significant increases in FEV$_1$ include administering a co-suspension as described herein comprising a combination of glycopyrrolate and formoterol active agents, wherein the co-suspension is administered to a patient via a metered dose inhaler up to two times daily and with each administration a total delivered dose of glycopyrrolate of no more than 50 μg and a total delivered dose of formoterol of no more than 12 ug are administered to the patient.

In some embodiments, the methods for achieving clinically significant increases in IC described herein include administering a co-suspension composition as described herein to a patient via a metered dose inhaler, wherein the co-suspension includes glycopyrrolate and formoterol active agents, the co-suspension is administered to a patient via a metered dose inhaler up to two times daily, and with each administration total delivered doses of no more than 150 μg glycopyrrolate and 12 ug formoterol are administered to the patient. In certain such embodiments, for example, the methods described herein for achieving clinically significant increases in IC include administering a co-suspension as described herein comprising a combination of glycopyrrolate and formoterol active agents, wherein the co-suspension is administered to a patient via a metered dose inhaler up to two times daily and with each administration a total delivered dose of glycopyrrolate of no more than 100 μg and a total delivered dose of formoterol of no more than 12 ug are administered to the patient. In other such embodiments, the methods described herein for achieving clinically significant increases in IC include administering a co-suspension as described herein comprising a combination of glycopyrrolate and formoterol active agents, wherein the co-suspension is administered to a patient via a metered dose inhaler up to two times daily and with each administration a total delivered dose of glycopyrrolate of no more than 80 μg and a total delivered dose of formoterol of no more than 12 ug are administered to the patient. In still other embodiments, the methods described herein for achieving clinically significant increases in IC include administering a co-suspension as described herein comprising a combination of glycopyrrolate and formoterol active agents, wherein the co-suspension is administered to a patient via a metered dose inhaler up to two times daily and with each administration a total delivered dose of glycopyrrolate of no more than 50 μg and a total delivered dose of formoterol of no more than 12 ug are administered to the patient.

The compositions provided and delivered in the methods described herein may include a co-suspension composition including any combination of active agents as described herein. For example, in particular embodiments, the methods described herein for achieving a clinically significant increase in FEV$_1$ or IC include providing a co-suspension composition comprising two or more active agents, wherein at least one of those active agents is selected from a LABA, LAMA or corticosteroid active agents as described herein, and administering such composition to a patient experiencing pulmonary inflammation or obstruction via an MDI. In one such embodiment, the active agents included in the co-suspension composition include a combination selected from one of a combination of LABA and LAMA active agents, a combination of LABA and corticosteroid active agents, a combination of LAMA and corticosteroid active agents, and a combination of LABA, LAMA and corticosteroid active agents. In specific embodiments of the methods described herein, the co-suspension composition provided and administered can be any of the specific co-suspension compositions detailed herein.

The specific examples included herein are for illustrative purposes only and are not to be considered as limiting to this disclosure. Moreover, the compositions, systems and methods disclosed herein have been described in relation to certain embodiments thereof, and many details have been set forth for purposes of illustration, it will be apparent to those skilled in the art that the invention is susceptible to additional embodiments and that certain of the details described herein may be varied without departing from the basic principles of the invention. Any active agents and reagents used in the following examples are either commercially available or can be prepared according to standard literature procedures by those skilled in the art of organic synthesis. The entire contents of all publications, patents, and patent applications referenced herein are hereby incorporated herein by reference.

EXAMPLE 1

An exemplary co-suspension composition as described herein was prepared and evaluated. The composition included a combination of glycopyrrolate (GP) and formoterol fumarate (FF) active agents. GP was present in the propellant as micronized, crystalline active agent particles. It was co-suspended with spray dried suspending particles that included FF disposed within the material forming the suspending particle. To achieve this, FF was dissolved in the feedstock used to manufacture the lipid-based suspending particles.

GP active agent particles were formed by micronizing glycopyrrolate using a jet mill. The particle size distribution of the glycopyrrolate active agent particles was determined by laser diffraction using a laser diffraction particle size analyzer, Fraunhofer diffraction mode, equipped with a dry powder dispenser (e.g., Sympatec GmbH, Clausthal-Zellerfeld, Germany). 50% by volume of the active agent particles exhibited an optical diameter smaller than 1.7 μm, and 90% by volume exhibited an optical diameter smaller than 3.5 μm.

FF-containing suspending particles were manufactured as follows: 654 mL of a fluorocarbon-in-water emulsion of PFOB (perfluorooctyl bromide) stabilized by a phospholipid was prepared; 26.5 g of the phospholipid, DSPC (1,2-distearoyl-sn-glycero-3-phosphocholine), and 2.4 g of calcium chloride were homogenized in 276 mL of hot water (80° C.) using a high shear mixer; and 142 mL of PFOB were added slowly during homogenization. The resulting coarse emulsion was then further homogenized using a high pressure homogenizer (Model C3, Avestin, Ottawa, Calif.) at pressures of up to 170 MPa for 5 passes. 552 mg FF was dissolved in 273 ml of warm water (50° C.) and most of the solution was combined with the emulsion using a high shear mixer. The emulsion was spray dried in nitrogen using the following spray drying conditions: inlet temperature 95° C.; outlet temperature 68° C.; emulsion feed rate 2.4 ml/min; and total gas flow 498 l/min. The final mass fraction of formoterol in the spray dried powder was 2%.

A second lot of FF-containing suspending particles was manufactured in a similar fashion. The mass fraction of FF in the spray dried powder was 1% for this lot. A third lot of suspending particles was manufactured without FF.

The particle size distribution of the suspending particles (VMD) was determined by laser diffraction. For both lots of FF containing suspending particles, 50% by volume were smaller than 3.5 μm and the Geometric Standard Deviation of the distribution was 1.7. For the suspending particles without FF, 50% by volume were smaller than 3.2 μm and the Geometric Standard Deviation of the distribution was 1.8.

MDIs containing FF, GP or both were prepared by weighing the target masses of active agent particles and suspending particles into fluorinated ethylene polymer (FEP) coated aluminum canisters (Presspart, Blackburn, UK) with a 19 mL volume. The canisters were crimp sealed with 63 μl valves (# BK 357, Bespak, King's Lynn, UK) and filled with 12.4 g of HFA 134a (1,1,1,2-tetrafluoroethane) (Ineos Fluor, Lyndhurst, UK) by overpressure through the valve stem. The resulting suspension concentrations and the target delivered dose assuming 20% actuator deposition are given in Table 1a for three different configurations (configurations 1A through 1C). After injecting the propellant, the canisters were sonicated for 15 seconds and agitated on a wrist action shaker for 30 minutes. The canisters were fitted with polypropylene actuators with a 0.3 mm orifice (# BK 636, Bespak, King's Lynn, UK).

TABLE 1a

Configurations of the glycopyrrolate - formoterol fumarate combination co-suspensions of Example 1

| # | Suspending Particle 1 GP $C_S$ [mg/ml] | Suspending Particle 1 FF content | $C_S$ [mg/ml] | Suspending Particle 2 $C_S$ [mg/ml] | Suspending Particle to Active Particle Ratio | Ex actuator dose GP [μg] | Ex actuator dose FF [μg] |
|---|---|---|---|---|---|---|---|
| 1A | 0.48 | 1.9% | 3.2 | — | 6.7 | 24 | 3.2 |
| 1B |  | 1% | 6.4 | — | 13.3 |  |  |
| 1C |  | 1.9% | 3.2 | 3.2 | 13.3 |  |  |

The filled MDIs were stored valve down at two different conditions: refrigerated at 5° C. without overwrap and controlled room temperature at 25° C./60% RH with a foil overwrap. Aerosol performance and delivered dose uniformity tests were carried out at different time points. Aerosol performance was assessed after manufacturing in accordance with USP <601> (United States Pharmacopoeia Monograph 601). A Next Generation Impactor (NGI) operated at a flow rate of 30 l/min was used for determination of particle size distribution. Sample canisters were seated into an actuator with two waste actuations and two additional waste priming actuations. Five actuations were collected in the NGI with a USP throat attached. The valve, actuator, throat, NGI cups, stages, and filter were rinsed with volumetrically dispensed solvent. The sample solutions were assayed using a drug-specific chromatographic method. The fine particle fraction was defined using the sum of stages 3 through filter. Delivered dose uniformity through use testing was performed using a Dose Uniformity Sampling Apparatus as described by USP <601>. Inhalers were seated and primed as described before. Two actuations were collected and assayed at beginning, middle and end of use.

No trends in aerosol performance or delivered dose uniformity were observed for the duration of the study (3 months) or as a function of storage temperature. Hence, all aerosol performance test results were pooled. Table 1b lists the average performance of the different configuration. The fine particle dose is the sum of collected mass on stages 3 to filter of the impactor, normalized by the metered dose. The average aerosol performance for all three configurations was equivalent.

TABLE 1b

Average aerosol performance for co-suspensions in Example 1

| # | MMAD in μm FF | MMAD in μm GP | FPD in % FF | FPD in % GP |
|---|---|---|---|---|
| 1A | 2.8 | 3.4 | 52 | 44 |
| 1B | 2.9 | 3.6 | 51 | 45 |
| 1C | 2.9 | 3.6 | 51 | 45 |

Figure 2:
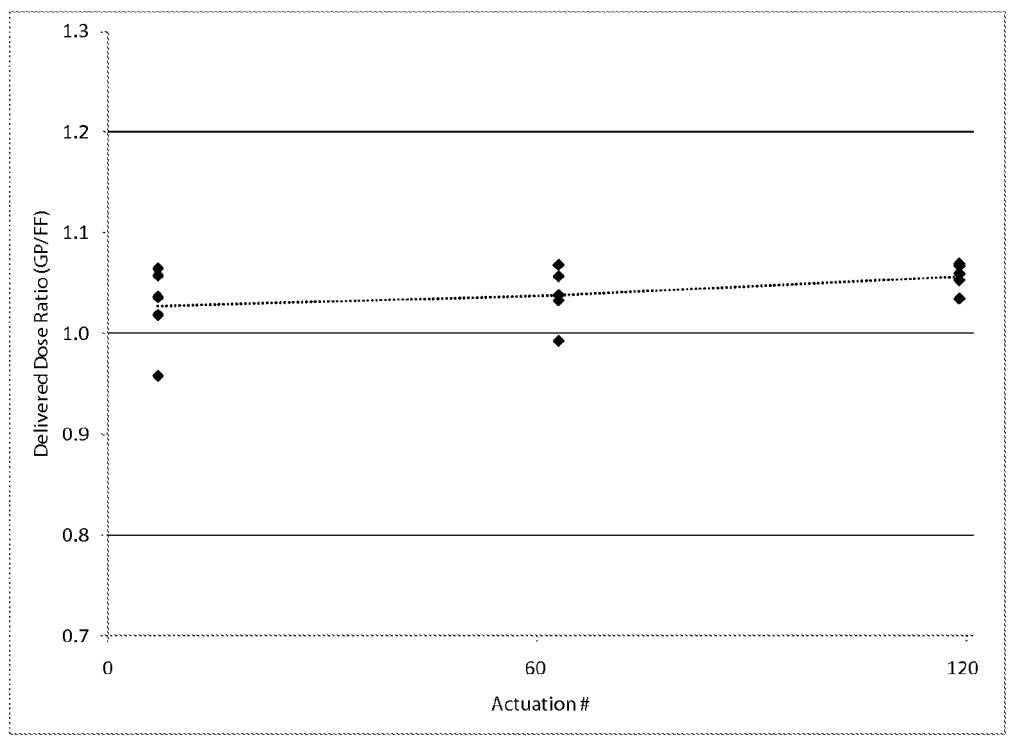
FIG. 2 is a graph, which depicts the delivered dose ratio of the co-suspension formulation of FIG. 1.
Figure 3:
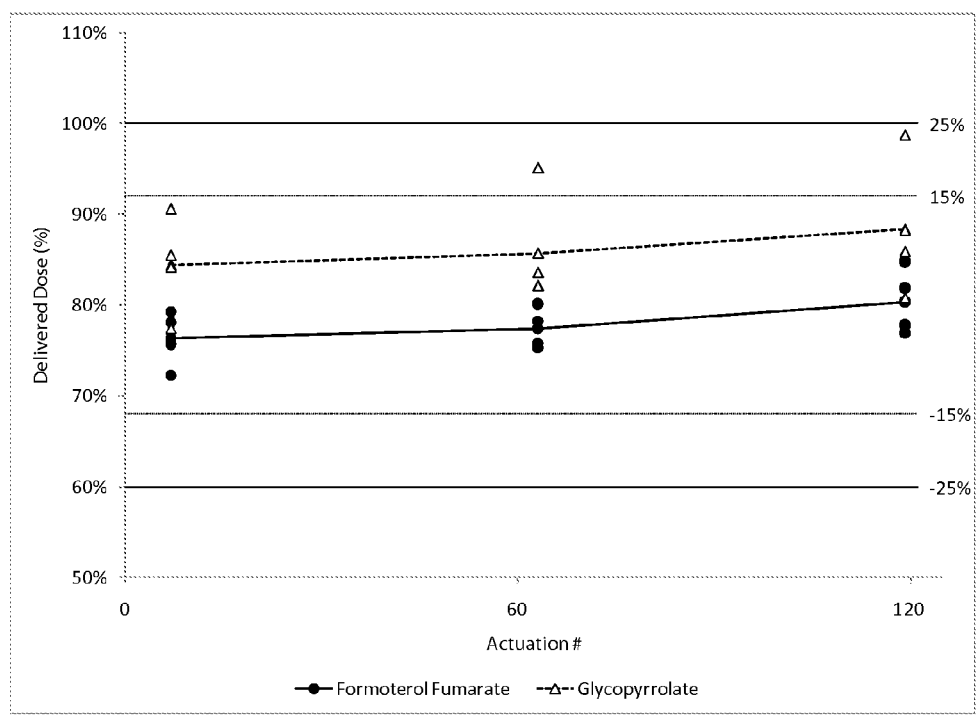
FIG. 3 is a graph, which depicts the delivered dose uniformity of a second co-suspension formulation prepared according to the present description
Figure 4:
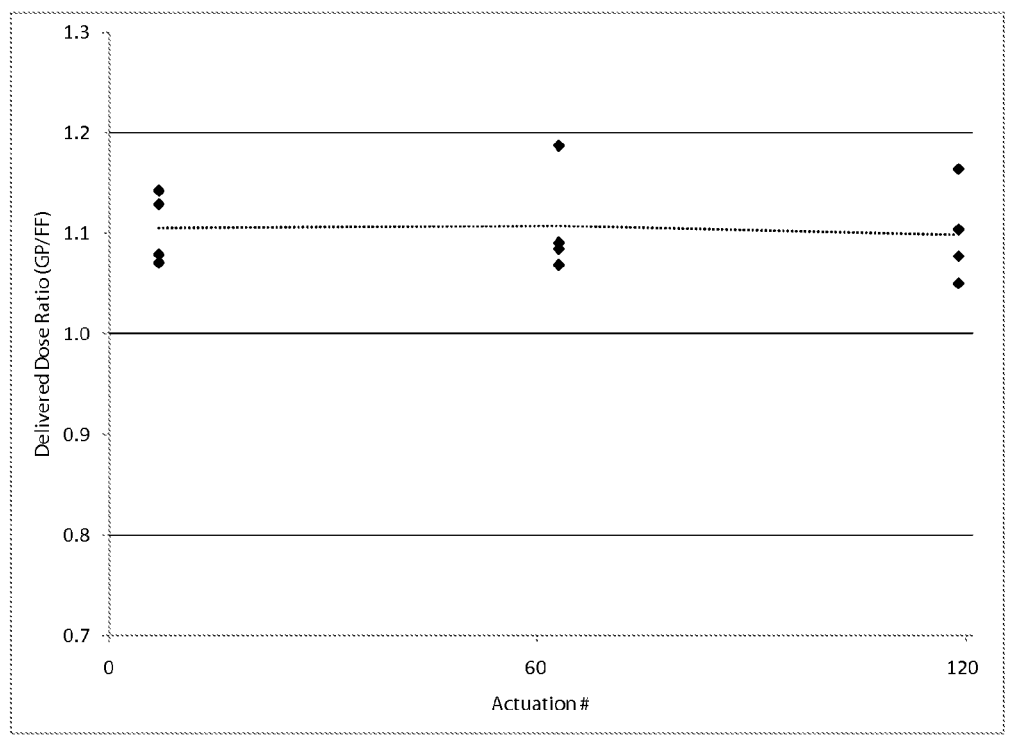
FIG. 4 is a graph, which depicts the delivered dose ratio of the second co-suspension formulation of FIG. 3.

Dose content uniformity was tested through canister life for both actives of the combination product. FIGS. 1 and 2 show the ex-actuator dose for configuration 1A and 1B, respectively, normalized by the actual metered doses of the canister. Assuming an actuator deposition of 20% the target ex-actuator doses for both actives were 80%. The individual FF and GP doses are represented by dots and triangles, respectively. The closed line denotes the mean of the formoterol doses, and the broken line denotes the mean of the glycopyrrolate doses. FIGS. 3 and 4 show the ratio of the normalized ex actuator doses for configuration 1A and 1B, respectively. The result indicates that the dose ratio remained constant through canister life. Furthermore the variability of the dose ratio is much lower than that of the individual doses, indicating that a co-suspension with a consistent carrier to active ratio was formed and maintained through container life.

The results show that, when formulated according to the disclosure provided herein, combination product co-suspensions are formed with suspending particles containing one of the active pharmaceutical ingredients, in this case FF. Suspending particle to active agent particle ratios can be adjusted to achieve targeted dose content uniformity while maintaining similar aerosol performance.

EXAMPLE 2

MDIs containing FF, GP or both were prepared at target concentrations of 2.4 and 18 μg per actuation for FF and GP respectively. GP active agent was micronized and had a $d_{10}$, $d_{50}$, $d_{90}$ and span of 0.6, 1.7, 3.6 and 1.9 μm respectively as measured by laser diffraction as described Example 1. FF was incorporated into spray dried suspending particles and prepared as described in Example 1, with a composition of 2% FF, 91.5% DSPC and 6.5% $CaCl_2$. The GP, FF and GP+FF MDIs were prepared by weighing the target masses of active agent particles and suspending particles into fluorinated ethylene polymer (FEP) coated aluminum canisters (Presspart, Blackburn, UK) with a 19 mL volume. The canisters were crimp sealed with 50 μl valves (# BK 357, Bespak, King's Lynn, UK) and filled with 10.2 g of HFA 134a (1,1,1,2-tetrafluoroethane) (Ineos Fluor, Lyndhurst, UK) by overpressure through the valve stem. After injecting the propellant, the canisters were sonicated for 15 seconds and agitated on a wrist action shaker for 30 minutes. The canisters were fitted with polypropylene actuators with a 0.3 mm orifice (# BK 636, Bespak, King's Lynn, UK).

Figure 5:
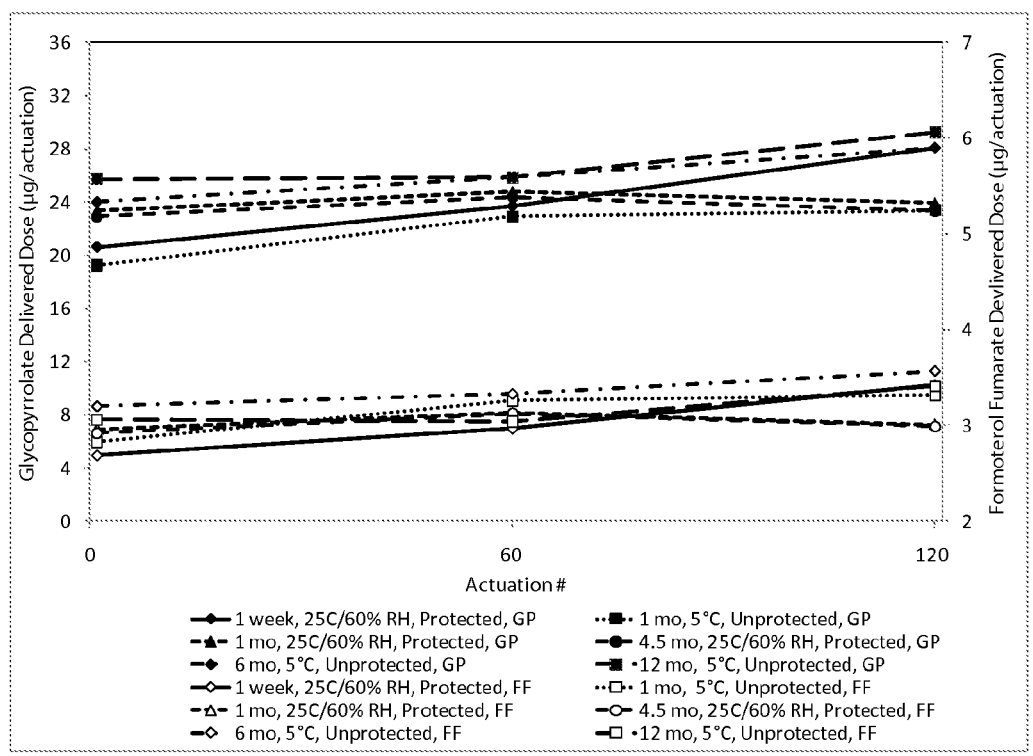
FIG. 5 is a graph, which depicts the delivered dose uniformity of glycopyrrolate and formoterol fumarate in a co-suspension formulation prepared according to the present description upon storage under different conditions as indicated.

Long term aerosol stability and delivery characteristics of the MDI compositions were assessed. In particular the aerosol particle size distribution and delivered dose characteristics of such compositions were evaluated as in accordance with USP <601> as described in Example 1, under various conditions and, in some instances, for periods of time extending up to 12 months. For example, as is shown in FIG. 5, the delivered dose uniformity provided by the compositions prepared according to Example 1 was substantially preserved, even after 12 months storage of such compositions at 5° C. or after 4.5 months at 25° C. and 60% relative humidity (RH) for samples stored inside aluminum foil pouches to minimize water ingress into the MDI canister (i.e., "protected storage").

Figure 6:
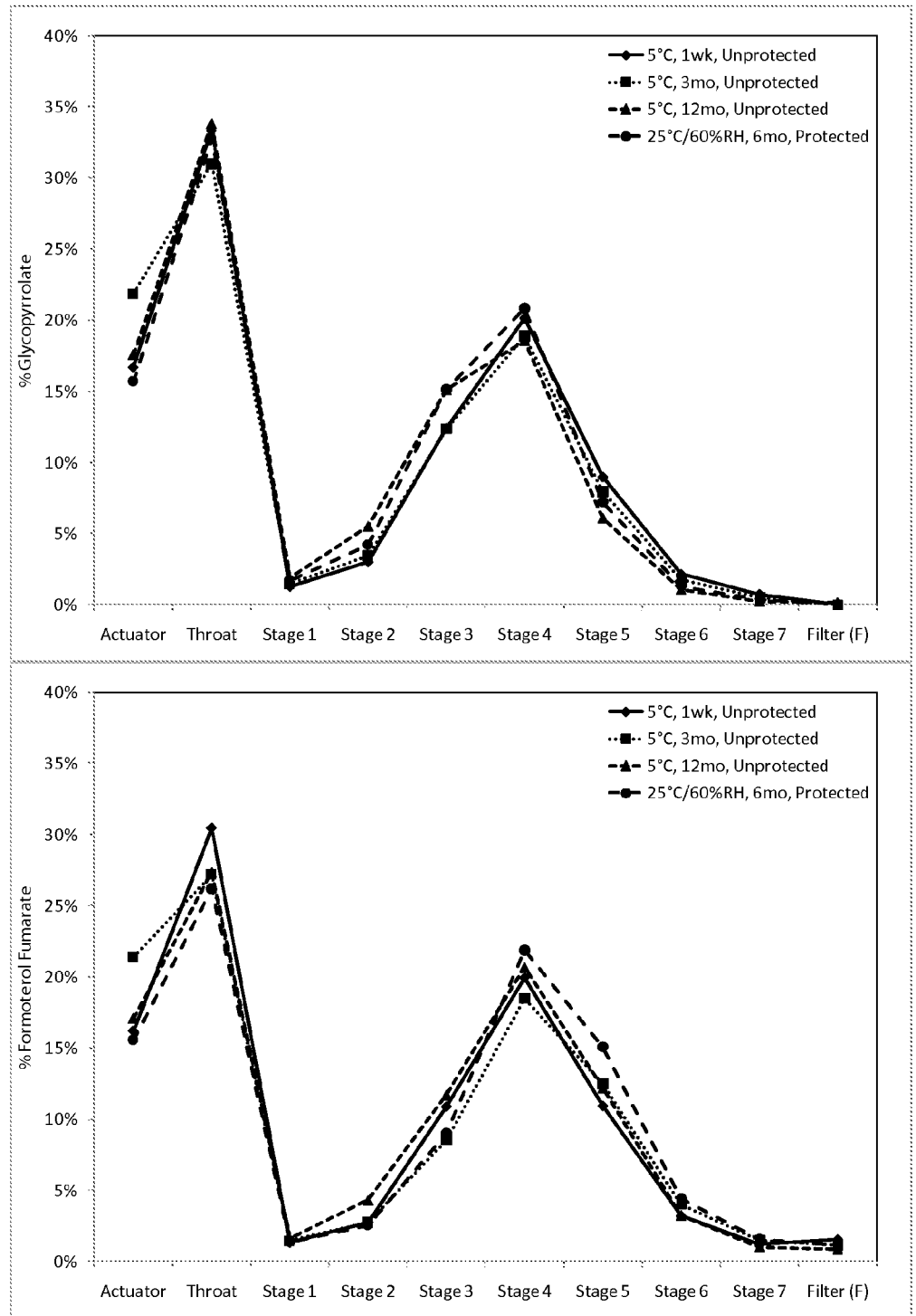
FIG. 6 is a graph, which depicts the particle size distributions of exemplary co-suspension formulations prepared according to the present description upon storage under different conditions, as indicated.
Figure 7:
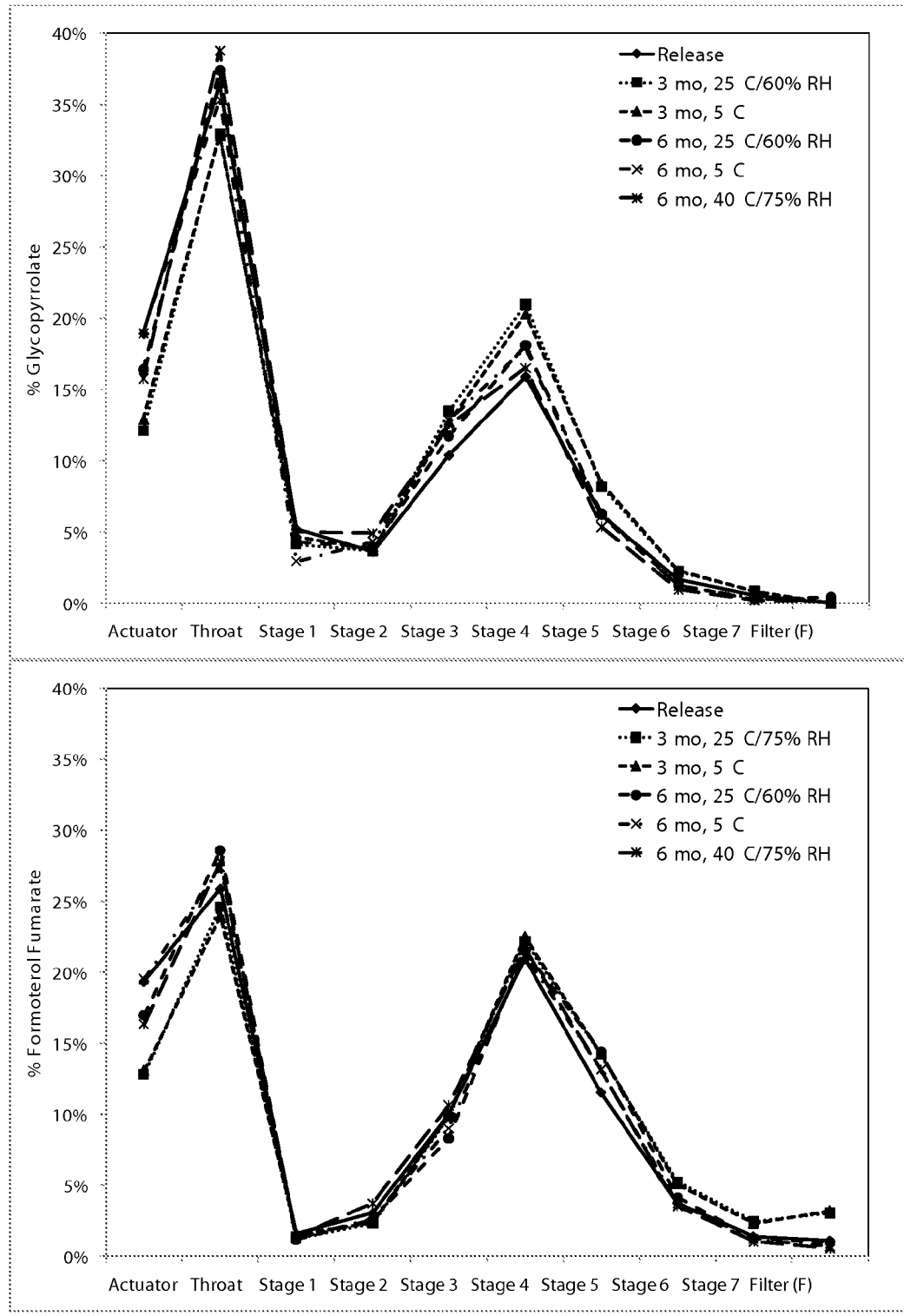
FIG. 7 provides graphs illustrating the particle size distributions achieved by an exemplary co-suspension including a combination of glycopyrrolate and formoterol fumarate, upon storage at indicated conditions.

The aerosol performance of such compositions was also evaluated throughout unprotected storage conditions extending up to 12 months and protected storage conditions extending up to 6 months. As is shown in FIG. 6, the GP and FF particle size distributions provided by this co-suspension composition were substantially preserved after 12 months of protected storage at 5° C. and six months of unprotected storage conditions at 25° C. and 60% RH. As is shown in FIG. 7, even under stressed conditions (40° C., 75% RH), the compositions showed no noticeable degradation in the particle size distribution of GP and FF delivered from the metered dose inhalers after six months.

In order to evaluate whether the combination of GP and FF within a single formulation would result in the degradation of the aerosol properties relative to compositions including a single active agent, the aerosol properties of co-suspension compositions were assessed relative to suspension compositions including only a single active agent.

Figure 8:
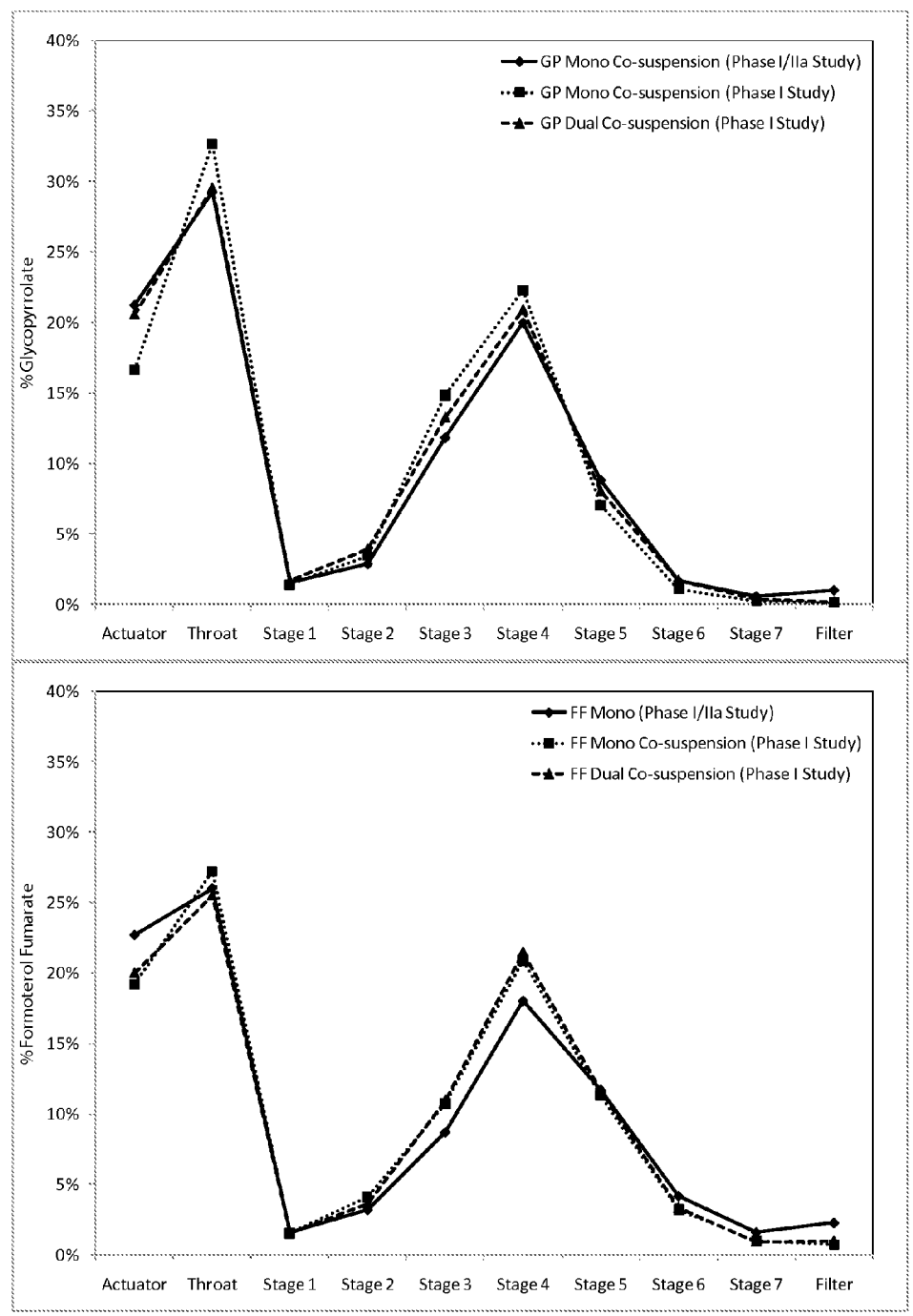
FIG. 8 provides graphs illustrating the particle size distribution achieved by an exemplary co-suspension including a combination of glycopyrrolate and formoterol fumarate compared to particle size distributions achieved by formulations including either glycopyrrolate or formoterol fumarate alone.

As can be seen in FIG. 8, the aerosol performance of the combination co-suspension composition including both GP and FF active agent was no different than the aerosol performance achieved by suspension compositions including either GP or FF alone demonstrating that the aerosol properties of the individual active agents are substantially the same when achieved from the single component or dual combination co-suspensions.

EXAMPLE 3

The pharmacokinetics and safety of a combination co-suspension metered dose inhaler containing glycopyrrolate and formoterol fumarate were evaluated in a clinical trial. The clinical trial was a single-center, randomized, double-blind, single dose, four-period, four-treatment crossover study used to evaluate four inhaled treatments administered by MDI. The four treatments included a Formoterol Fumarate (FF) Inhalation Aerosol, a Glycopyrrolate (GP) Inhalation Aerosol, a GP+FF Inhalation Aerosol, and consecutive delivery of the GP Inhalation Aerosol followed immediately by delivery of the FF Inhalation Aerosol. The GP+FF Inhalation Aerosol as well as the FF Inhalation Aerosol and GP Inhalation Aerosol were prepared as described in Example 2. The GP+FF Inhalation Aerosol was also labeled the "fixed" combination of GP and FF, while the treatment calling for consecutive delivery of the GP Inhalation Aerosol followed immediately by delivery of the FF Inhalation Aerosol was labeled the "loose" combination of GP and FF.

Subjects were randomized in to the study and assigned one of four treatment sequences, with each treatment sequence including all four study treatments. Each subject received four single dose treatments separated by 7 to 21 days. Sixteen subjects were enrolled and analyzed for safety. Three subjects were excluded from the PK analysis as a result of not receiving one or more of the four treatments, and an additional two subjects were excluded from the PK analysis as non-evaluable due to dosing errors arising from poor inhalation technique.

The GP+FF Inhalation Aerosol was administered to provide each subject a 72 µg dose of GP and a 9.6 µg dose of FF (four actuations, 18 µg GP and 2.4 µg FF per actuation). The GP Inhalation Aerosol was administered to provide each subject a 72 µg dose of GP (four actuations, 18 µg GP per actuation). The FF Inhalation Aerosol was administered to provide each subject a 9.6 µg dose of FF (four actuations, 2.4 µg FF per actuation). For blinding purposes each of the preceding three treatments were preceded by four actuations of placebo MDI. The loose combination of GP Inhalation Aerosol followed by FF Inhalation Aerosol was administered to provide each subject a 72 µg dose of GP and a 9.6 µg dose of FF (four actuations, 18 µg GP per actuation followed by four additional actuations, 2.4 µg FF per actuation).

Figure 9:
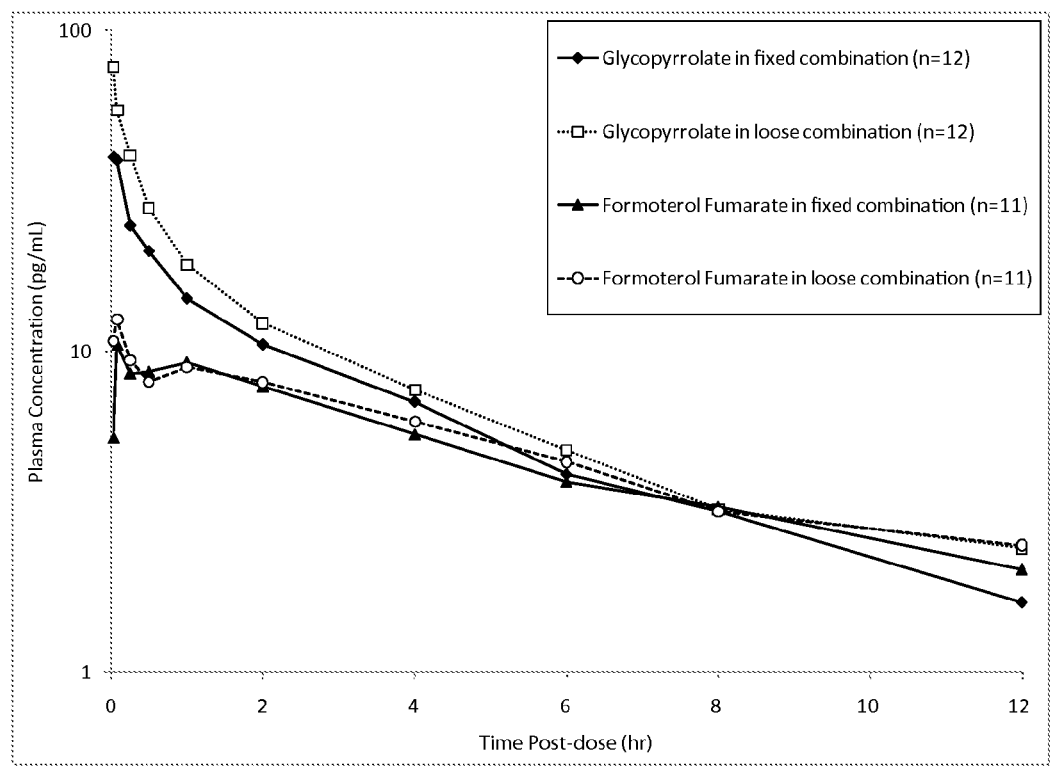
FIG. 9 is a graph, which depicts the serum glycopyrrolate and formoterol concentration levels over time achieved after delivery of an exemplary co-suspension including glycopyrrolate and formoterol fumarate prepared according to the present description. The serum concentration time profile of glycopyrrolate and formoterol fumarate delivered from the exemplary combination formulation is compared to that achieved by compositions containing and delivering glycopyrrolate or formoterol fumarate alone.

Both the loose and fixed combinations of GP and FF were safe and well-tolerated, with the fixed combination providing a safety profile similar to that observed for the other three treatments evaluated in the trial. Blood samples were collected pre-dose and at 2, 5, 15, and 30 minutes, as well as 1, 2, 4, 6, 8, and 12 hours post-dose for determining the plasma concentrations of GP and FF that were used to calculate various PK parameters. Plasma concentration time profiles for both GP and FF in the 12 hour period immediately following dosing are provided in FIG. 9. As can be seen in FIG. 9, administration of GP and FF from the fixed combination resulted in plasma concentrations of GP and FF following administration comparable to those resulting from administration of the loose combination of GP and FF. As was noted for the in-vitro delivered dose and particle size distribution performance described in Example 2, no combination effect was observed in-vivo for the fixed combination GP+FF Inhalation Aerosol.

EXAMPLE 4

An exemplary dual co-suspension composition according to the present description was produced and metered dose inhalers incorporating the composition were prepared. The composition included a combination of glycopyrrolate (GP) and formoterol fumarate (FF), with each being provided as a micronized, crystalline material. A combination crystalline co-suspension MDI was manufactured by semi-automated suspension filling. The dual co-suspension consisted of a combination of two microcrystalline active pharmaceutical ingredients (also referred to as "APIs" or "API" in the singular), GP and FF, co-suspended with suspending particles in HFA 134a propellant. The dual co-suspension was formulated to provide a delivered dose of 18 µg GP per actuation and 4.8 µg FF per actuation. In preparing the dual co-suspension compositions, in certain compositions, the FF API material used was denoted as "coarse", while in other compositions, the FF API material used was denoted as "fine." Whether the co-suspension compositions incorporated course or fine FF, the compositions were formulated to provide a delivered FF dose of 4.8 µg per actuation. The particle size characteristics for the course FF, fine FF and GP API materials used in formulation the co-suspension compositions described in this Example are detailed in Table 2. In addition to the dual co-suspension compositions, a monotherapy co-suspension composition incorporating only FF active agent material was formulated. The FF monotherapy co-suspension utilized coarse FF API. A monotherapy MDI was manufactured using such FF monotherapy co-suspension, and the FF monotherapy MDI was formulated and manufactured provide a delivered dose of 4.8 µg FF per actuation.

Suspending particles were manufactured via spray dried emulsion at a feed stock concentration of 80 mg/mL with a composition of 93.44% DSPC (1,2-Distearoyl-sn-Glycero-3-Phosphocholine) and 6.56% anhydrous calcium chloride (equivalent to a 2:1 DSPC:$CaCl_2$ mole/mole ratio). During the emulsion prep, DSPC and $CaCl_2$ was dispersed with a high shear mixer at 8000-10000 rpm in a vessel containing heated water (80±3° C.) with PFOB slowly added during the process. The emulsion was then processed with 6 passes in a high pressure homogenizer (10000-25000 psi). The emulsion was then spray dried via a spray dryer fitted with a 0.42" atomizer nozzle with a set atomizer gas flow of 18 SCFM. The drying gas flow rate was set to 72 SCFM with an inlet temperature of 135° C., outlet temperature 70° C., and an emulsion flow rate of 58 mL/min.

For the MDI manufacturing, a drug addition vessel (DAV) was prepared for suspension filling in the following manner: first adding half of suspending particle quantity, next filling microcrystalline materials, and lastly adding the remaining half of suspending particles to the top. Materials were added to the vessel in a humidity controlled environment of <10% RH. The DAV was then connected to a 4 L suspension vessel and flushed with HFA 134a propellant and then mixed with gently to form a slurry. The slurry is then transferred back to the suspension mixing vessel and diluted with additional HFA-134a to form the final suspension at target concentration stirring gently with an impeller. The temperature inside the vessel was maintained at 21-23° C. throughout the entire batch production. After recirculation for 30 min the suspension was filled into 14 mL fluorinated ethylene polymer (FEP) coated aluminum canisters (Presspart, Blackburn, UK) through 50 μl valves (Bespak, King's Lynn, UK). Sample canisters were the selected at random for total canister analysis to ensure correct formulation quantities. The optical diameter and particle size distribution of two lots of micronized formoterol particles was determined by laser diffraction as described in Example 1. Table 2 lists the $d_{10}$, $d_{50}$ and $d_{90}$ values for the different lots of micronized material used. $d_{10}$, $d_{50}$ and $d_{90}$ denote the particle size at which the cumulative volume distribution reported by the particle sizing instrument reaches 10%, 50% and 90%, respectively.

The particle size distributions provided by both dual co-suspension formulations prepared in accordance with this Example 4 were compared to the particle size distribution provided by a co-suspension compositions prepared according to Example 1. The results of this comparison are provided in Table 3, where "% FPF FF" and "% FPF GP" represent the fine particle mass of the specified active agent on Stages 3 through filter of an NGI, divided by actuator mass, and multiplied by 100.

TABLE 2

Particle Size Distributions for micronized Formoterol Fumarate and Glycopyrrolate used to prepare Dual Co-Suspensions

| Designation | $d_{10}$ (μm) | $d_{50}$ (μm) | $d_{90}$ (μm) | Span |
|---|---|---|---|---|
| Coarse FF API | 0.6 | 1.9 | 4.4 | 2.0 |
| Fine FF API | 0.5 | 1.3 | 2.3 | 1.5 |
| GP API | 0.5 | 1.3 | 3.0 | 1.9 |

TABLE 3

Particle Size Distributions for Different, Exemplary GP/FF Co-suspensions

| | MMAD FF | % FPF FF | MMAD GP | % FPF GP | MMAD DSPC | % FPF DSPC |
|---|---|---|---|---|---|---|
| Dual Co-Suspension 1 (FF coarse) | 3.4 | 59% | 2.9 | 65% | 2.9 | 64% |
| Dual Co-Suspension 2 (FF fine) | 2.7 | 62% | 3.0 | 62% | 3.1 | 62% |
| Spray-dried FF | 2.7 | 66% | 2.9 | 65% | not tested | not tested |

Figure 10:
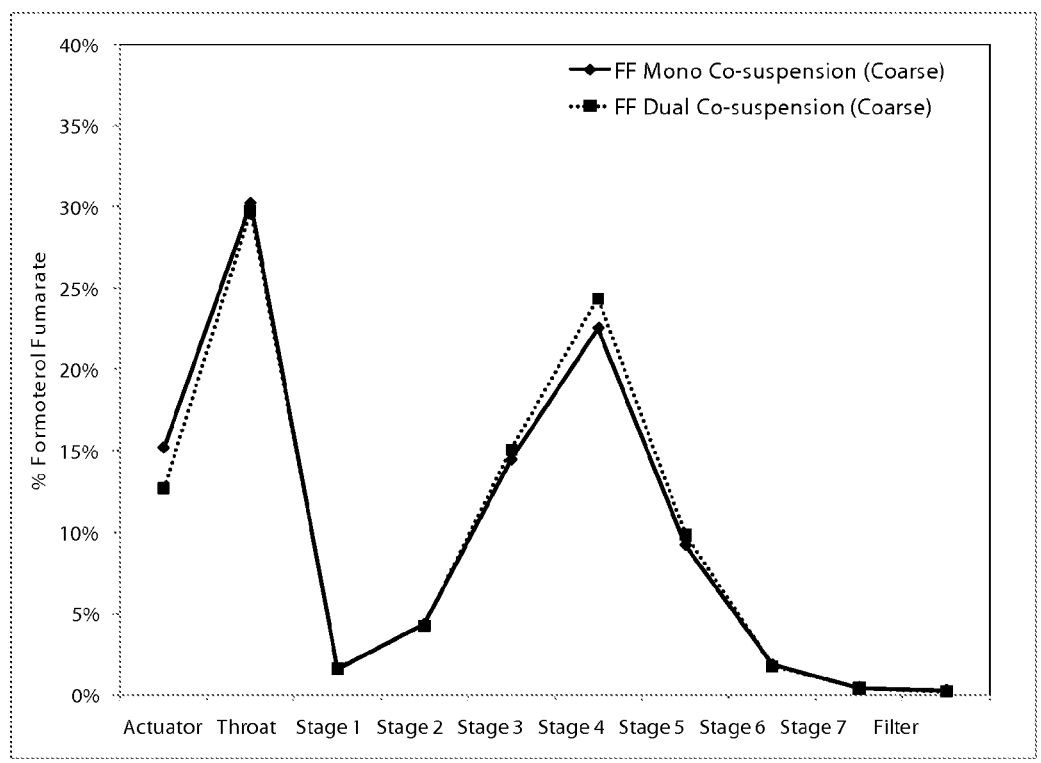
FIG. 10 is a graph that depicts the formoterol particle size distribution achieved by a dual co-suspension prepared according to the present description, which included microcyrstalline formoterol fumarate and glycopyrrolate active agent particles compared to a co-suspension only containing crystalline formoterol fumarate.
Figure 11:
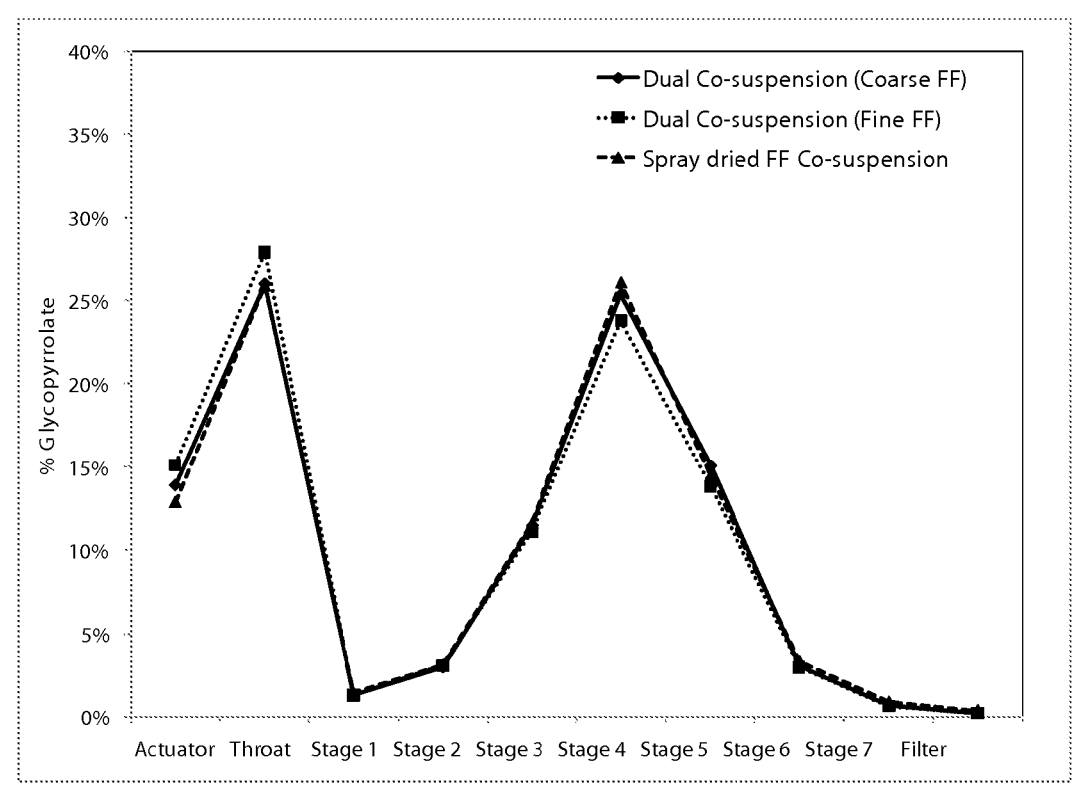
Figure 12:
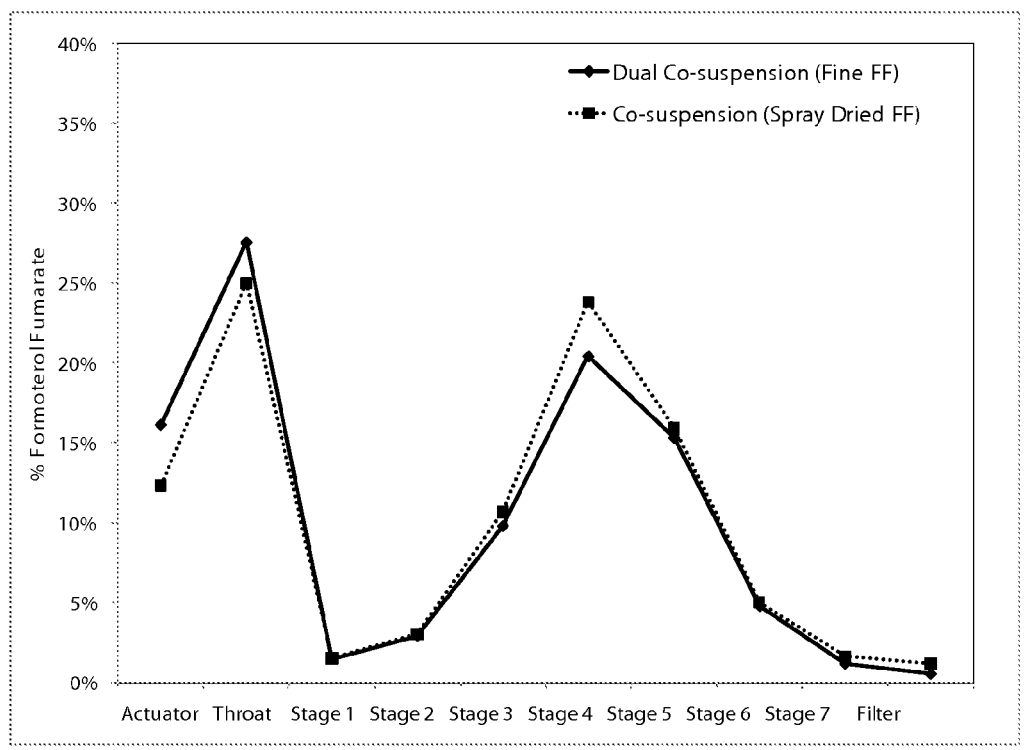
FIG. 12 is a graph that depicts the formoterol fumarate particle size distribution achieved by a second dual co-suspension prepared according to the present description, which included microcrystalline formoterol fumarate and microcrystalline glycopyrrolate active agent particles compared to one that contained microcrystalline glycopyrrolate active agent particles and spray dried formoterol fumarate particles.

The aerosol performance of the dual co-suspension compositions prepared according to this Example was evaluated and compared to the co-suspension composition prepared according to Example 1, with aerosol performance being assessed as described in Example 1. The results of such comparisons are provided in FIG. 10 through FIG. 12. As is easily appreciated by reference to these figures, regardless of whether the crystalline formoterol material used in providing the dual co-suspension was fine or coarse, the FF and GP particle size distributions for the dual co-suspension compositions were substantially the same as those achieved by the co-suspension composition prepared according to Example 1.

Figure 13:
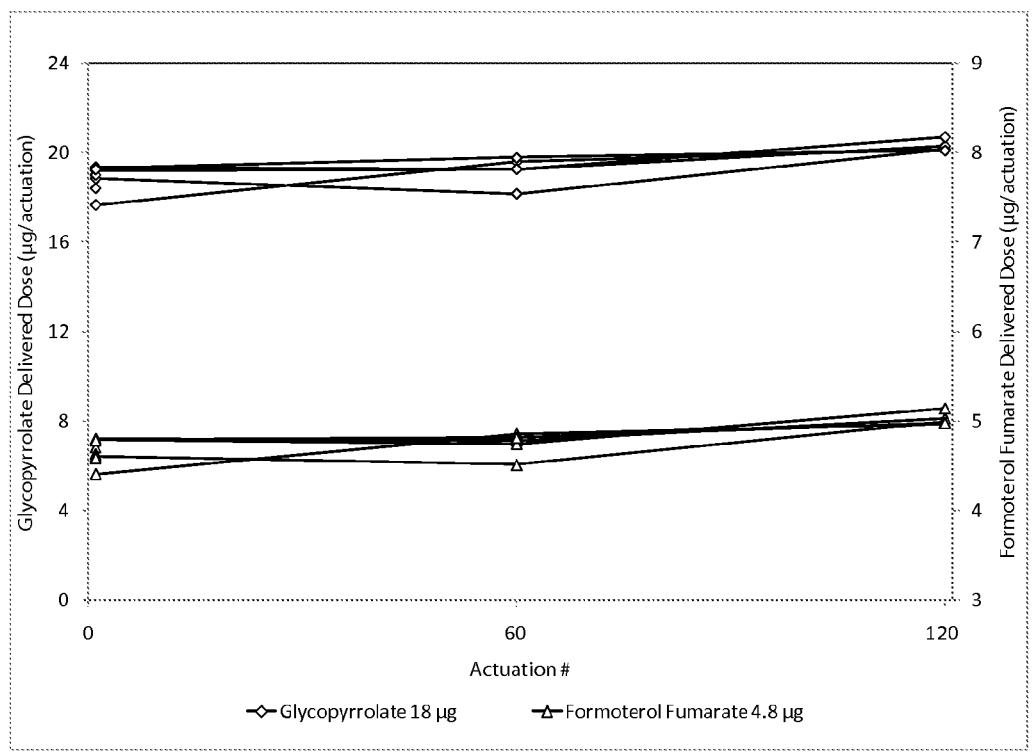
FIG. 13 is a graph, which depicts the delivered dose uniformity of glycopyrrolate and formoterol fumarate in an exemplary dual co-suspension formulation prepared according to the present description.

In addition, the delivered dose uniformity for GP and FF provided by the dual co-suspension compositions as described in this Example was assessed in as described in Example 1. The results of this assessment are illustrated in FIG. 13. The dual co-suspension formulations provided desirable DDU characteristics for both GP and FF as all actuations delivered the expected dose within ±25% of the mean.

EXAMPLE 5

The formulation of a dual co-suspension composition of salmeterol xinafoate (SX) active agent particles and fluticasone propionate (FP) active agent particles is described. Both FP and SX are present in the propellant as a micronized, crystalline particles. The two species of micronized active agent particles are co-suspended with spray dried suspending particles.

Micronized SX (4-hydroxy-α1-[[[6-(4-phenylbutoxy)hexyl]amino]methyl]-1,3-benzenedimethanol, 1-hydroxy-2-naphthalenecarboxylate) was received by the manufacturer (Inke SA, Germany) and used as active agent particles. The particle size distribution of the SX was determined by laser diffraction. 50% by volume of the micronized particles exhibited an optical diameter smaller than 2 μm, and 90% by volume exhibited an optical diameter smaller than 3.9 μm.

Micronized FP (S-(fluoromethyl)$6^\alpha$,9-difluoro-$11^\beta$-17-dihydroxy-$16^\alpha$-methyl-3-oxoandrosta-1,4-diene-$17^\beta$-carbothioate, 17-propionate) was received as micronized by the manufacturer (Hovione FarmaCiencia SA, Loures Portugal) and used as active agent particles. The particle size distribution of the FP was determined by laser diffraction. 50% by volume of the micronized particles exhibited an optical diameter smaller than 2.6 μm, and 90% by volume exhibited an optical diameter smaller than 6.6 μm.

Suspending particles were manufactured as follows: 150 mL of a fluorocarbon-in-water emulsion of PFOB (perfluorooctyl bromide) stabilized by a phospholipid was prepared; 12.3 g of the phospholipid, DSPC (1,2-disteroyl-sn-glycero-3-phosphocholine) and 1.2 g of calcium chloride were homogenized in 100 mL of hot water (70° C.) using a high shear mixer; and 65 ml, of PFOB were added slowly during homogenization. The resulting coarse emulsion was then further homogenized using a high pressure homogenizer (Model C3, Avestin, Ottawa, Calif.) at pressures of up to 140 MPa for 3 passes.

The emulsion was spray dried in nitrogen using the following spray drying conditions: Inlet temperature 90° C.; outlet temperature 69° C.; emulsion feed rate 2.4 ml/min; and total gas flow 498 l/min. The particle size distribution of the suspending particles, VMD, was determined by laser diffraction. 50% by volume of the suspending particles were smaller than 2.7 μm, the Geometric Standard Deviation of the distribution was 2.0. Additionally, the aerodynamic particle size distribution of the suspending particles was determined with a time-of-flight particle sizer. 50% by volume of the suspending particles had an aerodynamic particle diameter smaller than 1.6 μm. The large difference between aerodynamic particle diameter and optical particle diameter indicates that the suspending particles had a low particle density <0.5 kg/l. This was verified by electron microscopy, which confirmed that the suspending particles exhibited a hollow, thin-walled morphology.

MDIs were prepared by weighing the target masses of micronized FP, SX, and suspending particles into fluorinated ethylene polymer (FEP) coated aluminum canisters (Presspart, Blackburn, UK) with a 19 mL volume. The canisters were crimp sealed with 63 μl valves (# BK 357, Bespak, King's Lynn, UK) and filled with 10 ml of HFA 134a (1,1,1,2-tetrafluoroethane) (Ineos Fluor, Lyndhurst, UK) by overpressure through the valve stem. After injecting the propellant, the canisters were sonicated for 15 seconds and agitated on a wrist action shaker for 30 minutes. The canisters were fitted with polypropylene actuators with a 0.3 mm orifice (# BK 636, Bespak, King's Lynn, UK). Aerosol performance was assessed shortly after manufacturing in accordance with USP 601, as described in Example 1. Results are reported below in Table 4.

using a high pressure homogenizer at 140 MPa for 3 passes. The homogenization reduced the particle size of the suspended FP crystals. The emulsion was spray dried in nitrogen using the following spray drying conditions: inlet temperature 95° C.; outlet temperature 72° C.; emulsion feed rate 2.4 ml/min; and total gas flow 525 l/min.

MDIs were prepared by weighing the target masses of micronized SX active agent particles and FP-containing suspending particles into fluorinated ethylene polymer (FEP) coated aluminum canisters (Presspart, Blackburn, UK) with a

TABLE 4

Results for a co-suspension of Fluticasone Propionate (FP) and Salmeterol Xinafoate (SX) of Example 5

| Suspending particle conc. | Target Delivered Dose FP | Target Delivered Dose SX | FP DDU | SX DDU | FP FPF | SX FPF | FP MMAD | SX MMAD |
|---|---|---|---|---|---|---|---|---|
| 5.9 mg/mL | 12 μg | 25 μg | 6.1% RSD* | 6.1% RSD* | 27% | 49% | 4.1 μm | 3.4 μm |

*no trend observed

The delivered dose uniformity through use was tested and all individual delivered doses were within ±20% of mean, at 6.1% relative standard deviation (also referred to as "RSD"). Visual observation of the co-suspension was conducted in glass vials and no sedimentation of active agent particles was observed. The vials were left to settle for 24 hours without agitation. The suspension flocculated slowly and formed a homogeneous, single cream layer.

EXAMPLE 6

The formulation of a combination co-suspension composition of salmeterol xinafoate (SX) active agent particles and fluticasone propionate (FP) suspending particles is described. SX is present in the propellant as a micronized, crystalline particle. It is co-suspended with spray dried suspending particles that have micronized FP disposed into the material forming the suspending particles. To achieve this, FP crystals are suspended in the feedstock used to manufacture the lipid-based suspending particles. The FP and SX used to form the active agent particles and suspending particles referenced in this example were as described in Example 5.

FP-containing suspending particles were manufactured as follows: 200 mL of a fluorocarbon-in-water emulsion of PFOB stabilized by a phospholipid was prepared; 3.3 g of the phospholipid (DSPC) and 0.8 g of micronized FP were dispersed and 0.3 g of calcium chloride dihydrate was dissolved in 100 mL of warm water (70° C.) using a high shear mixer; and 44 mL of PFOB was added slowly during dispersion. The resulting coarse emulsion was then further homogenized 19 mL volume. The canisters were crimp sealed with 63 μl valves (# BK 357, Bespak, King's Lynn, UK) and filled with 10 ml of HFA 134a (1,1,1,2-tetrafluoroethane) (Ineos Fluor, Lyndhurst, UK) by overpressure through the valve stem. After injecting the propellant, the canisters were sonicated for 15 seconds and agitated on a wrist action shaker for 30 minutes. The canisters were fitted with polypropylene actuators with a 0.3 mm orifice (# BK 636, Bespak, King's Lynn, UK). Aerosol performance was assessed shortly after manufacturing in accordance with USP 601 as previously described in Example 1. Results are reported below in Table 5.

TABLE 5

Results for a Co-suspension of Salmeterol Xinafoate (SX) Active Agent Particles with Fluticasone Propionate-containing Suspending Particles.

| FP-Suspending conc. | Target Delivered Dose FP | Target Delivered Dose SX | FP DDU | SX DDU | FP FPF | SX FPF | FP MMAD | SX MMAD |
|---|---|---|---|---|---|---|---|---|
| 4.2 mg/mL | 60 μg | 13 μg | 9.0% RSD* | 13% RSD* | 55% | 51% | 2.8 μm | 3.0 μm |

*with a slight upward trend

The delivered dose uniformity through use was tested and all individual delivered doses were within ±25% of mean, at 9.0% RSD for FP and 13% RSD for SX. Visual observation of the co-suspension was conducted in glass vials and no sedimentation of active agent particles was observed. The vials were left to settle for 24 hours without agitation. The suspension flocculated slowly and formed a homogeneous, single cream layer, showing no indication of separation of SX and suspending particles.

EXAMPLE 7

The formulation of a dual co-suspension composition including budesonide active agent particles and mometasone furoate active agent particles is described. Budesonide (BD) and mometasone furoate (MF) were present in the propellant as a micronized, crystalline particles and are co-suspended with spray dried suspending particles.

BD, 16,17-(butylidenebis(oxy))-11,21-dihydroxy-, (11-β, 16-α)-pregna-1,4-diene-3,20-dione, was received micronized by the manufacturer (AARTI, Mumbai, India) and used as active agent particles. The particle size distribution of the BD was determined by laser diffraction. 50% by volume of the micronized particles exhibited an optical diameter smaller than 1.9 µm, and 90% by volume exhibited an optical diameter smaller than 4.3 µm.

MF, 9α,21-dichloro-11β,17-dihydroxy-16α-methylpregna-1,4-diene-3,20-dione 17-(2-furoate), was received micronized by the manufacturer (AARTI, Mumbai, India) and used as active agent particles. The particle size distribution of the MF was determined by laser diffraction. 50% by volume of the micronized particles exhibited an optical diameter smaller than 1.6 µm, and 90% by volume exhibited an optical diameter smaller than 3.5 µm.

Suspending particles were manufactured as follows: 500 mL of a fluorocarbon-in-water emulsion of PFOB (perfluorooctyl bromide) stabilized by a phospholipid was prepared; 18.7 g of the phospholipid, DSPC (1,2-disteroyl-sn-glycero-3-phosphocholine) and 1.3 g of calcium chloride were homogenized in 400 mL of hot water (75° C.) using a high shear mixer; and 100 mL of PFOB were added slowly during homogenization. The resulting coarse emulsion was then further homogenized using a high pressure homogenizer (Model C3, Avestin, Ottawa, Calif.) at pressures of up to 170 MPa for 5 passes. The emulsion was spray dried in nitrogen using the following spray drying conditions: inlet temperature 95° C.; outlet temperature 72° C.; emulsion feed rate 2.4 ml/min; and total gas flow 498 l/min.

MDIs were prepared by weighing the target masses of micronized active and suspending particles into coated glass vials with a 15 mL volume. The canisters were crimp sealed with 63 µl valves (Valois, Les Vaudreuil, France) and filled with 9.2 g of HFA 134a (1,1,1,2-tetrafluoroethane) (Ineos Fluor, Lyndhurst, UK) by overpressure through the valve stem. After injecting the propellant, the canisters were sonicated for 15 seconds and agitated on a wrist action shaker for 30 minutes. The suspension concentrations were 0.8 mg/ml for BD active agent particles, 1.1 mg/ml for MF active agent particles, and 6 mg/ml for the suspending particles. The suspending particle to active agent particle ratio was 7.5 for BD and 5.5 for MF. Target ex actuator doses were 40 µg for BD and 55 µg for MF.

Visual observation of the co-suspended configurations showed no sedimentation of active agent particles. The vials were left to settle for 16 hours without agitation. No active agent particles were visible at the bottom of the co-suspension vials. The results showed that crystalline budesonide and mometasone furoate material forming the different species of active agent particles associated with the suspending particles, formed a co-suspension in the configurations disclosed herein. The association between active agent particles and suspending particles was strong enough to overcome buoyancy forces as settling of the active agent particles was successfully inhibited.

EXAMPLE 8

Dual co-suspension compositions were prepared with suspending particles including either mometasone furoate (MF) or budesonide (BD), and MDIs incorporating the composition were prepared. The co-suspension composition included a combination of crystalline glycopyrrolate (GP) and formoterol fumarate (FF) active agent particles co-suspended with suspending particles including either MF or BD. Each of the APIs were provided as a micronized, crystalline material.

Suspending particles containing 50% (w/w) of either BD or MF were manufactured as follows: high shear homogenization of a dispersion containing 2.8 g of DSPC (1,2-Distearoyl-sn-Glycero-3-Phosphocholine), and 0.26 g of calcium chloride in 400 mL of hot water (75° C.) using a high shear mixer was performed while 56.6 g of PFOB were added slowly. Micronized MF or BD (in 1:1 weight proportion to DSPC) was added to the resulting coarse emulsion, which was further homogenized using a high pressure homogenizer (Model C3, Avestin, Ottawa, Calif.) at pressures of up to 170 MPa for 3 to 5 passes. The emulsion was spray dried using the following spray drying conditions: inlet temperature 90-95° C.; outlet temperature 95-72° C.; emulsion feed rate 2-8 mL/min; total dry nitrogen flow 525-850 L/min. The particle size distribution of the resulting powders was determined by laser diffraction, 50% by volume of the suspending particles were smaller than 1.8 µm, the span of the distribution was 1.6 µm.

Canisters containing either 50% (w/w) MF or BD containing suspending particles were filled with HFA 134a propellant, targeting a 50 or 100 µg/actuation of MF or BD, respectively. Their aerosol particle size distributions were determined according to the methods described in Example 1, and results are shown in Table 6. A comparable series of canisters containing MF or BD containing suspending particles in combination with GP and FF active agent particles were produced. Sufficient micronized GP and FF API material was added to such canisters in amounts sufficient to provide targeted delivered doses of 36 µg/actuation and 6 µg/actuation for GP and FF, respectively. Additional placebo suspending particles prepared as described herein but free of any active agent (also referred to as "placebo" suspending particles) were added to certain to reach a total co-suspension concentration of 5.5 mg/ml.

The aerosol particle size distributions provided by the co-suspension compositions prepared according to this Example were determined as described in Example 1, with the results are shown in Table 7. The mass mean aerodynamic diameter of the corticosteroid in the single component suspensions is equivalent to the one obtained in the triple combination formulations prepared with two different species of active agent particles co-suspended with BD or MF containing suspending particles. As was true of the co-suspension compositions containing a combination of two different active agents, the triple co-suspension compositions prepared according to the present description avoided a combination effect.

TABLE 6

Suspension MDIs in HFA 134a propellant containing corticosteroid suspending particles. Aerosol properties, mass aerodynamic diameter and fine particle fraction determined by drug specific cascade impaction.

| | Suspension. Concentration (mg/ml) | MMAD (µm) | FPF (%) |
|---|---|---|---|
| Mometasone Furoate | 5.5 | 2.88 | 61.0 |
| Budesonide | 5.6 | 3.20 | 61.7 |

TABLE 7

Triple combination suspension MDIs in HFA 134a propellant
including corticosteroid containing suspending particles
(Mometasone Furoate or Budesonide), a LAMA (Glycopyrrolate)
and a LABA (Formoterol Fumarate). Aerosol properties,
mass mean aerodynamic diameter and fine particle fraction
determined by drug specific cascade impaction.

| | Suspension Concentration (mg/ml) | Drug | MMAD (μm) | FPF (%) |
|---|---|---|---|---|
| Triple A | 2.3 | Formoterol | 3.96 | 44.4 |
| | | Glycopyrrolate | 3.71 | 49.0 |
| | | Mometasone | 2.90 | 61.6 |
| Triple B* | 5.6 | Formoterol | 3.52 | 44.4 |
| | | Glycopyrrolate | 3.34 | 49.0 |
| | | Mometasone | 2.54 | 61.6 |
| Triple C | 5.5 | Formoterol | 3.89 | 47.1 |
| | | Glycopyrrolate | 3.74 | 50.0 |
| | | Budesonide | 3.12 | 63.1 |

*with added placebo suspending particles

EXAMPLE 9

A triple co-suspension composition according to the present description was produced and MDIs incorporating the composition were prepared. The composition included a combination of glycopyrrolate (GP), formoterol fumarate (FF), and mometasone furoate (MF) active agent particles, with each being provided as a micronized, crystalline API material.

A triple co-suspension MDI was manufactured by semi-automated suspension filling. The triple co-suspension consisted of a combination of three microcrystalline active pharmaceutical ingredients forming three different species of active agent particles: MF (corticosteroid); GP (LAMA); and FF (LABA). These three different species of active agent particles were co-suspended with suspending particles in HFA 134a propellant. The triple co-suspension was formulated to the following delivered dose targets: 50 μg per actuation MF; 36 μg per actuation GP; and 4.8 μg per actuation FF. In addition to the triple co-suspension, a monotherapy co-suspension including only MF was produced. The monotherapy MF co-suspension included MF active agent particles co-suspended in the propellant with suspending particles as described in this Example, and was formulated to provide a target delivered dose of 50 μg per actuation MF.

Suspending particles were manufactured via spray dried emulsion at a feed stock concentration of 80 mg/mL with a composition of 93.44% DSPC (1,2-Distearoyl-sn-Glycero-3-Phosphocholine) and 6.56% anhydrous calcium chloride (equivalent to a 2:1 DSPC:CaCl$_2$ mole/mole ratio). During the emulsion prep, DSPC and CaCl$_2$ were dispersed with a high shear mixer at 8000-10000 rpm in a vessel containing heated water (80±3° C.) with PFOB slowly added during the process. The emulsion was then processed with 5 passes in a high pressure homogenizer (10000-25000 psi). The emulsion was then spray dried via a spray dryer fitted with a 0.42" atomizer nozzle with a set atomizer gas flow of 18 SCFM. The drying gas flow rate was set to 72 SCFM with an inlet temperature of 135° C., outlet temperature 70° C., and an emulsion flow rate of 58 mL/min.

For MDI manufacturing, a drug addition vessel (DAV) was prepared for suspension filling in the following manner: first adding half of suspending particle quantity, next filling microcrystalline materials, and lastly adding the remaining half of suspending particles to the top. Materials were added to the vessel in a humidity controlled environment of <10% RH. The DAV was then connected to a 4 L suspension vessel and flushed with HFA 134a propellant and then mixed with a magnetic stir bar. The temperature inside the vessel was maintained at 21-23° C. throughout the entire batch production. After recirculation of the batch for 30 min canisters were filled with the suspension mixture through 50 μL EPDM valves. Sample canisters were the selected at random for Total Canister Analysis to ensure correct formulation quantities. The freshly manufactured triple co-suspension MDI batch was then placed on one week quarantine before initial product performance analysis. The mometasone furoate only MDI was manufactured by suspension filling in the same manner.

The primary particle size distribution of all microcrystalline APIs was determined by laser diffraction as described in Example 1, results are shown in Table 9. Aerodynamic particle size distribution and mass mean aerodynamic diameter of all components upon actuation of the suspension MDIs was determined by drug specific cascade impaction as described in Example 1 and are shown in Table 9.

TABLE 9

Triple microcrystalline Co-Suspension in HFA 134a
propellant MDI. Primary particle size distribution
determined by laser diffraction (Sympatec).

| Materials | ×10 (μm) | ×50 (μm) | ×90 (μm) | Span |
|---|---|---|---|---|
| Micronized Mometasone Furoate (MF) | 0.4 | 1.1 | 2.8 | 2.2 |
| Micronized Glycopyrrolate (GP) | 0.5 | 1.3 | 3.0 | 1.8 |
| Micronized Formoterol Fumarate Dihydrate (FF) | 0.6 | 1.9 | 4.1 | 1.8 |

TABLE 10

Triple co-suspension MDIs in HFA 134a propellant containing
microcrystalline Corticosteroid (Mometasone Furoate),
LABA (Formoterol Fumarate) and a LAMA (Glycopyrrolate).
Aerosol properties, mass mean aerodynamic diameter
and fine particle fraction were determined by drug
specific cascade impaction (NGI).

| | Suspension Concentration (mg/ml) | Drug | MMAD (μm) | FPF (%) |
|---|---|---|---|---|
| Triple (Corticosteroid, LABA, LAMA) | 6 | Mometasone | 3.18 | 62.6 |
| | | Formoterol | 3.50 | 59.5 |
| | | Glycopyrrolate | 2.97 | 64.1 |
| Mono (Corticosteroid) | 6 | Mometasone | 3.36 | 58.9 |

Figure 14:
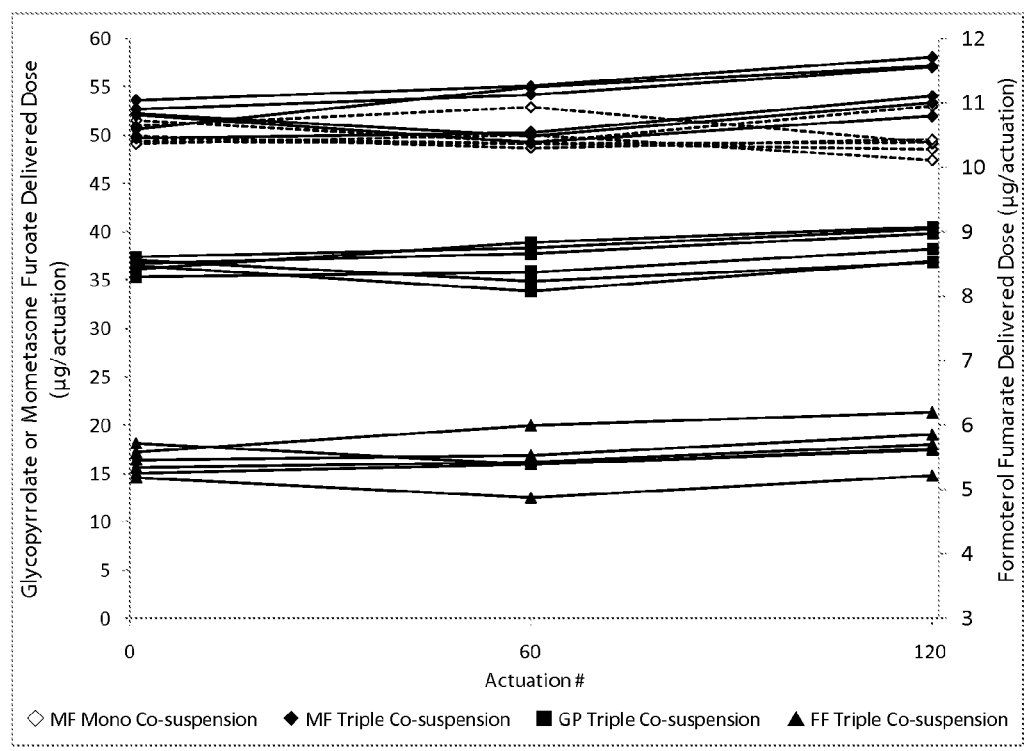
FIG. 14 depicts the delivered dose uniformity for each active agent included in an exemplary triple co-suspension composition, which included microcrystalline glycopyrrolate, formoterol fumarate and mometasone furoate active agent particles.
Figure 15:
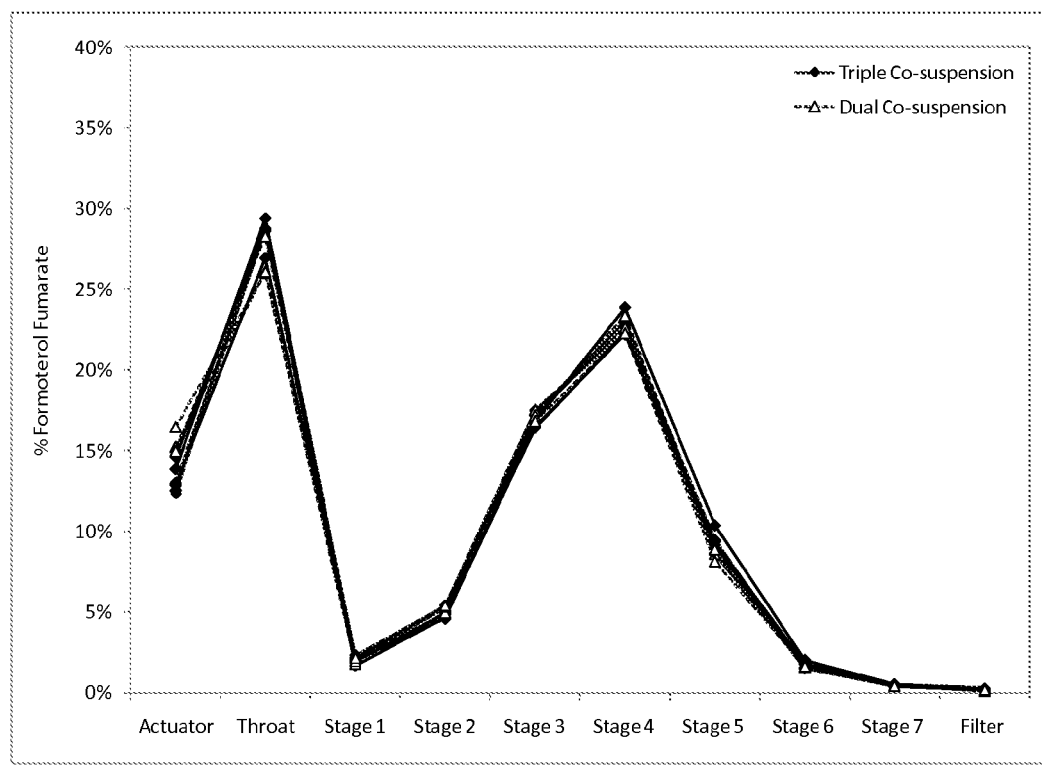
FIG. 15 is a graph depicting the formoterol fumarate aerodynamic particle size distributions achieved in a triple co-suspension prepared according to the present description, which included microcystalline glycopyrrolate, formoterol fumarate and mometasone furoate active agent particles, compared to that achieved in a dual co-suspension which included glycopyrrolate and formoterol fumarate.
Figure 16:
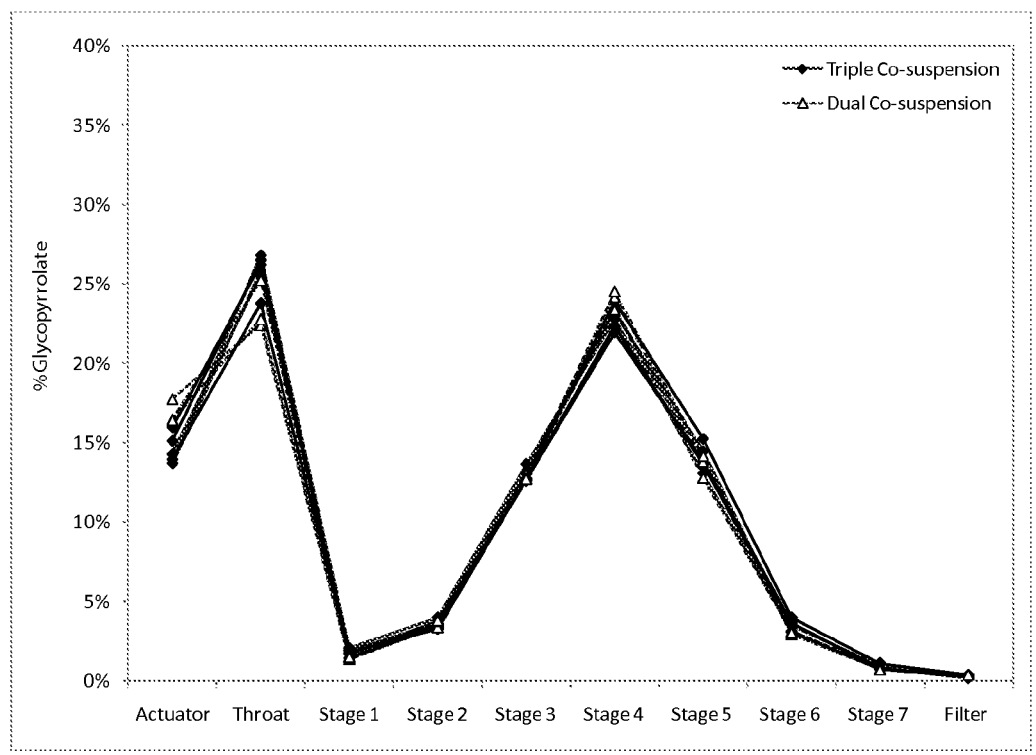
FIG. 16 is a graph depicting the glycopyrrolate aerodynamic particle size distributions achieved in a triple co-suspension prepared according to the present description, which included microcrystalline glycopyrrolate, formoterol fumarate and mometasone furoate active agent particles, compared to that achieved in a dual co-suspension which included glycopyrrolate and formoterol fumarate.

Aerosol performance and delivered dose uniformity achieved by the triple co-suspensions prepared according to this Example were evaluated according to the description provided in Example 1. FIG. 14 illustrates the GP, FF and MF DDU achieved from two canisters containing MF only and two canisters containing MF, GP and FF prepared according to this Example. The DDU of MF delivered from the MF monotherapy configuration is equivalent to the one achieved with the triple co-suspension composition. The aerosol performance of the triple co-suspension composition prepared according to this example was also assessed relative to formulations containing a combination of only two active agents, FF and GP. The aerodynamic particle size distribution of FF and GP are equivalent whether delivered from the compositions containing two active agents or three active agents as shown in FIGS. 15 and 16, respectively.

As was true of the co-suspension compositions containing a combination of two different active agents, the triple co-suspension compositions prepared according to the present description avoided a combination effect.

EXAMPLE 10

Exemplary triple co-suspension compositions according to the present description were produced and metered dose inhalers incorporated in the composition were prepared. The triple co-suspensions included glycopyrrolate (GP) or tiotropium bromide (TB) in combination with formoterol fumarate (FF), and mometasone furoate (MF) active agents, with each API being used as micronized, crystalline material.

Two separate suspension MDI batches containing three active pharmaceutical ingredients (APIs), a corticosteroid, a LAMA and a LABA were prepared. The APIs were provided as microcrystalline materials that served as the active agent particles co-suspended with suspending particles prepared as described herein. The triple co-suspension compositions prepared as described in this Example were prepared by adding the active agent particles and suspending particles to an HFA 134a propellant.

The first triple co-suspension batch (Triple GFM) was formulated to the following delivered dose targets: 40 μg per actuation MF; 13 μg per actuation GP; and 4.8 μg per actuation FF. The active agent particles were co-suspended with suspending particles manufactured using an emulsion composed of 93.46% DSPC (1,2-Distearoyl-sn-Glycero-3-Phosphocholine) and 6.54% anhydrous calcium chloride spray dried with an 80 mg/mL feed concentration. The DSPC:$CaCl_2$ molar ratio of the suspending particles was 2:1. The suspending particles were combined with the active agent particles in propellant for a formulation target of 6 mg/ml suspending particle concentration. The primary particle sizes of the microcrystalline active agent particles, determined by Sympatec laser diffraction measurements as described in Example 1, are displayed below in Table 11.

The second triple co-suspension batch (TFM) was prepared using a different LAMA API, anhydrous tiotropium bromide (TB) to replace GP. The second triple co-suspension was formulated to the following delivered dose targets: 50 μg per actuation MF; 9 μg per actuation TB; and 4.8 μg per actuation FF. The suspending particles were prepared as described in relation to the Triple GFM co-suspension, and the active agent particles were co-suspended with the suspending particles at a targeted suspension concentration of 6 mg/ml. The primary particle sizes of the microcrystalline active agent particles, determined by Sympatec laser diffraction measurements as described in Example 1, are displayed below in Table 12.

MDIs were prepared using the Triple GFM and Triple TFM co-suspension compositions, and the aerosol properties, fine particle fraction, and mass median aerodynamic diameter were determined as described in Example 1. Table 13 sets out the MMAD and FPF performance for Triple GFM and Triple TFM, while the desirable aerosol properties achieved by the Triple GFM and Triple TFM co-suspensions are shown in FIG. 17 (showing the aerodynamic particle size distribution of GP and TB obtained from Triple GFM and Triple TFM, respectively).

TABLE 11

Triple GFM primary particle size distribution determined by laser diffraction (Sympatec).

| Materials | $d_{10}$ (μm) | $d_{50}$ (μm) | $d_{90}$ (μm) | Span |
|---|---|---|---|---|
| Micronized Mometasone Furoate | 0.4 | 1.0 | 2.3 | 1.9 |
| Micronized Glycopyrrolate | 0.5 | 1.4 | 3.4 | 2.1 |
| Micronized Formoterol Fumarate Dihydrate | 0.5 | 1.4 | 2.7 | 1.9 |

TABLE 12

Triple TFM primary particle size distribution determined by laser diffraction (Sympatec).

| Materials | $d_{10}$ (μm) | $d_{50}$ (μm) | $d_{90}$ (μm) | Span |
|---|---|---|---|---|
| Micronized Mometasone Furoate | 0.4 | 1.1 | 2.8 | 2.2 |
| Micronized Tiotropium Bromide Anhydrous | 0.5 | 1.3 | 3.9 | 2.7 |
| Micronized Formoterol Fumarate Dihydrate | 0.6 | 1.9 | 4.1 | 1.9 |

TABLE 13

Triple GFM and Triple TFM aerosol properties, mass mean aerodynamic diameter and fine particle fraction determined by drug specific cascade impaction

| | Suspension Concentration (mg/ml) | Drug | MMAD (μm) | FPF (%) |
|---|---|---|---|---|
| Triple GFM | 6 | Formoterol | 2.80 | 65.3 |
| | | Glycopyrrolate | 2.90 | 49.5 |
| | | Mometasone | 3.10 | 49.2 |
| Triple TFM | 6 | Formoterol | 3.82 | 42.4 |
| | | Tiotropium | 3.79 | 42.0 |
| | | Mometasone | 4.00 | 43.6 |

EXAMPLE 11

Exemplary dual co-suspension compositions according to the present description were produced and MDIs incorporating the dual co-suspension compositions were prepared. The compositions included a combination of glycopyrrolate (GP) and formoterol fumarate (FF), with each being provided as a micronized, crystalline material with particle size distribution as shown in Table 14. The microcrystalline GP and FF materials provided two species of active agent particles, while suspending particles were prepared as described in Example 4. In preparing the dual co-suspensions described in this Example, the GP active agent particles, FF active agent particles, and suspending particles were combined in an HFA 134a propellant.

The dual co-suspensions described in this example were prepared by first dispensing the appropriate quantities of GP and FF active agent particles and suspending particles into a drug addition vessel (DAV) inside a humidity controlled chamber (RH<5%). The DAV is then sealed under a nitrogen atmosphere and connected to the suspension vessel containing 12 kg of HFA-134a. A slurry was then formed by adding 0.5-1 kg of HFA-134a into the DAV, which is then removed from the suspension vessel and gently swirled. The slurry is then transferred back to the suspension mixing vessel and diluted with additional HFA-134a to form the final suspension at target concentration stirring gently with an impeller. The suspension is then recirculated via a pump to the filling system for a minimum time prior to initiation of filling. Mixing and recirculation continue throughout the filling process. Valves are placed onto MDI canisters and then purged of air either by a vacuum crimping process, or an HFA-134a purging process, followed by valve crimping. The crimped canisters are then filled through-the-valve with the appropriate quantity of suspension, adjusted by the metering cylinder.

TABLE 14

Glycopyrrolate and Formoterol Fumarate particle size distributions.

| Designation | $d_{10}$ (μm) | $d_{50}$ (μm) | $d_{90}$ (μm) | Span |
|---|---|---|---|---|
| FF API | 0.6 | 1.9 | 4.1 | 1.8 |
| GP API | 0.5 | 1.3 | 3.0 | 1.9 |

The suspension for pressure filling is prepared by first dispensing the appropriate quantities of micronized glycopyrrolate and formoterol fumarate crystals and suspending particles to a drug addition vessel (DAV), inside a humidity controlled chamber (RH<5%). In the current example the suspending particle carrier was added in three equal portions intercalating the addition of GP and FF after the first and second addition respectively. The DAV is then sealed under a nitrogen atmosphere and connected to the suspension vessel containing 12 kg of HFA-134a. A slurry was then formed by adding 0.5-1 kg of HFA-134a into the DAV, which is then removed from the suspension vessel and gently swirled. The slurry is then transferred back to the suspension mixing vessel and diluted with additional HFA-134a to form the final suspension at target concentration stirring gently with an impeller. The suspension is then recirculated via a pump to the filling system for a minimum time prior to initiation of filling. Mixing and recirculation continue throughout the filling process. Valves are placed onto canisters and then purged of air either by a vacuum crimping process, or an HFA-134a purging process followed by valve crimping. The crimped canisters are then filled through-the-valve with the appropriate quantity of suspension, adjusted by the metering cylinder.

MDIs containing the dual co-suspensions described in this Example were prepared to contain two different doses GP and FF. Specifically, a first run of dual co-suspension compositions were prepared to provide 18 μg per actuation GP and 4.8 μg per actuation FF ("low dose"), and a second run of dual co-suspension compositions were prepared to provide 36 μg per actuation GP and 4.8 μg per actuation FF ("high dose"). In addition to the dual co-suspensions compositions, monotherapy FF and GP co-suspension compositions were prepared. The monotherapy co-suspension compositions were prepared as described for the dual co-suspensions, except that they included only one species of active agent particles (either GP or FF). The monotherapy co-suspensions were formulated and monotherapy MDIs prepared to provide the following targeted delivered doses: 18 μg per actuation of GP, and 0.5, 1.0, 3.6 or 4.8 μg per actuation of FF. The compositions and MDIs providing 0.5 μg FF and 1 μg FF per actuation are referred to as "ultra low" dose.

Figure 18:
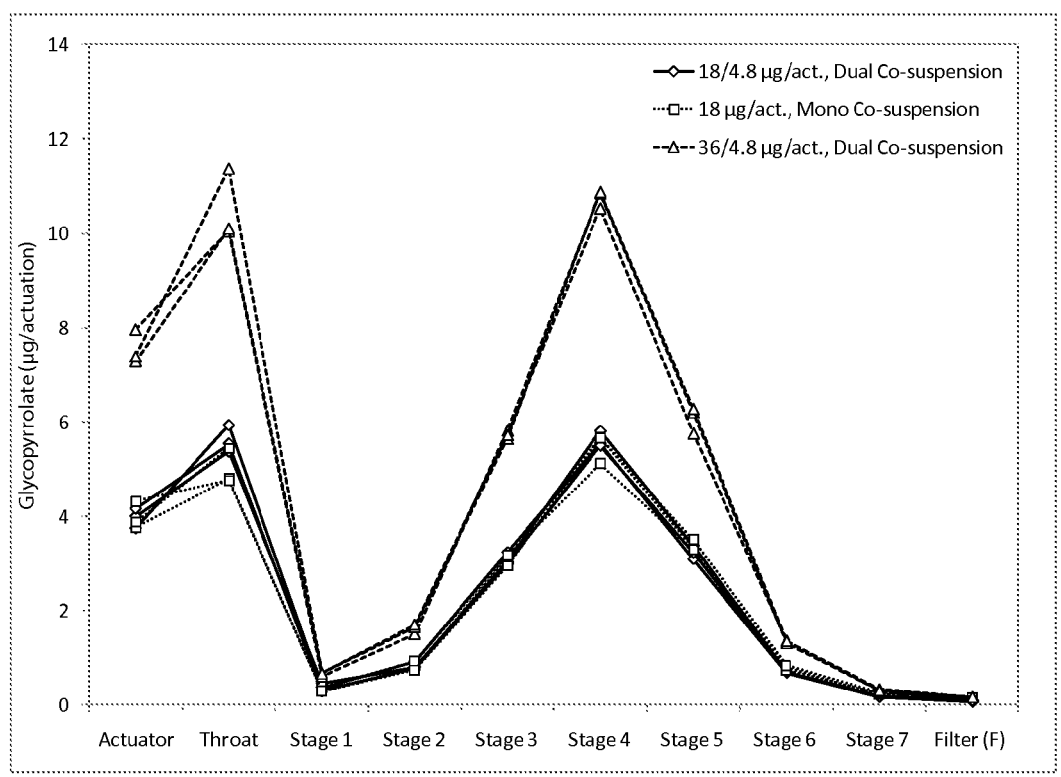
FIG. 18 is a graph depicting the glycopyrrolate aerodynamic size distribution achieved by a two dual and one single component co-suspension prepared according to the present description. The dose proportionality between the two dual co-suspensions as well as the equivalency between the dual and the single component co-suspension is displayed.
Figure 19:
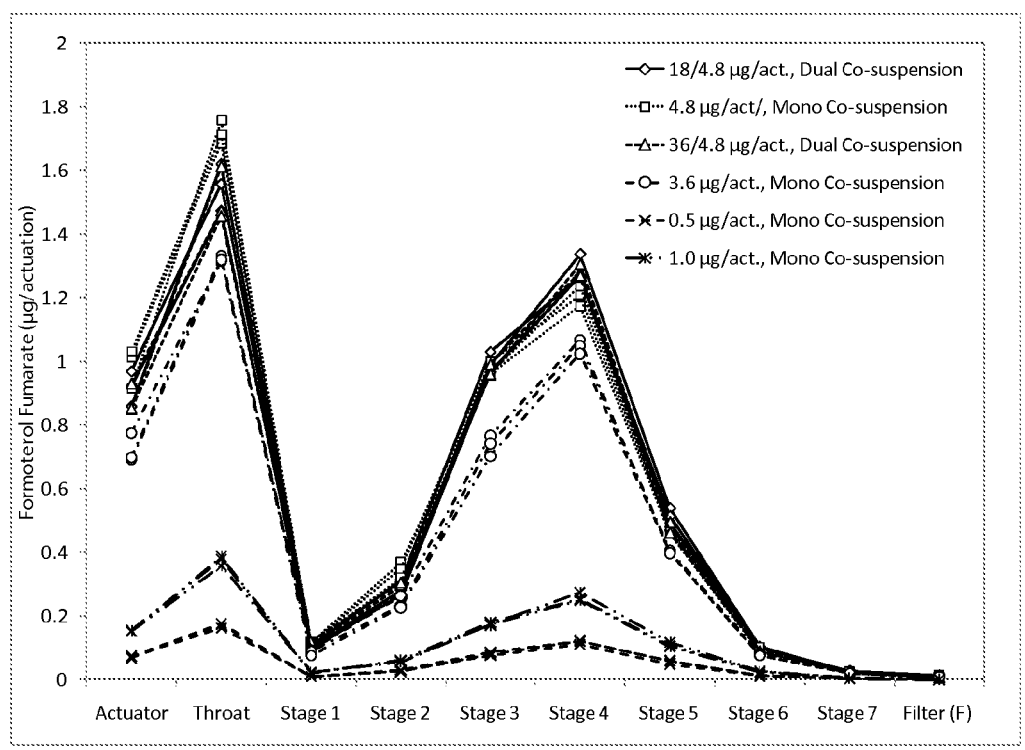
FIG. 19 is a graph depicting the formoterol fumarate aerodynamic size distribution achieved by a two dual and two single component co-suspensions prepared according to the present description. The dose proportionality between the two dual and two single component co-suspensions as well as the equivalency between the dual and the single component co-suspension is displayed.

The drug specific aerodynamic size distributions achieved with MDIs containing the co-suspension compositions prepared according to this Example were determined as described in Example 1. The proportionality of the aerodynamic size distributions of GP obtained from the low and high dose dual co-suspensions as well as the equivalency between the dual and monotherapy co-suspensions is demonstrated in FIG. 18. In the same manner, the proportionality of the aerodynamic size distributions of FF obtained from the dual and monotherapy co-suspensions, including the ultralow, low, and high dose compositions is demonstrated in FIG. 19.

Figure 20:
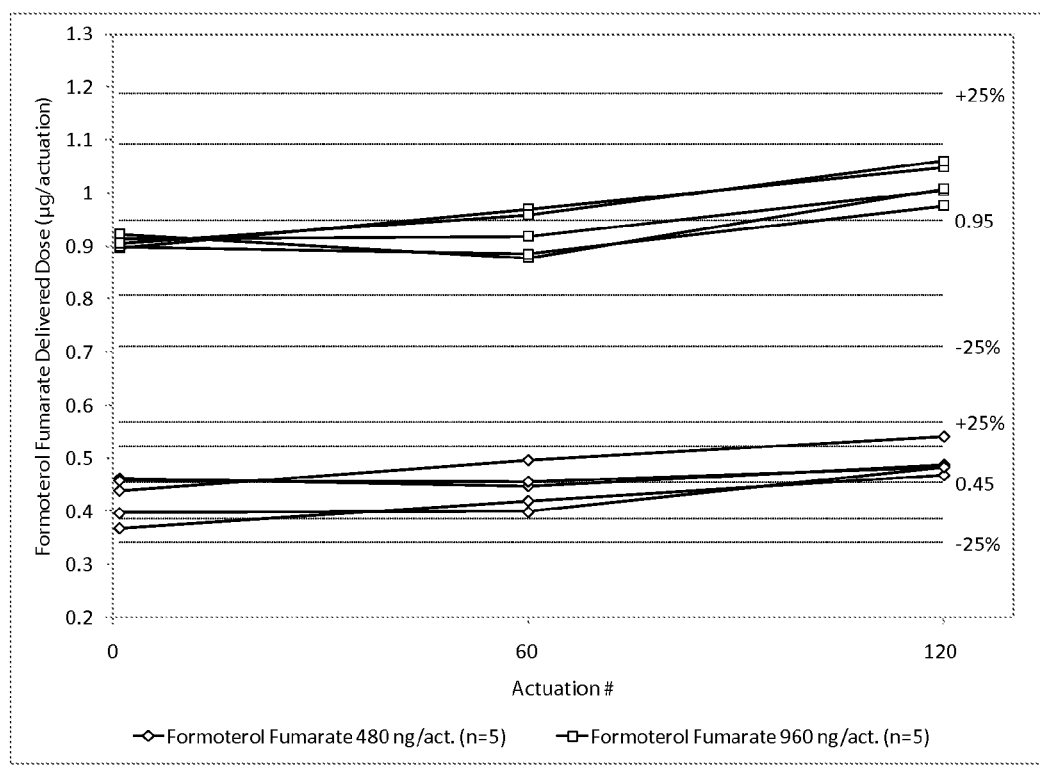
FIG. 20 is a graph depicting the dose delivered uniformity of ultra low formoterol fumarate single component co-suspensions prepared according to the present description.

The delivered dose uniformity of the ultra low dose FF monotherapy MDIs was also measured as described in Example 1. The DDU for the 1 μg/actuation and 0.5 μg/actuation compositions and systems are shown in FIG. 20. Desirable dose delivery uniformity is achieved even for ultralow doses.

EXAMPLE 12

The safety, efficacy and PK performance of combination co-suspension compositions as described herein delivered via a metered dose inhaler (MDI) were evaluated in a clinical trial. The combination co-suspension compositions contained both glycopyrrolate and formoterol fumarate. The clinical trial was a randomized, double-blind, customized, unbalanced, incomplete block, crossover, multi-center study conducted in patients with moderate to very severe Chronic Obstructive Pulmonary Disease (COPD). Two different combination co-suspension compositions as described herein were compared to a placebo and four active comparator compositions delivering only one of the two active agents included in the combination compositions.

The two combination co-suspension compositions administered in the clinical trial included both Glycopyrrolate (GP) and Formoterol Fumarate (FF) active agents delivered as a fixed combination. The combination co-suspensions were prepared generally as described in Example 4, with the GP and FF active agent particles provided as micronized, crystalline GP and FF material, the suspending particles being spray dried particles comprising DSPC and $CaCl_2$, and the suspension medium being formed by HFA 134a. The combination co-suspension compositions were prepared for delivery to patients via an MDI as described herein and were tailored to facilitate administration of two different doses of the GP and FF active agents. The first co-suspension combination composition was formulated to deliver 36 μg GP and 4.8 μg FF to a patient per actuation of the MDI and was used to dose 72 μg GP and 9.6 μg FF to patients twice daily (two actuations of the MDI administered twice daily). This first composition and treatment is also referred to in this example and the accompanying figures as "GP/FF 72/9.6" and the "GP/FF 72/9.6 treatment." The second co-suspension combination composition was formulated to deliver 18 μg GP and 4.8 μg FF to a patient per actuation of the MDI and was used to dose 36 μg GP and 9.6 μg FF to patients twice daily (two actuations of the MDI administered twice daily). This second composition and treatment is also referred to in this example and the accompanying figures as "GP/FF 36/9.6" and the "GP/FF 36/9.6 treatment."

The GP/FF 72/9.6 and GP/FF 36/9.6 treatments were compared against a placebo and five different active compositions containing one of FF, GP or tiotropium as a single active agent. The first composition was an active control, Spiriva Handihaler (tiotropium bromide inhalation powder). Spiriva is a dry powder inhaler (DPI) product and was administered to patients once daily, with each DPI capsule including and 18 μg dose of tiotropium. The next composition, Foradil Aerolizer (formoterol fumarate inhalation powder), was also an active control. Foradil is also a DPI product, but it was administered to patients twice daily, and each DPI capsule included a 12 μg dose of FF. The third composition was a co-suspension composition including only GP as the active agent. The monotherapy GP co-suspension composition (GP 36) was manufactured for pulmonary delivery via an MDI and was administered twice daily, with each administration delivering a 36 μg dose of GP to the patient. The remaining two compositions were two different monotherapy co-suspension compositions including only FF as the active ingredient (FF 9.6 and FF 7.2). The monotherapy FF co-suspension compositions were manufactured for pulmonary delivery via an MDI and were administered twice-daily, with each administration delivering either a 9.6 μg dose of FF (FF 9.6) or a 7.2 μg dose of FF (FF 7.2) to the patient. The GP and FF monotherapy co-suspension compositions were formulated using micronized, crystalline GP or FF material as active agent particles, spray dried particles comprising DSPC and $CaCl_2$ as the suspending particles, and HFA 134a as the suspension medium.

118 patients were randomized into the study and administered study compositions over 7 day periods. On Day 7 of treatment, improvement in $FEV_1$ was assessed in each patient over a period of 12 hours post administration of each of the study compositions, and the area under the curve of the improvement in $FEV_1$ relative to baseline provided by each of the study compositions over the twelve-hour period ($AUC_{0-12}$) was calculated. The $AUC_{0-12}$ on treatment day 7 (Day 7) was used as the primary endpoint for the study. Secondary endpoints included the peak change in $FEV_1$ post administration of each of the study compositions (Peak $FEV_1$) on Day 1 and Day 7, the trough $FEV_1$ experienced by patients after chronic dosing for 7 days but prior to dosing on treatment Day 7 (Morning Trough $FEV_1$) and safety assessments. The two GP/FF co-suspension compositions were safe and well-tolerated.

Figure 21:
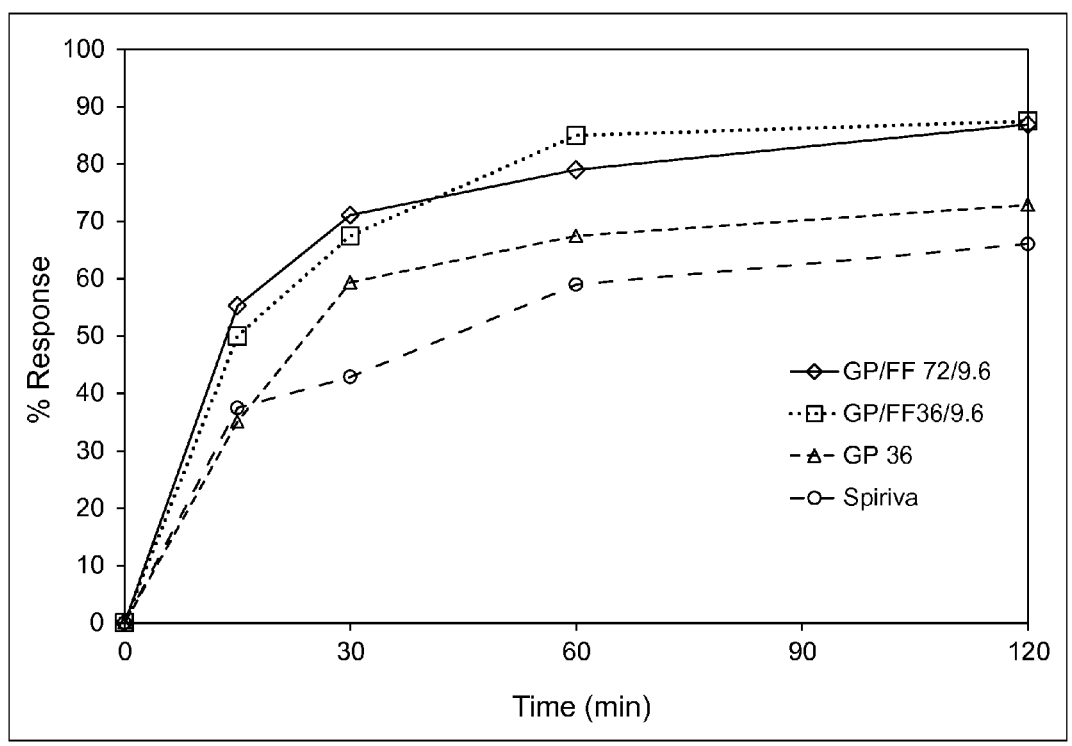
FIG. 21 is a graph depicting the cumulative response over time on the first day of administration of two treatments using combination co-suspension compositions as described herein (GP/FF 72/9.6 and GP/FF 36/9.6) compared to two different delivering a single active agent (one delivering only glycopyrrolate—GP 36, and a second delivering only tiotropium bromide—Spiriva). These compositions were administered to patients as part of the clinical study described in Example 12. Specifically, the graph illustrates the percent of patients achieving ≥12% improvement in $FEV_1$ and the time at which such percentages were achieved.
Figure 22:
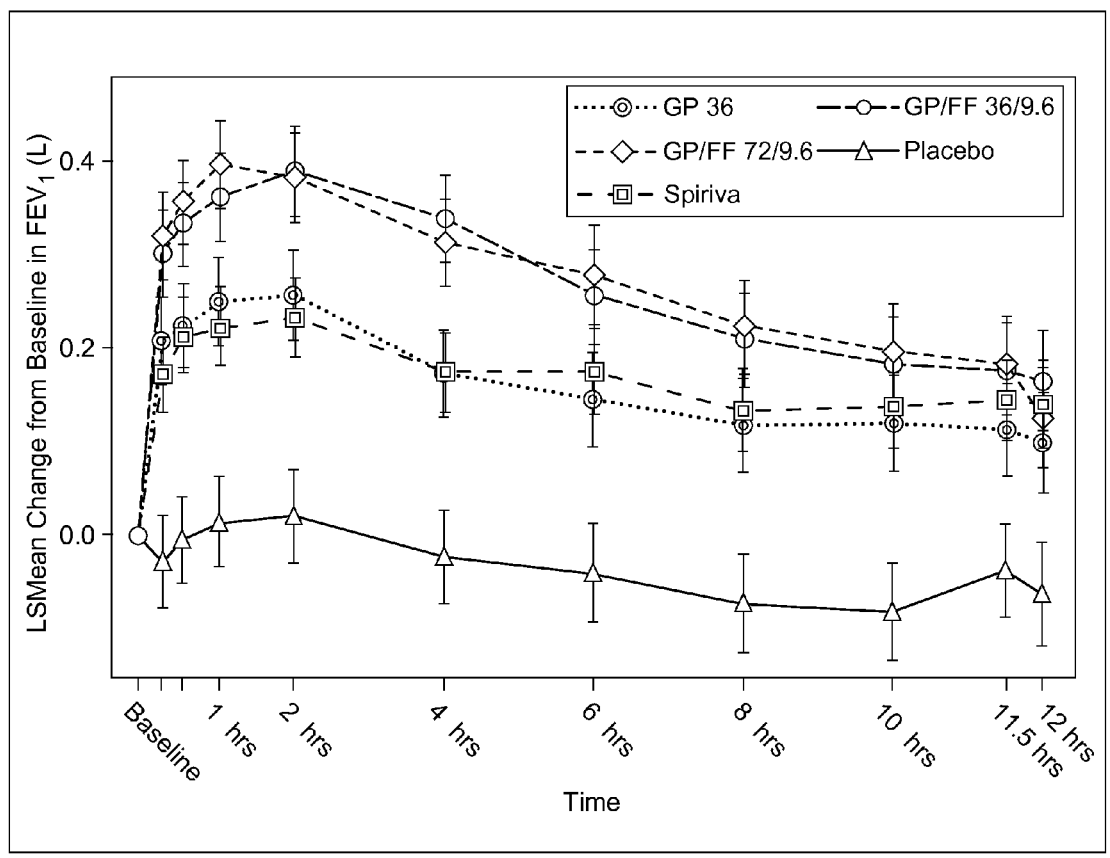
FIG. 22 is a graph illustrating the mean change from baseline in $FEV_1$ $AUC_{0-12}$ on treatment day 7 (Day 7) for various study compositions administered to patients as part of the clinical study described in Example 12. Two treatments using combination co-suspension compositions as described herein (GP/FF 72/9.6 and GP/FF 36/9.6) are compared to a placebo and active compositions delivering a single active agent (one delivering only glycopyrrolate—GP 36, and a second delivering only tiotropium bromide—Spiriva.
Figure 23:
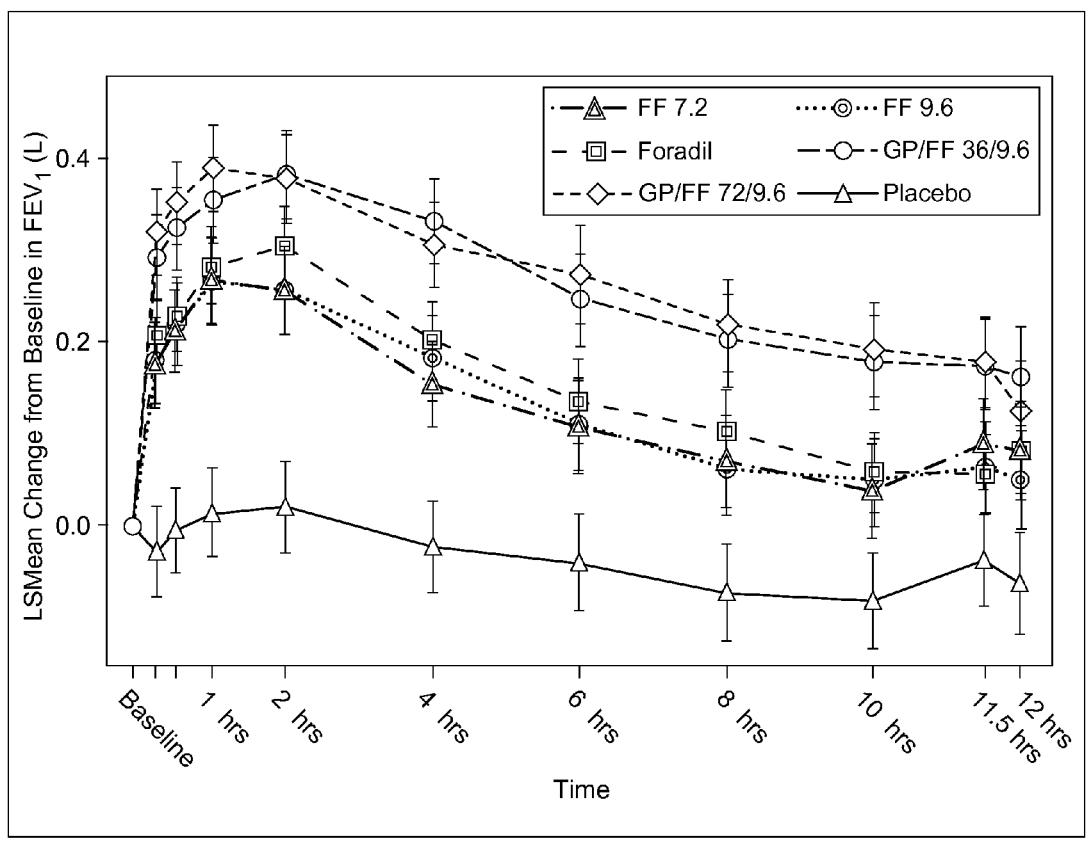
FIG. 23 is a graph illustrating the mean change from baseline in $FEV_1$ $AUC_{0-12}$ on treatment day 7 (Day 7) for various study compositions administered to patients as part of the clinical study described in Example 12. Two treatments using combination co-suspension compositions as described herein (GP/FF 72/9.6 and GP/FF 36/9.6) are compared to a placebo and various different active compositions delivering a single active agent (one delivering only glycopyrrolate—GP 36, and three delivering only formoterol fumarate—FF 7.2, FF 9.6, and Foradil).
Figure 24:
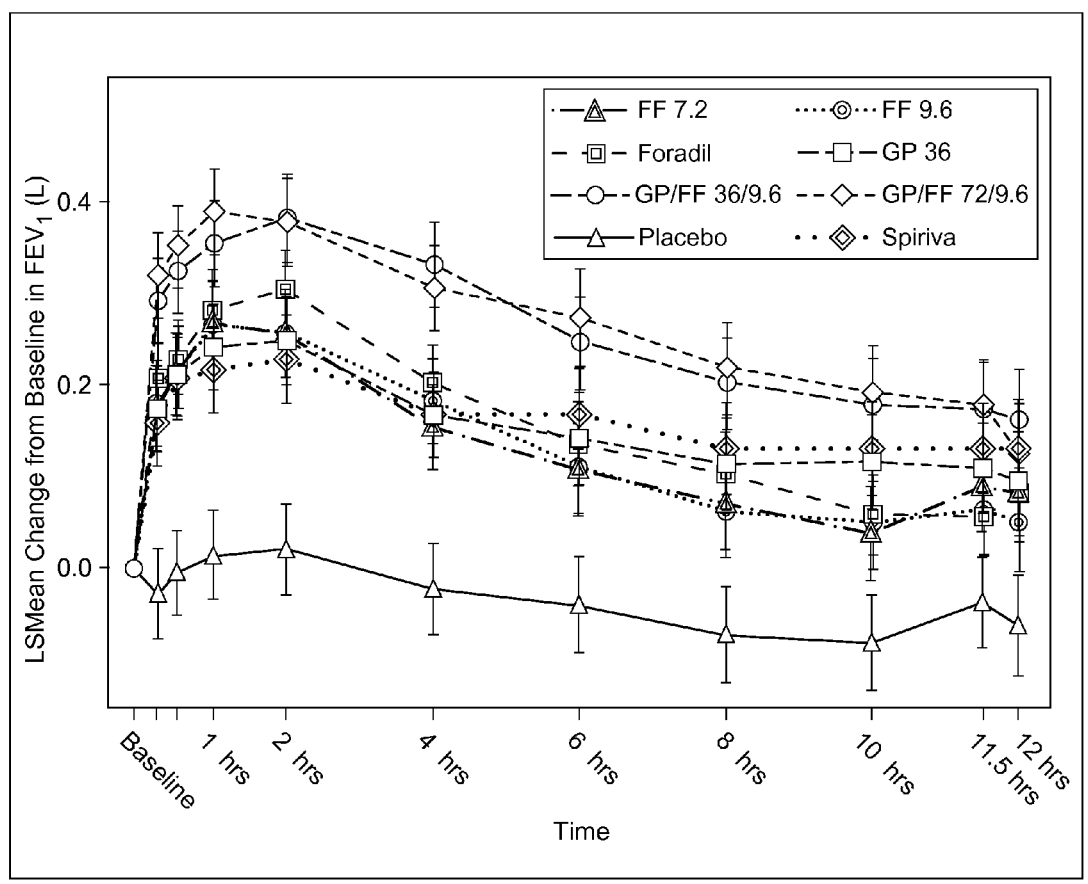
FIG. 24 is a graph illustrating the mean change from baseline in $FEV_1$ $AUC_{0-12}$ on treatment day 7 (Day 7) for various study compositions administered to patients as part of the clinical study described in Example 12. Two treatments using combination co-suspension compositions as described herein (GP/FF 72/9.6 and GP/FF 36/9.6) are compared to a placebo and various different active compositions delivering a single active agent (one delivering only glycopyrrolate—GP 36, a second delivering only tiotropium bromide—Spiriva, and three delivering only formoterol fumarate—FF 7.2, FF 9.6, and Foradil).

The percentage of subjects experiencing an improvement in $FEV_1$ of >12% from baseline on treatment day 1 (Day 1) and the rate at which such improvement was experienced is represented in FIG. 21. As can be seen in FIG. 21, the cumulative response and rate of onset provided by the GP/FF 72/9.6 and GP/FF 36/9.6 treatments was greater than the cumulative response and rate of onset provided by Spiriva. Relative to the comparator compositions having only a single active agent, the GP/FF 72/9.6 and GP/FF 36/9.6 treatments provided greater changes from baseline in $FEV_1$ at Day 7 (shown in FIG. 22-FIG. 24).

Figure 25:
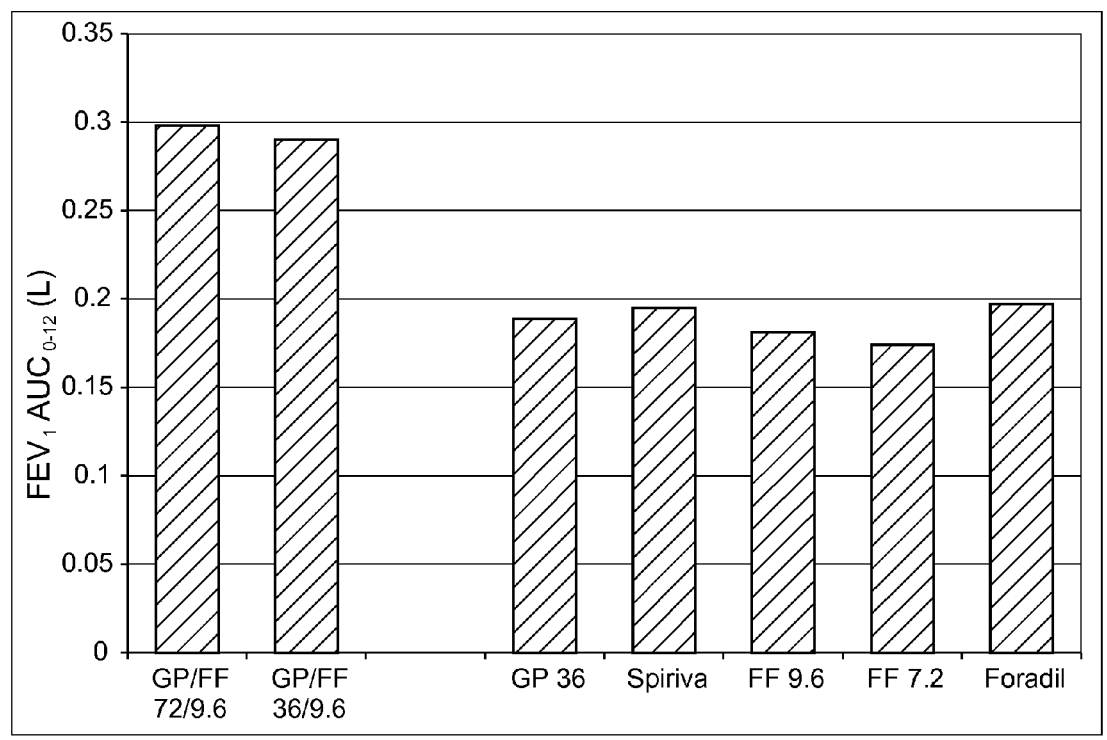
FIG. 25 is a graph illustrating the $FEV_1$ $AUC_{0-12}$ on Day 7 for each of the active study compositions administered to patients as part of the clinical study described in Example 12. The improvement in $FEV_1$ $AUC_{0-12}$ provided by each of the active study compositions relative to placebo is shown.
Figure 26:
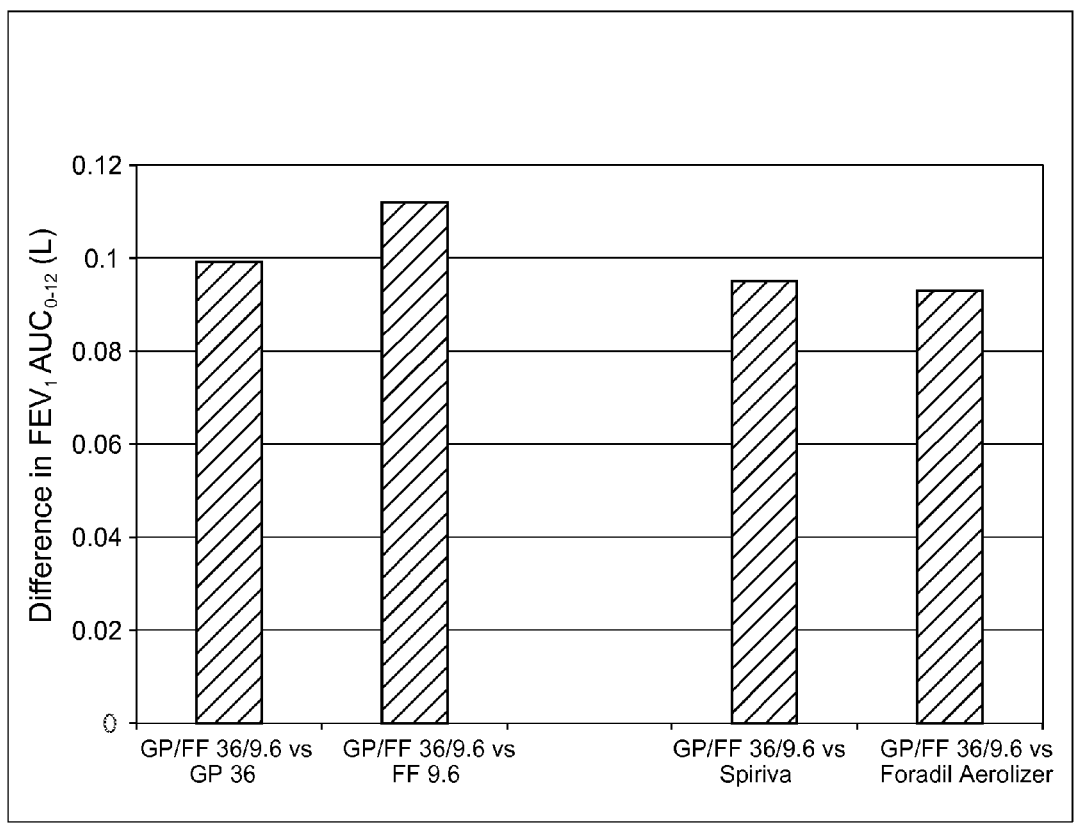
FIG. 26 is a graph illustrating the difference between the $FEV_1$ $AUC_{0-12}$ achieved by the GP/FF 36/9.6 treatment on Day 7 relative to the GP 36, FF 9.6, Spiriva and Foradil active comparators. As can be easily appreciated by reference to FIG. 26, the GP/FF 36/9.6 treatment provided significantly better improvements in $FEV_1$ $AUC_{0-12}$.

Both GP/FF 72/9.6 and GP/FF 36/9.6 were superior to all the comparators for the primary endpoint. FIG. 25 shows the improvement in $FEV_1$ $AUC_{0-12}$ on Day 7 achieved by GP/FF 72/9.6, GP/FF 36/9.6, and each of the active comparators relative to placebo. As is shown in FIG. 25, GP/FF 72/9.6 and GP/FF 36/9.6 provided markedly better improvement in $FEV_1$ $AUC_{0-12}$ on Day 7 relative to the comparator compositions, with the improvement in $FEV_1$ $AUC_{0-12}$ on Day 7 provided by GP/FF 72/9.6 and GP/FF 36/9.6 being at least 80 ml greater than that provided by each of the comparator compositions. The difference in $FEV_1$ $AUC_{0-12}$ on Day 7 shown in FIG. 26 further highlights, for example, the improvement in $FEV_1$ $AUC_{0-12}$ on Day 7 provided by the GP/FF 36/9.6 composition relative to the GP 36, FF 9.6, Spiriva, and Foradil comparators.

Figure 32:
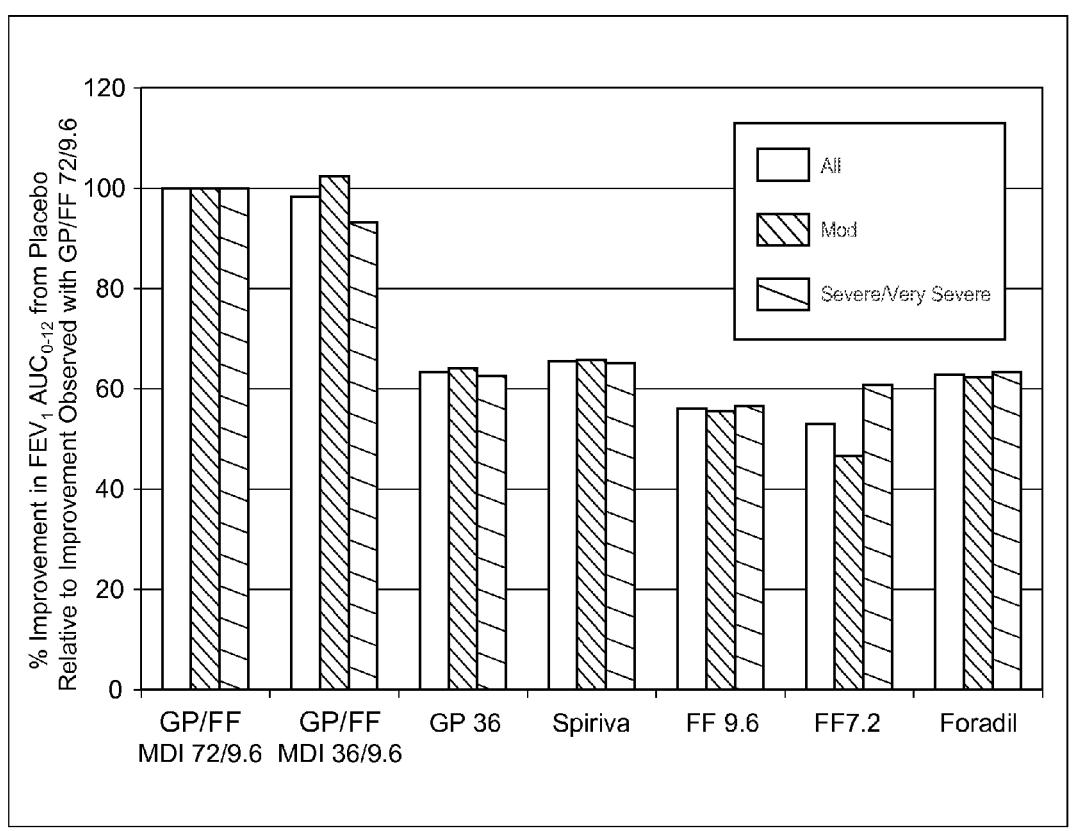
FIG. 32 provides a graph illustrating the consistent patient response achieved in the clinical study described in Example 12 regardless of the severity of the chronic obstructive pulmonary disease suffered by the patients.

Using the improvement in $FEV_1$ $AUC_{0-12}$ provided by the GP/FF 72/9.6 treatment as a reference point, FIG. 32 presents the percent improvement in $FEV_1$ $AUC_{0-12}$ on Day 7 provided by GP/FF 36/9.6 and each of the comparators in all patients, patients with moderate COPD, and patients with severe to very severe COPD. The results shown in FIG. 32 illustrate that the response in patients was consistent regardless of the severity of COPD.

Figure 27:
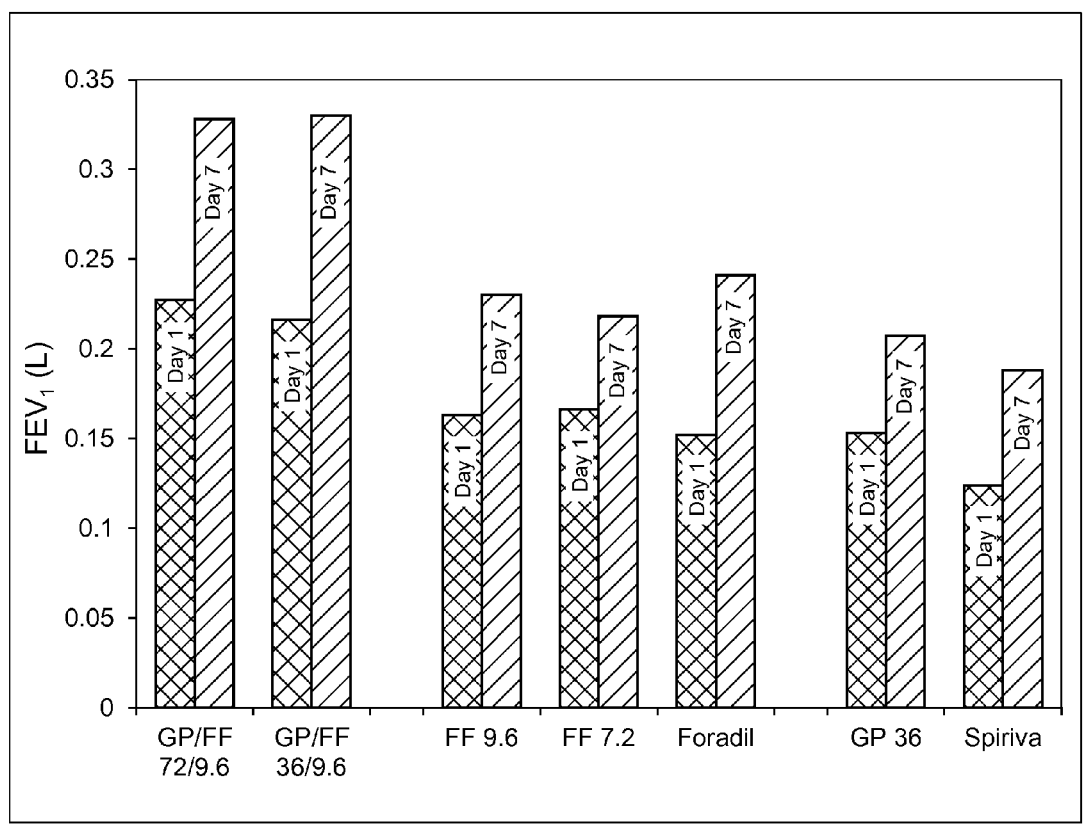
FIG. 27 is a graph showing the Peak $FEV_1$ on treatment day 1 (Day 1) and Day 7 achieved by various study compositions administered to patients as part of the clinical study described in Example 12. The Peak $FEV_1$ shown represents the peak change in $FEV_1$ from baseline provided by each of the active study composition relative to placebo on the study day indicated.
Figure 28:
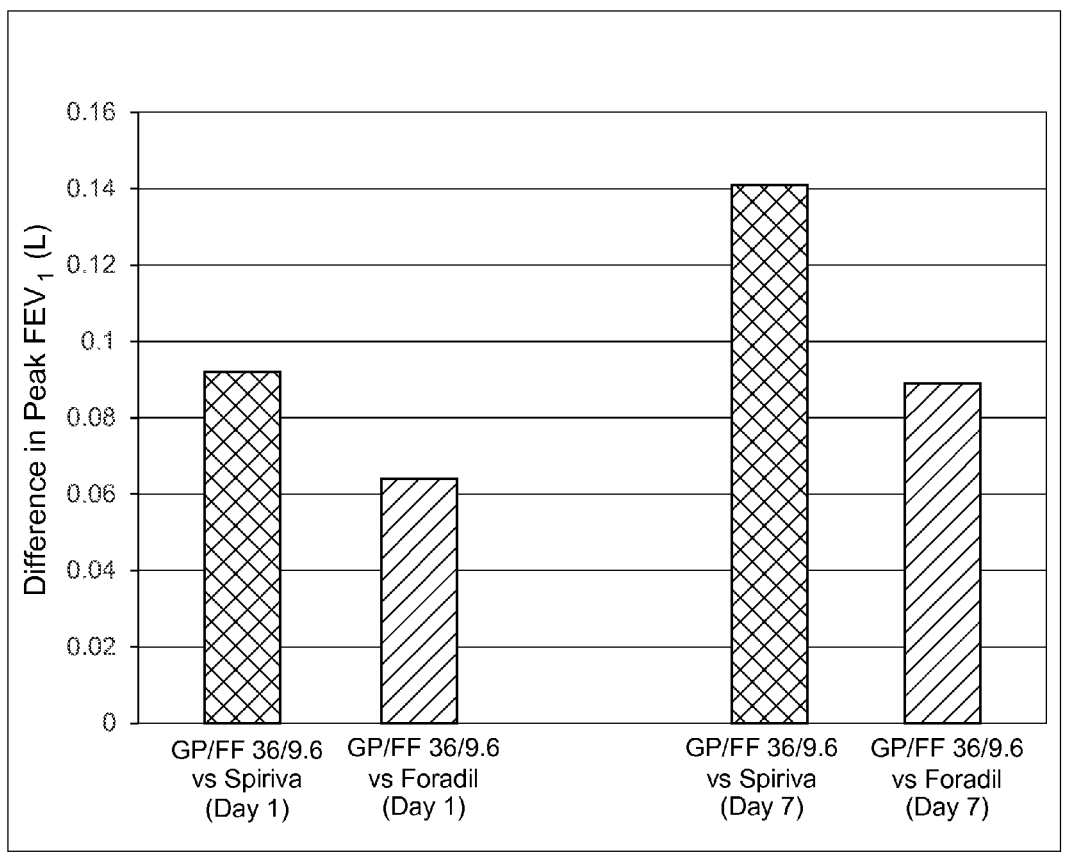
FIG. 28 is a graph illustrating the difference between the Peak $FEV_1$ achieved by the GP/FF 36/9.6 treatment on Day 1 and Day 7 relative to the Spiriva and Foradil active comparators. As can be easily appreciated by reference to FIG. 28, the GP/FF 36/9.6 treatment provided significantly better improvements in Peak $FEV_1$ compared to the active comparators.
Figure 29:
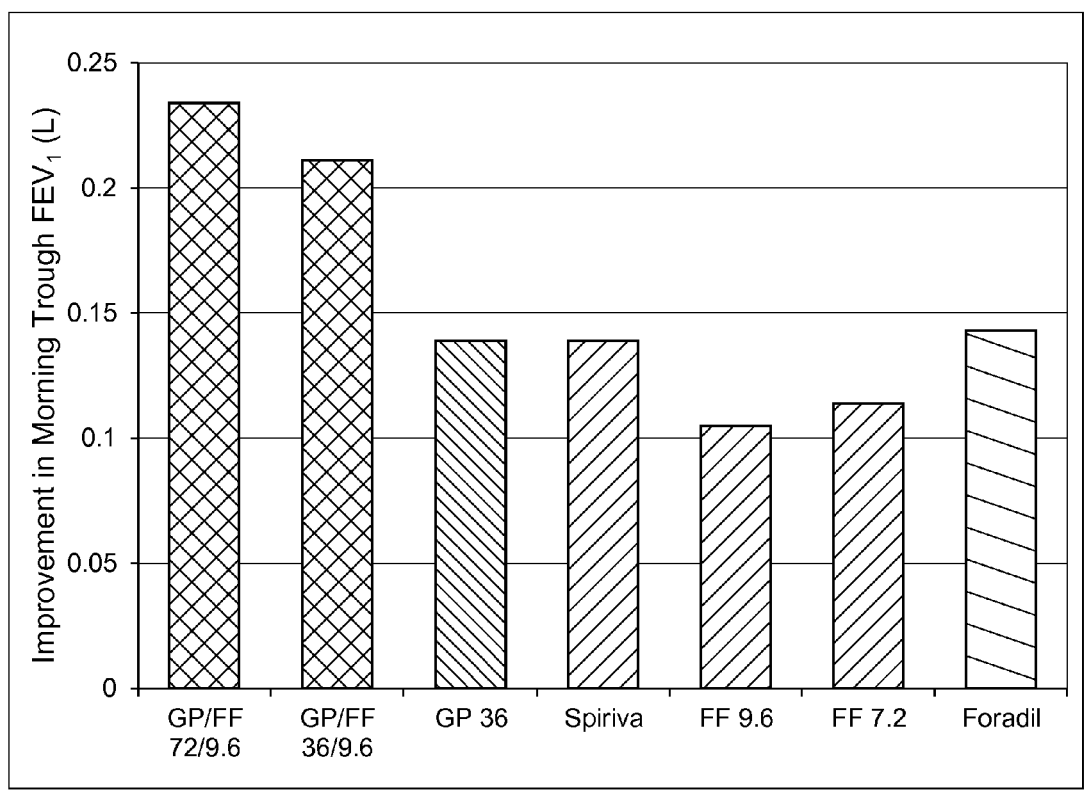
FIG. 29 is a graph illustrating the improvements in Morning Trough $FEV_1$ achieved by various study compositions administered to patients as part of the clinical study described in Example 12. The graph illustrates the improvement in Morning Trough $FEV_1$ values provided by each of the active study compositions relative to placebo.

GP/FF 72/9.6 and GP/FF 36/9.6 were also superior to all other comparators for the secondary endpoints of the study. The Peak $FEV_1$ shown in FIG. 27 represents a change from baseline provided by each of the active study compositions relative to placebo on Day 1 and Day 7 of administration. As shown in FIG. 27, GP/FF 72/9.6 and GP/FF 36/9.6 provided superior Peak $FEV_1$ on both Day 1 and Day 7. FIG. 28 highlights the improvement in Peak $FEV_1$ relative to Spiriva and Foradil provided by GP/FF 72/9.6 and GP/FF 36/9.6 on Day 1 and Day 7. FIG. 29 illustrates the improvement in Morning Trough $FEV_1$ provided by GP/FF 72/9.6, GP/FF 36/9.6, and each of the active comparators relative to placebo. As can be appreciated by reference to FIG. 29, superior increases in $FEV_1$ provided by the two combination co-suspensions are better maintained over time, with the GP/FF 72/9.6 and GP/FF 36/9.6 compositions providing an approximately 50% improvement in Morning Trough $FEV_1$ relative to the other active comparators.

Figure 30:
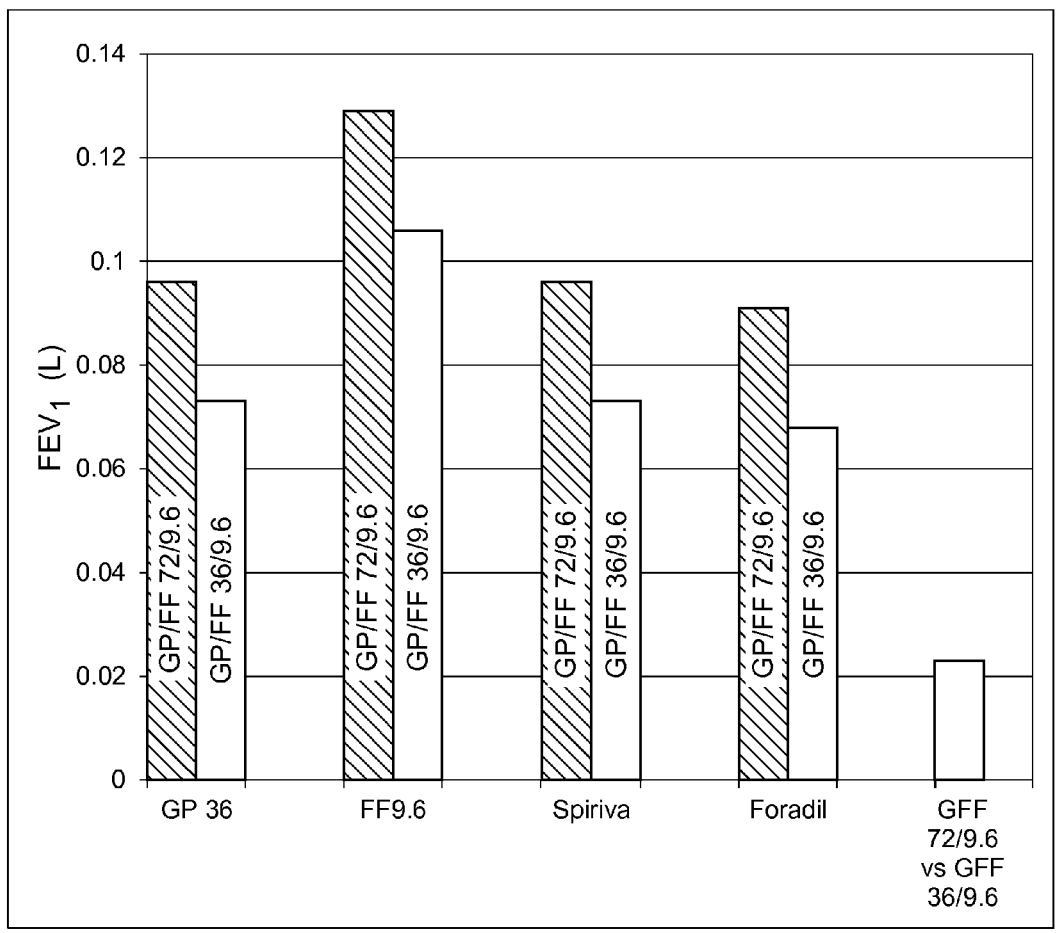
FIG. 30 is a graph showing the difference between the increase in pre-dose $FEV_1$ on Day 7 of the clinical study described in Example 12 provided by two treatments using combination co-suspension compositions as described herein (GP/FF 72/9.6 and GP/FF 36/9.6) relative to the different single active agent comparators and to each other. As can be easily appreciated by reference to FIG. 30, the GP/FF 72/9.6 and GP/FF 36/9.6 treatments provided significantly better improvements in pre-dose $FEV_1$ compared to the single active agent comparators, but did not differ significantly from each other.

FIG. 30 shows the difference between the increase in pre-dose $FEV_1$ on Day 7 provided by GP/FF 72/9.6 and GP/FF 36/9.6 and the increase in pre-dose $FEV_1$ on Day 7 provided by the GP 36, FF 9.6, Spiriva and Foradil comparators. As can be easily appreciated by reference to FIG. 30, relative to the GP 36, FF 9.6, Spiriva and Foradil comparators, the GP/FF 36/9.6 treatment provided significantly greater improvements in pre-dose $FEV_1$ on Day 7.

Figure 31:
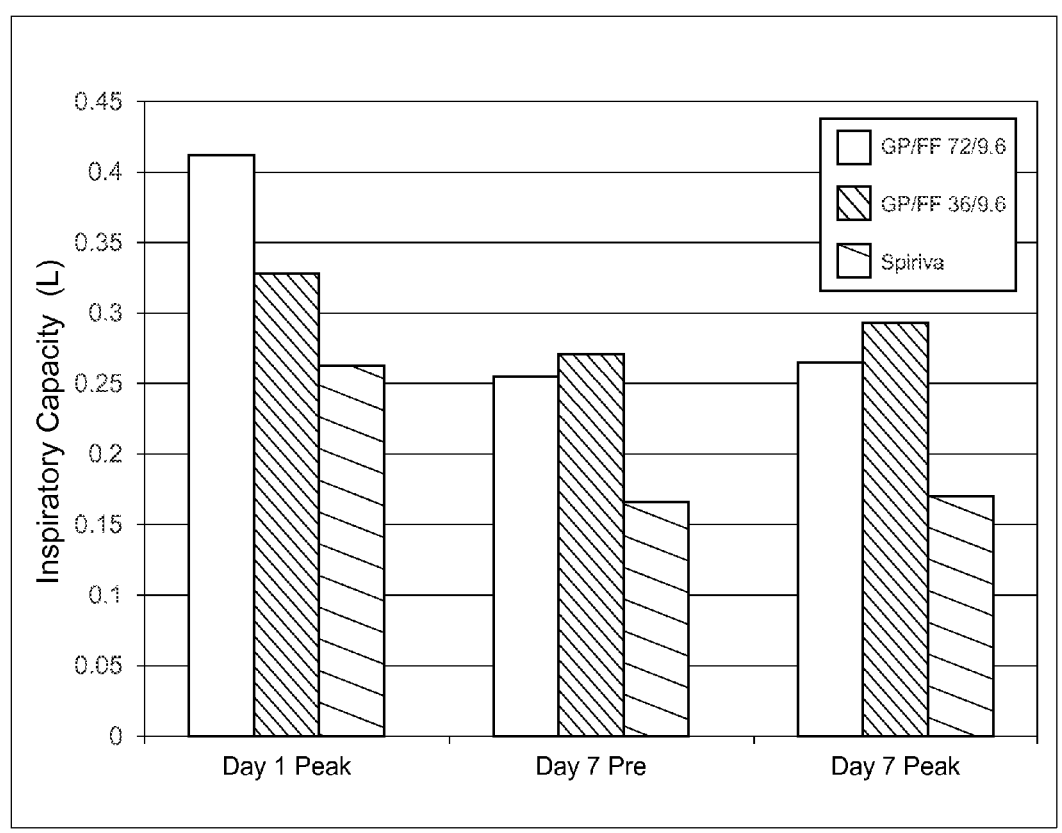
FIG. 31 provides a graph illustrating the Day 1 and 7 peak, and Day 7 pre-dose improvements in inspiratory capacity (IC) relative to placebo provided by the two treatments using combination co-suspension compositions (GP/FF 72/9.6 and GP/FF 36/9.6) and the Spiriva active comparator composition administered as part of the clinical trial described in Example 12.

In addition to the specified secondary endpoints for the study, improvements in inspiratory capacity (IC) were assessed. Both GP/FF 72/9.6, GP/FF 36/9.6 provided greater increases in IC relative to each of the comparators at Day 1 and on Day 7. For patients receiving GP/FF 72/9.6, GP/FF 36/9.6, and Spiriva, FIG. 31 illustrates the peak improvement in IC experienced on Day 1 (Day 1 Peak), the improvement in IC retained in patients prior to administration of the specified test compositions on Day 7 (Day 7 Pre), and the peak improvement in IC experienced in patients on Day 7 after administration of the specified compositions (Day 7 Peak).

The invention claimed is:

1. A method for treating a pulmonary disease or disorder in a patient, the method comprising:
   providing a pharmaceutically acceptable co-suspension deliverable from a metered dose inhaler, the co-suspension comprising:
      a suspension medium comprising a pharmaceutically acceptable propellant;
      one or more species of respirable active agent particles comprising two or more active agents; and
      a plurality of respirable suspending particles different than the active agent particles and comprising a particulate phospholipid material that is substantially insoluble in the suspension medium, wherein the active agent particles and suspending particles are co-suspended in the suspension medium at a weight ratio of total mass of the suspending particles to total mass of the one or more species of active agent particles that ranges from above 1:1 and up to 200:1; and
   administering a therapeutically effective amount of the pharmaceutically acceptable co-suspension.

2. The method of claim 1, wherein providing a pharmaceutically acceptable co-suspension comprises providing a co-suspension comprising two or more active agents selected from short-acting beta agonist, long-acting and ultra long-acting $\beta_2$ adrenergic receptor agonist (LABA), corticosteroid, anti-inflammatory, anti-tussive, bronchodilator, muscarinic antagonist, and long-acting muscarinic antagonist (LAMA) active agents, including any pharmaceutically acceptable salts, esters, or isomers thereof.

3. The method of claim 2, wherein the pulmonary disease or disorder is selected from at least one of asthma, COPD, chronic bronchitis, emphysema, bronchiectasis, allergic rhinitis, sinusitis, pulmonary vasoconstriction, inflammation, allergies, impeded respiration, respiratory distress syndrome, pulmonary hypertension, pulmonary vasoconstriction, pulmonary inflammation experienced with cystic fibrosis, and pulmonary obstruction experienced with cystic fibrosis.

4. The method of claim 3, wherein providing a pharmaceutically acceptable co-suspension comprises providing a co-suspension comprising at least two different species of active agent particles, each of the at least two species of active agent particles comprises a different active agent, and the different active agents are selected from a LAMA active agent selected from glycopyrrolate, dexipirronium, tiotropium, trospium, aclidinium, and darotropium, a LABA active agent selected from bambuterol, clenbuterol, formoterol, salmeterol, carmoterol, milveterol, indacaterol, and saligenin- or indole-containing and adamantyl-derived $\beta_2$ agonists, and a corticosteroid active agent selected from beclomethasone, budesonide, ciclesonide, flunisolide, fluticasone, methyl-prednisolone, mometasone, prednisone and trimacinolone, including any pharmaceutically acceptable salts, esters, or isomers thereof.

5. The method of claim 4, wherein providing a pharmaceutically acceptable co-suspension comprises providing a co-suspension comprising at least three different species of active agent particles, each of the at least three species of active agent particles comprises a different active agent, and the different active agents are selected from a LAMA active agent selected from glycopyrrolate, dexipirronium, tiotropium, trospium, aclidinium, and darotropium, a LABA active agent selected from bambuterol, clenbuterol, formoterol, salmeterol, carmoterol, milveterol, indacaterol, and saligenin- or indole- containing and adamantyl-derived $\beta_2$ agonists, and a corticosteroid active agent selected from beclomethasone, budesonide, ciclesonide, flunisolide, fluticasone, methylprednisolone, mometasone, prednisone and trimacinolone, including any pharmaceutically acceptable salts, esters, or isomers thereof.

6. The method of claim 3, wherein administering a therapeutically effective amount of the pharmaceutically acceptable co-suspension comprises simultaneously delivering therapeutically effective amounts of a LAMA active agent selected from glycopyrrolate, dexipirronium, tiotropium, trospium, aclidinium, and darotropium, and a LABA active agent selected from bambuterol, clenbuterol, formoterol, salmeterol, carmoterol, milveterol, indacaterol, and saligenin- or indole- containing and adamantyl-derived $\beta_2$ agonists, including any pharmaceutically acceptable salts, esters, or isomers thereof.

7. The method of claim 3, wherein administering a therapeutically effective amount of the pharmaceutically acceptable co-suspension comprises simultaneously delivering therapeutically effective amounts of a LAMA active agent selected from glycopyrrolate, dexipirronium, tiotropium, trospium, aclidinium, and darotropium, and a corticosteroid active agent selected from beclomethasone, budesonide, ciclesonide, flunisolide, fluticasone, methyl-prednisolone, mometasone, prednisone and trimacinolone, including any pharmaceutically acceptable salts, esters, or isomers thereof.

8. The method of claim 3, wherein administering a therapeutically effective amount of the pharmaceutically acceptable co-suspension comprises simultaneously delivering therapeutically effective amounts of a LABA active agent selected from bambuterol, clenbuterol, formoterol, salmeterol, carmoterol, milveterol, indacaterol, and saligenin- or indole- containing and adamantyl-derived $\beta_2$ agonists, and a corticosteroid active agent selected from beclomethasone, budesonide, ciclesonide, flunisolide, fluticasone, methylprednisolone, mometasone, prednisone and trimacinolone, including any pharmaceutically acceptable salts, esters, or isomers thereof.

9. The method of claim 3, wherein administering a therapeutically effective amount of the pharmaceutically acceptable co-suspension comprises simultaneously delivering therapeutically effective amounts of a LAMA active agent selected from glycopyrrolate, dexipirronium, tiotropium, trospium, aclidinium, and darotropium, a LABA active agent selected from bambuterol, clenbuterol, formoterol, salmeterol, carmoterol, milveterol, indacaterol, and saligenin- or indole- containing and adamantyl-derived $\beta_2$ agonists, and a corticosteroid active agent selected from beclomethasone, budesonide, ciclesonide, flunisolide, fluticasone, methylprednisolone, mometasone, prednisone and trimacinolone, including any pharmaceutically acceptable salts, esters, or isomers thereof.

10. The method according to claim 1, wherein administering the co-suspension results in a clinically significant increase in $FEV_1$ in the patient.

11. The method of claim 10, wherein administering the co-suspension results in an increase in $FEV_1$ of at least 150 mL within a period of time selected from 0.5 hours or less, 1 hour or less, and 1.5 hours or less.

12. The method of claim 11, wherein administering the co-suspension results in an increase in $FEV_1$ of at least 200 mL within a period of time selected from 0.5 hours or less, 1 hour or less, and 1.5 hours or less.

13. The method of claim 12, wherein administering the co-suspension results in an increase in $FEV_1$ of at least 250 mL within a period of time selected from 0.5 hours or less, 1 hour or less, and 1.5 hours or less.

14. The method of claim 13, wherein administering the co-suspension results in an increase in $FEV_1$ of at least 300 mL within a period of time selected from 0.5 hours or less, 1 hour or less, and 1.5 hours or less.

15. The method of claim 14, wherein administering the co-suspension results in an increase in $FEV_1$ of at least 350 mL within a period of time selected from 0.5 hours or less, 1 hour or less, and 1.5 hours or less.

16. The method according to claim 10, wherein the clinically significant increase in $FEV_1$ achieved by administering the co-suspension remains clinically significant for a period of time selected from up to 4 hours, up to 6 hours, up to 8hours, up to 10 hours, and up to 12 hours, or more.

17. The method according to claim 1, wherein administering the co-suspension results in a clinically significant increase in $FEV_1$ in the patient and the clinically significant increase in $FEV_1$ is a significant improvement over the increase provided by a composition delivering only one of the two or more active agents.

18. The method of claim 17, wherein the significant improvement in $FEV_1$ is 70 mL or greater.

19. The method of claim 18, wherein the significant improvement in $FEV_1$ is 80 mL or greater.

20. The method of claim 19, wherein the significant improvement in $FEV_1$ is 90 mL or greater.

21. The method according to claim 18, wherein the significant improvement is measured as an improvement in peak $FEV_1$.

22. The method according to claim 18, wherein the significant improvement is measured as an improvement in $FEV_1$ $AUC_{0-12}$.

23. The method according to claim 1, wherein administering the co-suspension results in a clinically significant increase in inspiratory capacity (IC).

24. The method according to claim 23, wherein the clinically significant increase in IC is an increase of 100 mL or greater.

25. The method according to claim 24, wherein the clinically significant increase in IC is an increase of 200 mL or greater.

26. The method according to claim 25, wherein the clinically significant increase in IC is an increase of 300 mL or greater.

27. The method according to claim 26, wherein the clinically significant increase in IC is an increase of 350 mL or greater.

28. The method according to claim 23, wherein the clinically significant increase in IC is achieved in 2 hours, or less.

29. The method according to claim 23, wherein the clinically significant increase in IC is achieved in 1 hour, or less.

30. A method according to claim 4, wherein the one or more species of respirable active agent particles are substantially insoluble in the propellant.

31. The method of according to claim 4, wherein the respirable suspending particles comprise perforated microstructures.

32. The method according to claim 31, wherein the respirable suspending particles comprise DSPC and calcium chloride.

33. The method according to claim 4, wherein the respirable suspending particles included in the co-suspension are included in the suspension medium at a concentration selected from between about 1 mg/mL and about 15 mg/mL, between about 3 mg/mL and about 10 mg/mL, between about 5 mg/mL and about 8 mg/mL, and about 6 mg/mL.

34. The method according to claim 4, wherein the weight ratio of total mass of the suspending particles to total mass of the one or more species of active agent particles is selected from above about 1.5:1, up to about 5:1, up to about 10:1, up to about 15:1, up to about 17:1, up to about 20:1, up to about 30:1, up to about 40:1, up to about 50:1, up to about 60:1, up to about 75:1, up to about 100:1, up to about 150:1, and up to about 200:1.

35. The method according to claim 4, wherein the weight ratio of total mass of the suspending particles to total mass of the one or more species of active agent particles is selected from between about 3:1 and about 15:1 and between about 2:1 and 8:1.

36. The method according to claim 4, wherein the respirable suspending particles included in the co-suspension remain co-suspended with the active agent particles even when subjected to buoyancy forces amplified by centrifugation at an acceleration selected from accelerations of at least 1 g, at least 10 g, at least 50 g, and at least 100 g.

37. The method as in any one of claims 2, 3, 4, and 5, in which the active agent particles included in the co-suspension comprise a first species and a second species of active agent particles, with the first species of active agent particles comprising glycopyrrolate, including any pharmaceutically acceptable salts, esters, or isomers thereof, and the second species of active agent particles comprising formoterol, including any pharmaceutically acceptable salts, esters, or isomers thereof.

38. The method of claim 37, wherein the first species of active agent particles comprise crystalline glycopyrrolate and the second species of active agent particles comprise crystalline formoterol.

39. The method according to claim 37, wherein administering a therapeutically effective amount of the pharmaceutically acceptable co-suspension comprises administering the co-suspension to the patient up to two times daily, and each administration comprises delivering no more than 150 μg of the LAMA active agent and no more than 12 μg of the LABA active agent.

40. The method according to claim 37, wherein administering a therapeutically effective amount of the pharmaceutically acceptable co-suspension comprises administering the co-suspension to the patient up to two times daily, and each administration comprises delivering no more than 100 μg of the LAMA active agent and no more than 12 μg of the LABA active agent.

41. The method according to claim 37, wherein administering a therapeutically effective amount of the pharmaceutically acceptable co-suspension comprises administering the co-suspension to the patient up to two times daily, and each administration comprises delivering no more than 80 μg of the LAMA active agent and no more than 12 μg of the LABA active agent.

42. The method according to claim 37, wherein administering a therapeutically effective amount of the pharmaceutically acceptable co-suspension comprises administering the co-suspension to the patient up to two times daily, and each administration comprises delivering no more than 50 μg of the LAMA active agent and no more than 12 μg of the LABA active agent.

43. The method as in any one of claims 1, 2, 3, 4, and 5, in which the weight ratio of total mass of the suspending particles to total mass of the one or more species of active agent particles is selected from the ranges of between about 10:1 and about 200:1, between about 60:1 and about 200:1, between about 15:1 and about 60:1, and between about 15:1 and 170:1.

44. The method according to claim 37, wherein the pharmaceutically acceptable salt of glycopyrrolate is selected from fluoride, chloride, bromide, iodide, nitrate, sulfate, phosphate, formate, acetate, trifluoroacetate, propionate, butyrate, lactate, citrate, tartrate, malate, maleate, succinate, benzoate, p-chlorobenzoate, diphenyl-acetate or triphenylacetate, o-hydroxybenzoate, p-hydroxybenzoate, 1-hydroxynaphthalene-2-carboxylate, 3-hydroxynaphthalene-2-carboxylate, methanesulfonate, and benzenesulfonate salts.

45. The method according to claim 44, wherein the pharmaceutically acceptable salt of glycopyrrolate is selected from fluoride, chloride, bromide, and iodide salts.

46. The method according to claim 45, wherein the pharmaceutically acceptable salt of glycopyrrolate is 3-[(cyclopentyl-hydroxyphenylacetyl)oxy]-1,1-dimethylpyrroli dinium bromide.

47. The method according to claim 37, wherein the pharmaceutically acceptable salt of formoterol is selected from hydrochloric, hydrobromic, sulfuric, phosphoric, fumaric, maleic, acetic, lactic, citric, tartaric, ascorbic, succinic, glutaric, gluconic, tricarballylic, oleic, benzoic, p-methoxybenzoic, salicylic, o- and p-hydroxybenzoic, p-chlorobenzoic, methanesulfonic, p-toluenesulfonic and 3-hydroxy-2-naphthalene carboxylic acid salts.

48. The method according to claim 47, wherein the pharmaceutically acceptable salt, ester, or isomer of formoterol is formoterol fumarate.

49. A method according to claim 30, wherein the propellant is selected from an HFA propellant, a PFC propellant, and combinations thereof.

* * * * *